United States Patent
Shiau et al.

(10) Patent No.: US 9,090,617 B1
(45) Date of Patent: Jul. 28, 2015

(54) AGONISTS OF SRC HOMOLOGY-2 CONTAINING PROTEIN TYROSINE PHOSPHATASE-1 AND TREATMENT METHODS USING THE SAME

(71) Applicants: National Taiwan University, Taipei (TW); NATIONAL YANG-MING UNIVERSITY, Taipei (TW); DCB-USA LLC, Wilmington, DE (US)

(72) Inventors: Chung-Wai Shiau, Taipei (TW); Kuen-Feng Chen, Taipei (TW)

(73) Assignees: NATIONAL TAIWAN UNIVERSITY, Taipei (TW); NATIONAL YANG-MING UNIVERSITY, Taipei (TW); DCB-USA LLC, Wilmington, DE (US)

( * ) Notice: Subject to any disclaimer, the term of this patent is extended or adjusted under 35 U.S.C. 154(b) by 0 days.

(21) Appl. No.: 14/665,497

(22) Filed: Mar. 23, 2015

Related U.S. Application Data

(63) Continuation-in-part of application No. 14/235,620, filed as application No. PCT/US2012/049446 on Aug. 3, 2012.

(60) Provisional application No. 61/514,555, filed on Aug. 3, 2011.

(51) Int. Cl.
*C07D 471/04* (2006.01)
*C07C 275/40* (2006.01)
*C07C 311/29* (2006.01)
*C07C 255/59* (2006.01)
*C07C 255/60* (2006.01)
*C07D 213/81* (2006.01)
*C07D 215/233* (2006.01)

(52) U.S. Cl.
CPC ............ *C07D 471/04* (2013.01); *C07C 255/59* (2013.01); *C07C 255/60* (2013.01); *C07C 275/40* (2013.01); *C07C 311/29* (2013.01); *C07D 213/81* (2013.01); *C07D 215/233* (2013.01)

(58) Field of Classification Search
None
See application file for complete search history.

(56) References Cited

PUBLICATIONS

Wei-Tien Tai et al., "Discovery of Novel Src Homology Region 2 Domain-Containing Phosphatase 1 Agonists from Sorafenib for the Treatment of Hepatocellular Carcinoma", Hepatology, vol. 59, No. 1, 2014.
Kuen-Feng Chen et al., Sorafenib and its derivative SC-49 sensitize hepatocellular carcinoma cells to CS-1008, a humanized anti-TNFRSF10B (DR5) antibody, British Journal of Pharmacology(2013) 168 658-672.
Chao-Yuan Huang, "A sorafenib derivative and novel SHP-1 agonist, SC-59, acts synergistically with radiotherapy in hepatocellular carcinoma cells through inhibition of STAT3", Cancer Letters 349 (2014) 136-143.
Wei-Tien Tai, "SC-60, a dimer-based sorafenib derivative, shows a better anti-hepatocellular carcinoma effect than sorafenib in a preclinical hepatocellular carcinoma model", Mol Cancer Ther; 13(1) Jan. 2014.

*Primary Examiner* — Timothy R Rozof
(74) *Attorney, Agent, or Firm* — WPAT, P.C.; Anthony King

(57) ABSTRACT

The present invention provides new compounds of formula I, II or III, which have Src homology-2 containing protein tyrosine phosphatase-1 (SHP-1) agonist activity. Also provided are treatment methods using the compounds of formula I, II or III.

10 Claims, 36 Drawing Sheets

Formula I

Formula II

Formula III

General synthetic procedure for Formula I, II, III: a, K₂CO₃, DMF; b, pyridine, THF; c. Et₃N, dioxane

A

B

A

B

C (D)

(E)

(F)

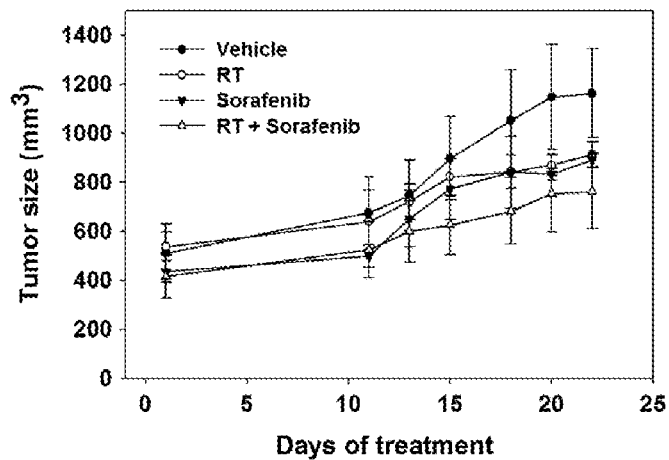
Fig. 30E
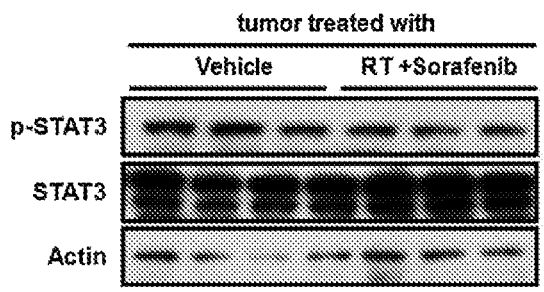
FIG. 30F
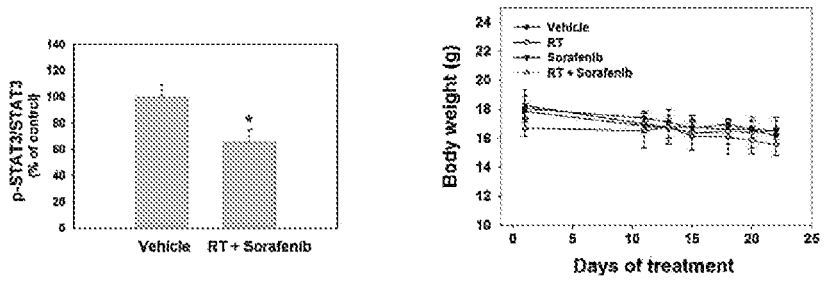
Fig. 30G
FIG. 30H

AGONISTS OF SRC HOMOLOGY-2 CONTAINING PROTEIN TYROSINE PHOSPHATASE-1 AND TREATMENT METHODS USING THE SAME

CROSS-REFERENCES TO RELATED APPLICATIONS

This application claims a continuation-in-part of U.S. patent application Ser. No. 14/235,620, filed on Jan. 28, 2014, which claims the priority benefit of Provisional Application No. 61/514,555, filed on 3 Aug. 2011. The entirety of each of the above-mentioned patent applications is hereby incorporated by reference herein and made a part of this specification.

FIELD OF THE INVENTION

The present invention relates to new compounds having Src homology-2 containing protein tyrosine phosphatase-1 (SHP-1) agonist activity and treatment methods using the same.

BACKGROUND OF THE INVENTION

SHP-1, a protein-tyrosine phosphatase with two Src homology 2 (SH2) domains, is a regulator of various intracellular signaling molecules, such as signal transducer and activator of transcription 3 (STAT3), KIT, CD22, CD5, CD72, SHPS-1, TIMP (metalloproteinases), CDK2, p27, SRC, ZAP70, IL-10, NF-κB, Lck, 3BP2, Lyn and cyclin D1. STAT3 is a transcription factor which regulates cell growth and survival by modulating the expression of target genes. It acts as an oncogene which is constitutively active in many cancers including liver, lung, head and neck, prostate, and breast as well as myeloma and leukemia. A key regulator of STAT3 activity is SHP-1. From a mechanistic perspective, SHP-1 exhibits protein phosphatase activity which reduces the level of Phospho-STAT3 (P-STAT) and subsequently blocks the dimerization of P-STAT3. Therefore, expression of target genes, such as cyclin D1 and survivin transcribed by STAT3, is significantly reduced. In addition, studies of SHP-1 protein and SHP-1 mRNA showed that expression level of SHP-1 was low in most cancer cells; and genetic increase in SHP-1 in cancer cells resulted in the suppression of cell growth, suggesting that the SHP-1 gene acts as a tumor suppressor. From the drug discovery point of view, development of a small molecule which can reduce P-STAT3 and increase SHP-1 level is a promising direction for cancer therapy. SHP-1 also play an important role in bone remodeling, a process of bone-forming osteoblasts and bone-resorbing osteoclasts. Loss function of SHP-1 results in osteoclast and eventually leads to osteoporosis. Therefore, enhancement of SHP-1 activity might be a direction for osteoporosis patient. In addition, increase of SHP-1 is benefit for the macrophages of multiple sclerosis patients

BRIEF SUMMARY OF THE INVENTION

The present invention is based on the unexpected finding that newly designed compounds act as SHP-1 agonists and have the ability to reduce P-STAT3, and are useful for treating certain diseases, such as cancer. Specifically, the compounds of the invention do not block activity of kinases, such as Raf-1 and VEGFR2.

Particularly, in one aspect, the invention provides a compound of formula I

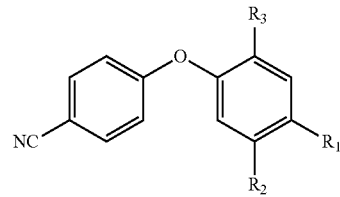

wherein $R_1$, $R_2$, and $R_3$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarkyl, —$(C)_m$NHC(X)NH$(C)_n R_a$—, —$(C)_p$NHC(X)$R_b$—, —$(C)_q$NHS(O)$_2 R_c$, —$(C)_r$(X)NHR$_d$—, or —$(C)_s$NH(C)$_t R_e$;

wherein $R_a$, $R_b$, $R_c$, $R_d$ and $R_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarkyl;

X=O or S; and m, n, p, q, r, s, t=0, 1, or 2.

In another aspect, the present invention provides a compound of Formula II, including a compound of Formula II(a), a compound of Formula II(b), or a compound of Formula II(c),

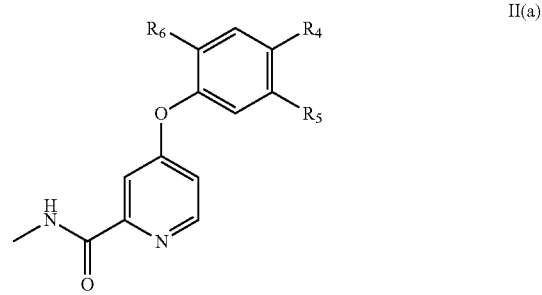

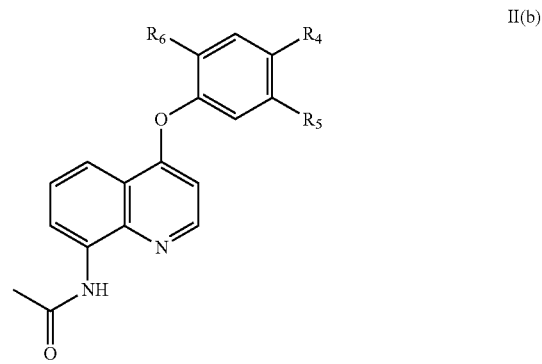

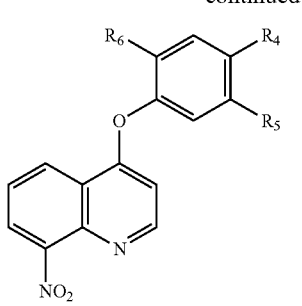

II(c)

wherein R₄, R₅ and R₆ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$R$_a$—, —(C)$_p$NHC(X)R$_b$—, —(C)$_q$NHS(O)$_2$R$_c$, —(C)$_r$(X)NHR$_d$—, or —(C)$_s$NH(C)$_t$R$_e$;

wherein R$_a$, R$_b$, R$_c$, R$_d$ and R$_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In a further aspect, the invention provides a compound of Formula III

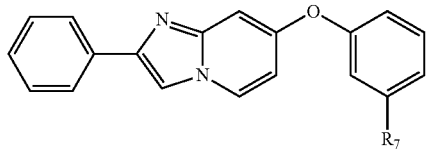

III wherein R₇ is hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$R$_a$—, —(C)$_p$NHC(X)R$_b$—, —(C)$_q$NHS(O)$_2$R$_c$, —(C)$_r$(X)NHR$_d$—, or —(C)$_s$NH(C)$_t$R$_e$;

wherein R$_a$, R$_b$, R$_c$, R$_d$ and R$_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

The present invention also provides a pharmaceutical composition comprising one or more of the above-described compounds. The pharmaceutical composition of the invention may be used for increasing expression levels or biological activity of SHP-1 in a cell, or treating a disease or condition characterized by decreased expression levels or biological activity of Src homology-2 containing protein tyrosine phosphatase-1, which includes but is not limited to cancer (e.g. hepatocellular carcinoma, leukemia, lung cancer, breast cancer, renal cancer, thyroid cancer, head and neck cancer, sclerosis and osteoporosis. Also within the scope of this invention is the use of any of the above-described compounds for increasing expression levels or biological activity of SHP-1 in a cell, or treating a disease or condition characterized by decreased expression levels or biological activity of SHP-1 as described herein and for the manufacture of a medicament for treating the same.

Also provided is a method for increasing SHP-1 expression levels or biological activity in a cell, comprising contacting the cell with an effective amount of a compound or a pharmaceutical composition as described herein.

Further provided is a method for treating a disease or condition characterized by decreased expression levels or biological activity of SHP-1 in a subject in need thereof, comprising administering to the subject an effective amount of a compound or a pharmaceutical composition as described herein.

The various embodiments of the present invention are described in details below. Other characteristics of the present invention will be clearly presented by the following detailed descriptions and drawings about the various embodiments and claims.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown.

In the drawings.

Figure 32:
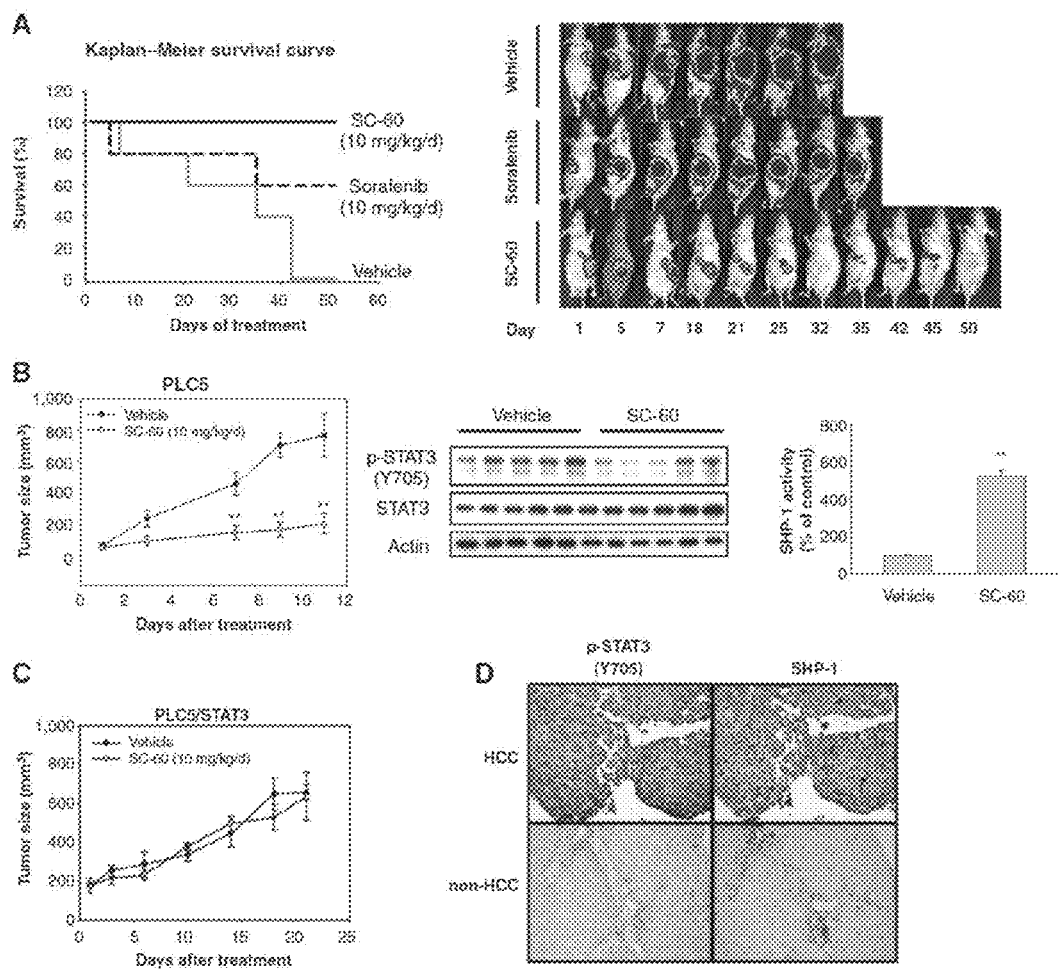

FIG. 32 shows in vivo effects of SC-60 on hepatocellular carcinoma (HCC) xenograft and orthotopic animal models. (A)SC-60 treatment resulted in significant tumor growth inhibition and survival benefits in a hepatocellular carcinoma orthotopic model. Left, survival curve of hepatocellular carcinoma orthotopic mice receiving different adjuvant therapies at indicated times. PLC5/luc2-bearing orthotopic mice received sorafenib, SC-60, or vehicle orally at 10 mg/kg/day (n=6). Right, tumor growth was monitored by IVIS imaging system at the indicated times. (B)SC-60 treatment had a significant antitumor effect on subcutaneous PLC5 tumor-bearing mice. Left, mice received SC-60 at 10 mg/kg/day and tumor growth was measured twice weekly. Points, mean; bars, SE (n=10); **, P<0.01. Middle, analysis of p-STAT3 and STAT3 in PLC5 tumors. Right, SHP-1 phosphatase activity in SC-60-treated tumor sample. (C)SC-60 did not induce a significant tumor inhibition effect in a STAT3-ovrexpression hepatocellular carcinoma model. (D) representative immunohistochemical patterns showed a expression of p-STAT3 and suppressed status of SHP-1 in hepatocellular carcinoma samples (high magnification, ×200).

Figure 33:
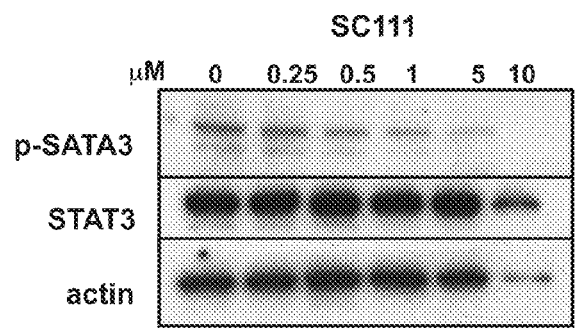

FIG. 33 shows that SC-111 is specific SHP-1 inhibitor.

Figure 34:
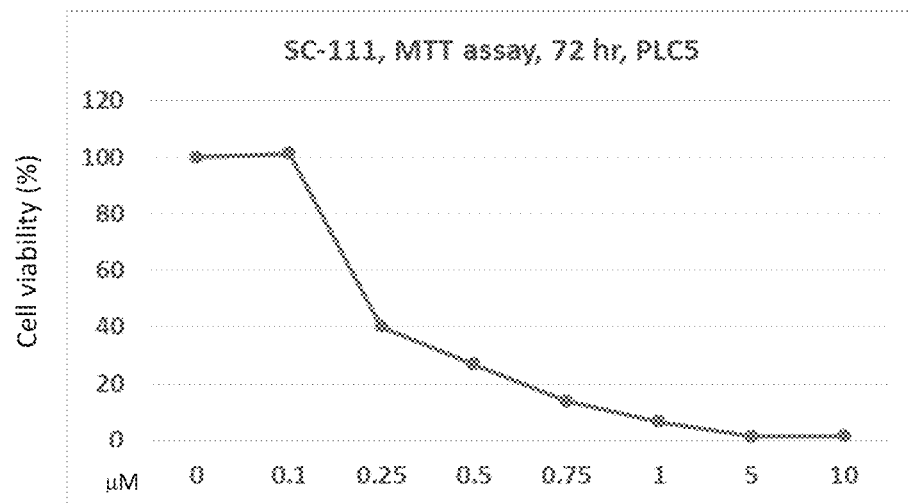

FIG. 34 shows that SC-111 exhibits antitumor effect in HCC cells.

Figure 35:
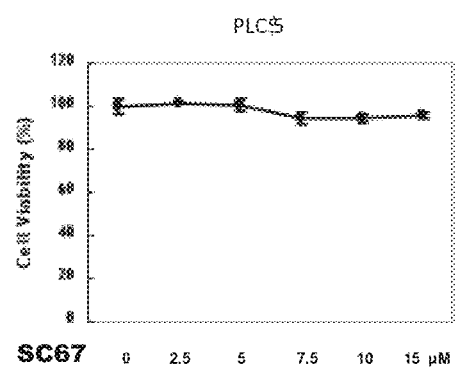

FIG. 35 shows that SC-37 has no activity in inducing cancer cell apoptosis.

DETAILED DESCRIPTION OF THE INVENTION

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a sample" includes a plurality of such samples and equivalents thereof known to those skilled in the art.

Sorafenib (BAY43-9006, Nexavar) has been used clinically for renal carcinoma and hepatocellular carcinoma (HCC). It is known as a multiple kinase inhibitor that represses the activity of Raf-1 and other tyrosine kinases such as VEGFR2, VEGFR3, Flt-3, PDGFR, and FGFR-1.

In this invention, we studied the relationship between the structure of sorafenib and its bioactivity and modified the structure of sorafenib. We accordingly developed a number of sorafenib derivatives without the ability to block the kinase activity, and unexpectedly found that these compounds exhibit good therapeutic effects in certain diseases, such as cancer, at least comparable with that of sorafenib. According to the invention, the newly designed compounds of the invention act as SHP-1 agonists and are useful for treating a disease or condition characterized by decreased expression levels or biological activity of SHP-1, such as cancer (e.g. hepatocellular carcinoma, hepatocellular carcinoma, leukemia, lung cancer, breast cancer, renal cancer, thyroid cancer, head and neck cancer, sclerosis and osteoporosis). The compounds of the invention also provide a new theraptic option for patients with the resistance to kinase inhibitors. These tumors generate kinase mutation after treatment and constitutely in the phosporylated active form, even in the present of a kinase inhibitor. Therefore, upregulation of a tumor suppressor, especially SHP-1, to repress the active mutation form of kinases is a promising direction for chemo-resistance patients. In other words, the compounds of the invention, acting through a new targeting mechanism (kinase independent), provide alternative therapeutic options that may be helpful in the treatment of cancer with resistance to conventional medical therapeutics.

In one aspect, the present invention provides a compound of formula I

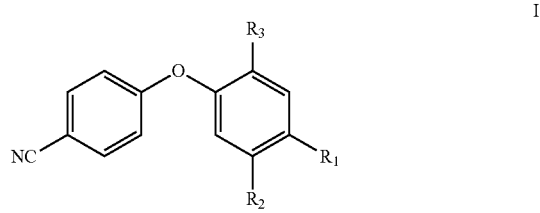

wherein $R_1$, $R_2$, and $R_3$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$R$_a$—, —(C)$_p$NHC(X)R$_b$—, —(C)$_q$NHS(O)$_2$R$_e$, —(C)$_r$(X)NHR$_d$—, or —(C)$_s$NH(C)$_t$R$_e$;

wherein $R_a$, $R_b$, $R_c$, $R_d$ and $R_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In one embodiment, the compound of formula I includes those in which $R_1$, $R_2$, and $R_3$ are independently hydrogen, optionally substituted lower alkyl, —(C)$_m$NHC(X)NH(C)$_n$R$_a$—, —(C)$_p$NHC(X)R$_b$—, —(C)$_q$NHS(O)$_2$R$_c$, or —(C)$_s$NH(C)$_t$R$_e$.

In another embodiment, the compound of formula I includes those in which $R_a$, $R_b$, $R_c$, $R_d$ and $R_e$ are independently phenyl or naphthyl, optionally substituted with 1 to 3 groups selected from the group consisting of halo, optionally substituted lower alkyl (such as halo-substituted lower alkyl, e.g. trifluoromethyl), optionally substituted alkoxyl (e.g. such as halo-substituted lower alkoxyl, e.g. trifluoromethyl) and optionally substituted aryloxy (e.g. cyano-substituted phenoxy).

In certain examples, the compound of formula I is one of the compounds SC-1, SC-48, SC-49, SC-54, SC-55, SC-56, SC-58, SC-43, SC-44, SC-45, SC-50, SC-51, SC-52, SC-59, SC-60 and SC-40 as listed in table 1.

TABLE 1

| Cpd | R₁ | R₂ | R₃ |
|---|---|---|---|
| SC-1 | (tert-butyl)-NH-C(O)-NH-(4-chloro-3-trifluoromethylphenyl) | H | H |
| SC-48 | (tert-butyl)-NH-C(O)-NH-CH₂-(3,4-dimethoxyphenyl) | H | H |
| SC-49 | (neopentyl)-NH-C(O)-NH-(4-chloro-3-trifluoromethylphenyl) | H | H |
| SC-54 | (neopentyl)-NH-C(O)-NH-CH₂-(3,4-dimethoxyphenyl) | H | H |
| SC-55 | (neopentyl)-NH-C(O)-NH-CH₂-(3-trifluoromethoxyphenyl) | H | H |
| SC-56 | (tert-butyl)-NH-C(O)-NH-CH(CH₃)-(1-naphthyl) | H | H |
| SC-58 | (tert-butyl)-NH-C(O)-NH-CH₂-(4-chloro-3-trifluoromethylphenyl) | H | H |

TABLE 1-continued

Structure: 4-cyanophenyl-O-phenyl with substituents R₁ (para to O on second ring), R₂ (meta), R₃ (ortho)

| Cpd | R₁ | R₂ | R₃ |
|---|---|---|---|
| SC-43 | H | -NH-C(=O)-NH-(4-chloro-3-trifluoromethylphenyl) | H |
| SC-44 | H | -NH-S(=O)₂-(3-trifluoromethylphenyl) | H |
| SC-45 | H | -NH-CH₂-(3-trifluoromethoxyphenyl) | H |
| SC-50 | H | -NH-C(=O)-NH-(3-fluorophenyl) | H |
| SC-51 | H | -NH-C(=O)-phenyl | H |
| SC-52 | H | -NH-S(=O)₂-phenyl | H |
| SC-59 | H | -NH-C(=O)-NH-(4-chloro-3-trifluoromethylphenyl) | Me |
| SC-60 | H | -NH-C(=O)-NH-[4-methyl-3-(3-cyanophenoxy)phenyl] | Me |

In another aspect, the present invention provides a compound of Formula II, including a compound of formula II(a), a compound of formula II(b) or a compound of formula II(c),

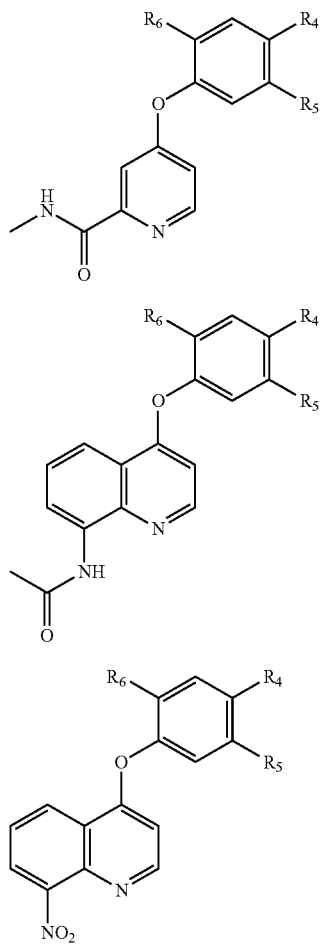

wherein $R_4$, $R_5$ and $R_6$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$R$_a$—, —(C)$_p$NHC(X)R$_b$—, —(C)$_q$NHS(O)$_2$R$_e$, —(C)$_r$(X)NHR$_d$—, or —(C)$_s$NH(C)$_t$R$_e$;

wherein $R_a$, $R_b$, $R_c$, $R_d$ and $R_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In one embodiment, the compound of formula II includes those in which $R_4$, $R_5$ and $R_6$ are independently hydrogen, optionally substituted lower alkyl, —(C)$_m$NHC(X)NH(C)$_n$R$_a$—, —(C)$_p$NHC(X)R$_b$—, —(C)$_n$NHS(O)$_2$R$_c$, or —(C)$_s$NH(C)$_t$R$_e$.

In another embodiment, the compound of formula II includes those in which $R_a$, $R_b$, $R_c$, $R_d$ and $R_e$ are independently phenyl or naphthyl, optionally substituted with 1 to 3 groups selected from the group consisting of halo, optionally substituted lower alkyl (such as halo-substituted lower alkyl, e.g. trifluoromethyl), optionally substituted alkoxyl (e.g. such as halo-substituted lower alkoxyl, e.g. trifluoromethyl) and optionally substituted aryloxy (e.g. cyano-substituted phenoxy).

In certain examples, the compound of formula II is one of the compounds SC-31, SC-32, SC-33, SC-34 and SC-35, as listed in Table 2.

TABLE 2

| Cpd | $R_4$ | $R_5$ | $R_6$ |
|---|---|---|---|
| SC-31 | H | —NHC(O)NH-(3-F-phenyl) | H |
| SC-32 | H | —NH-CH$_2$-(3-OCF$_3$-phenyl) | H |
| SC-33 | H | —NHS(O)$_2$-(3-CF$_3$-phenyl) | H |
| SC-34 | H | —NHC(O)-phenyl | H |
| SC-35 | H | —NHS(O)$_2$-phenyl | H |

In a further aspect, the present invention provides a compound of Formula III

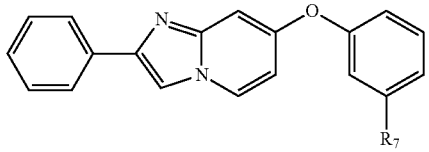

III wherein $R_7$ is hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl, —(C)$_m$NHC(X)NH(C)$_n$R$_a$—, —(C)$_p$NHC(X)R$_b$—, —(C)$_q$NHS(O)$_2$R$_c$, —(C)$_r$(X)NHR$_d$—, or —(C)$_s$NH(C)$_t$R$_e$;

wherein $R_a$, $R_b$, $R_c$, $R_d$ and $R_e$ are independently hydrogen, halo, hydroxyl, optionally substituted alkoxyl, optionally substituted thioalkoxy, optionally substituted alkyl, optionally substituted lower alkenyl, optionally substituted low alkynyl, optionally substituted cycloalkyl, optionally substituted heterocycloalkyl, optionally substituted aryl, optionally substituted aralkyl, optionally substituted heteroaryl, optionally substituted heteroarakyl;

X=O or S; and m, n, p, q, r, s, t=0, 1, or 2.

In one embodiment, the compound of formula III includes those in which wherein $R_7$ is independently hydrogen, optionally substituted lower alkyl, —(C)$_m$NHC(X)NH(C)$_m$R$_a$—, —(C)$_p$NHC(X)R$_b$—, —(C)$_q$NHS(O)$_2$R$_c$, or —(C)$_s$NH(C)$_t$R$_e$.

In another embodiment, the compound of formula III includes those in which $R_a$, $R_b$, $R_c$, $R_d$ and $R_e$ are independently phenyl or naphthyl, optionally substituted with 1 to 3 groups selected from the group consisting of halo, optionally substituted lower alkyl (such as halo-substituted lower alkyl, e.g. trifluoromethyl), optionally substituted alkoxyl (e.g. such as halo-substituted lower alkoxyl, e.g. trifluoromethyl) and optionally substituted aryloxy (e.g. cyano-substituted phenoxy).

In certain examples, the compound of formula III is one of the compounds SC-36, SC-37 and SC-38, as listed in Table 3.

TABLE 3

| Cpd | $R_7$ |
|---|---|
| SC-36 | (3-OCF$_3$-benzyl)amino group |
| SC-37 | (3-CF$_3$-phenylsulfonyl)amino group |
| SC-38 | phenylsulfonyl amino group |

The term "halo" or "halogen" alone or in combination means all halogens, such as fluorine (F), chlorine (Cl), bromine (Br) or iodine (I).

The term "hydroxyl" refers to the group —OH.

The terms "thio" and "mercapto" are used interchangeably and refer to the group -SH."

The term "alkyl" alone or in combination refers to an alkane-derived radical containing, unless otherwise stated, 1-20 carbon atoms ($C_1$-$C_{20}$), preferably 1-15 carbon atoms ($C_1$-$C_{15}$), more preferably 1-10 carbon atoms ($C_1$-$C_{10}$). It is a straight chain alkyl, branched alkyl or cycloalkyl, preferably, straight or branched alkyl groups containing from 1-15, more preferably 1 to 8 even more preferably 1-6, yet more preferably 1-4 and most preferably 1-2, carbon atoms, such as methyl, ethyl, propyl, isopropyl, butyl, t-butyl and the like. The term "lower alkyl" is used herein to describe the straight chain alkyl groups as described above. Preferably, cycloalkyl groups are monocyclic, bicyclic or tricyclic ring systems of 3-8, more preferably 3-6, ring members per ring, such as cyclopropyl, cyclopentyl, cyclohexyl, adamantyl and the like. Alkyl also includes a straight chain or branched alkyl group that contains or is interrupted by a cycloalkyl portion. The straight chain or branched alkyl group is attached at any available point to produce a stable compound. Examples of this include, but are not limited to, 4-(isopropyl)-cyclohexylene or 2-methyl-cyclopropylpentyl. A substituted with 1 to 3 groups or substituents of halo, hydroxyl, alkoxy, alkythio, alkylsulfinyl, alkylsylfinyl, acyloxy, aryloxy, heteroaryloxy, amine optionally mono- or disubstituted with alkyl, aryl or heteroaryl groups, amidino, urea optionally substituted with alkyl, aryl, heteroaryl or heterocyclyl groups, aminosulfinyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like.

The term "alkenyl" alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon double bind. In the case of a cycloalkenyl group, conjugation of more than one carbon to carbon double bond is not such as to confer aromaticity to the ring. Carbon to carbon double bonds may be either contained within a cycloalkyl portion, with the exception of cyclopropyl, or within a straight chain or branched portion. Examples of alkenyl groups include ethenyl, propenyl, ispropnyl, butenyl, cyclohexenyl, cyclohexenylalkyl and the like. A substituted alkenyl is the straight chain alkenyl, branched alkenyl or cycloalkenyl groups defined previously, independently substituted with 1 to 3 groups or substituents of halo, hydroxyl, aryloxy, alkylthio, alkylsulfinyl, alkylsulfonyl, independently substituted with alkyl, aryl or heteroaryl groups, amidino, urea optionally substituted with alkyl, aryl, heteroaryl or heterocycloyl groups, aminosulfonyl optionally N-mono- or N, N-di-substituted with alkyl, aryl or heteroaryl groups, alkylsulfonylamino, alkylcarbonylamino, arylcarbinylamino, aryloxycarbonyl, heteroaryloxycarbonyl, or the like attached at any available point to produce a stable compound.

The term "alkynyl" alone or in combination means a straight, branched, or cyclic hydrocarbon containing 2-20, preferably 2-17, more preferably 2-10, even more preferably 2-8, most preferably 2-4, carbon atoms and at least one, preferably 1-3, more preferably 1-2, most preferably one, carbon to carbon triple bond. Examples of alkynyl groups include ethynyl, propynyl, isopropynyl, butynyl, and the like. A substituted alkynyl is the straight chain alkynyl, branched alkynyl groups defined previously, independently substituted with 1 to 3 groups or substituents of halo, hydroxyl, aryloxy, alkylthio, alkylsulfinyl, alkylsulfonyl, independently substituted with alkyl, aryl or heteroaryl groups, amidino, urea optionally substituted with alkyl, aryl, heteroaryl or heterocycloyl groups, aminosulfonyl optionally N-mono- or N, N-di-substituted with alkyl, aryl or heteroaryl groups, alkylsulfonylamino, alkylcarbonylamino, arylcarbinylamino, aryloxycarbonyl, heteroaryloxycarbonyl, or the like attached at any available point to produce a stable compound.

The term "alkyl alkenyl' refers to a group-R—CR'=CR"R"', where R is lower alkyl, or substituted lower alkyl, R', R", R"' may independently be hydrogen, halogen, lower, alkyl, substituted lower alkyl, acyl, aryl, substituted aryl, hetaryl, or substituted hetaryl as defined below.

The term "alkyl alkynyl' refers to a group-R—CCR', where R is lower alkyl, or substituted lower alkyl, R' is hydrogen, halogen, lower, alkyl, substituted lower alkyl, acyl, aryl, substituted aryl, hetaryl, or substituted hetaryl as defined below.

The term "alkoxy" denotes the group —OR, where R is lower alkyl, substituted lower alkyl, acyl, aryl, substituted aryl, arakyl, substituted arakyl, heteroalkyl, heteroarylalkyl, cycloalkyl, substituted cycloalkyl, cycloheteroalkyl, or substituted cycloheteroalkyl as definded.

The term "alkylthio" or "thioalkoxy" denotes the group-SR, $S(O)_{n=1-2}$—R, where R is lower alkyl, substituted lower alkyl, acyl, aryl, substituted aryl, arakyl, or substituted arakyl as defined herein.

The term "acyl" denotes groups-C(O)R, where R is hydrogen, lower alkyl, substituted lower alkyl, aryl, substituted aryl, and the like as defined herein.

The term "aryloxy' denotes groups-OAr, where Ar is an aryl, substituted aryl, heteroaryl, or substituted heteroaryl group as defined herein.

The term "amido" denoteds the group-C(O)NRR', where R and R' may independently by hydrogen, lower alkyl, substituted lower alkyl, aryl, substituted aryl, and the like as defined herein.

The term "carboxyl" denoteds the group-C(O)OR, where R is hydrogen, lower alkyl, substituted lower alkyl, aryl, substituted aryl, and the like as defined herein.

The term "aryl" alone or in combination means phenyl or napthyl optionally carbocyclic fused with a cycloalkyl of preferably 5-7, more preferably 5-6, ring members and/or optionally substituted with 1 to 3 groups or substituents of halo, hydroxyl, aryloxy, alkylthio, alkylsulfinyl, alkylsulfonyl, independently substituted with alkyl, aryl or heteroaryl groups, amidino, urea optionally substituted with alkyl, aryl, heteroaryl or heterocycloyl groups, aminosulfonyl optionally N-mono- or N, N-di-substituted with alkyl, aryl or heteroaryl groups, alkylsulfonylamino, alkylcarbonylamino, arylcarbinylamino, aryloxycarbonyl, heteroaryloxycarbonyl, or the like.

The term "heterocycle" refers to a saturated, unsaturated, or aromatic carbocyclic group having a single ring (e.g., morpholino, pyridyl or furyl) or multiple condensed rings (e.g., naphthpyridyl, quinoxaryl, quinolinyl, indolizinyl or benzo[b]thienyl) and having at least one hetero atom, such as N, O or S, within the ring, which can optionally be unsubstituted or substituted with, e.g., halogen, lower alkyl, lower alkoxy, alkylthiol, acetylene, amino, amido, carboxyl, hydroxyl, aryl, aryloxy, heterocycle, hetaryl, substituted hetaryl, nitro, cyano, thiol, sulfamino and the like.

The term "heteroaryl" alone or in combinations means a monocyclic aromatic ring structure containing 5 or 6 ring atoms, or a bicyclic aromatic group having 8 to 10 atoms, containing one or more, preferably 1-4, more preferably 1-3, even more preferably 1-2, heteroatoms independently selected from the group O, S, and N, and optionally substituted with 1 to 3 groups or substituents of halo, hydroxyl, alkoxy, alkythio, alkylsulfinyl, alkylsylfinyl, acyloxy, aryloxy, heteroaryloxy, amine optionally mono- or disubstituted with alkyl, aryl or heteroaryl groups, amidino, urea optionally substituted with alkyl, aryl, heteroaryl or heterocyclyl groups, aminosulfinyl optionally N-mono- or N,N-di-substituted with alkyl, aryl or heteroaryl groups, alkylsulfonylamino, arylsulfonylamino, heteroarylsulfonylamino, alkylcarbonylamino, arylcarbonylamino, heteroarylcarbonylamino, or the like. Heteroaryl is also intend to include oxidized S or N, such as sulfinyl, sulfonyl and N-oxide of a tertiary ring nitrogen. A carbon or nitrogen atom is the point of attachment of the heteroaryl ring structure such that a stable aromatic ring is retained. Examples of heteroaryl groups are pyridinyl, pyridazinyl, pyrazinyl, quinazolinyl, purinyl, indonyl, quinolinyl, pyrimidinyl, pyrrolyl, oxazolyl, thiazolyl, thienyl, isoxazolyl, oxathiadiazolyl, isothiazolyl, tetrazolyl, imidazolyl, triazinyl, furanyl, benzofuryl, indolyl and the like. A substituted heteroaryl contains a substituent attached an available carbon or nitrogen to produce a stable compound.

The term "heterocyclyl" alone or in combination means a non-aromatic cyclialkyl group having from 5 to 10 atoms in which from 1 to 3 carbon atoms in the ring are replaced by heteroatoms of O, S, N, and are optionally benzo fused or fused heteroaryl of 5-6 ring members and/or are optionally substituted as in the case of cycloalkyl. Heterocyclyl is also intended to include oxidized S or N, such as sulfinyl, sulfonyl and N-oxide of a tertiary ring nitrogen. The point of attachment is at a carbon or nitrogen atom. Example of heterocyclyl group are tetrahydrofuranyl, dihydropyridinyl, piperifinyl, pyrrolidinyl, piperazinyl, dihydrobenzofuryl, dihydroindolyl, and the like. A substituted heterocyclyl contains a substituent nitrogen attached at an available carbon or nitrogen to produce a stable compound.

The term "substituted heteroaryl" refers to a heterocycle optionally mono or poly substituted with one or more functional groups, e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "arakyl" refers to the group-R—Ar where Ar is an aryl group and R is lower alkyl or substituted lower alkyl group. Aryl groups can optionally be unsubstituted or substituted with, e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "heteroalkyl" refers to the group —R-Het where Het is a heterocycle group and R is a lower alkyl group. Heteroalkyl groups can optionally be unsubstituted or substituted with halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "heteroaryalkyl" refers to the group —R-HetAR where HetAr is an heteroaryl group and R is a lower alkyl group. Heteroarylalkyl groups can optionally be unsubstituted or substituted with halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "cycloalkyl" refers to a divalent cyclic or polycyclic alkyl group containing 3 to 15 carbon atoms.

The term "substituted cycloalkyl" refers to a cycloalkyl group comprising one or more substituents with, e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "cycloheteroalkyl" refers to a cycloalkyl group wherein one or more of the ring carbon atoms is replaced with a heteroatom (e.g., N, O, S, or P).

The term "substituted cycloheteroalkyl" refers to a cycloheteroalkyl group as herein defined which contains one or more substituents, such as halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "alkyl cycloalkyl" denoted the group-R'-cycloalkyl where cycloalkyl is a cycloalkyl group and R is a lower alkyl or substituted lower alkyl. Cycloalkyl groups can optionally be unsubstituted or substituted with e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The term "alkyl cycloheteroalkyl" denoted the group-R'-cycloheteroalkyl where R is a lower alkyl or substituted lower alkyl. Cycloheteroalkyl groups can optionally be unsubstituted or substituted with e.g., halogen, lower alkyl, lower alkoxy, alkylthio acetylene, amino, amido, carboxyl, hydroxyl, aryl, aryloxy, heterocycle, substituted heterocycle, hetaryl, substituted hetaryl, nitro, cyano, thiol, sulfamido and the like.

The compounds of the invention can be prepared by conventional chemical procedure such as those described in advances organic chemistry written by Francis Carey and Richard Sundberg and review journal "Account of Chemical research."

Particularly, the procedure shown in the general scheme as below exemplifies synthesis of certain compounds of the invention.

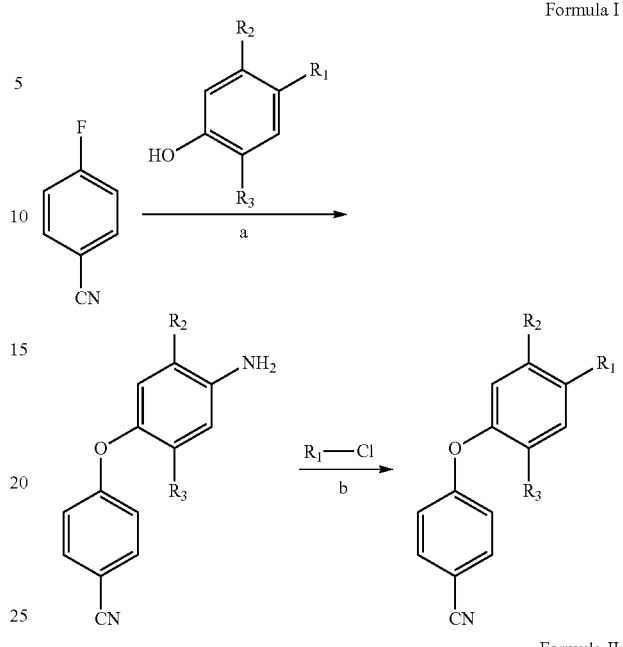

Formula I

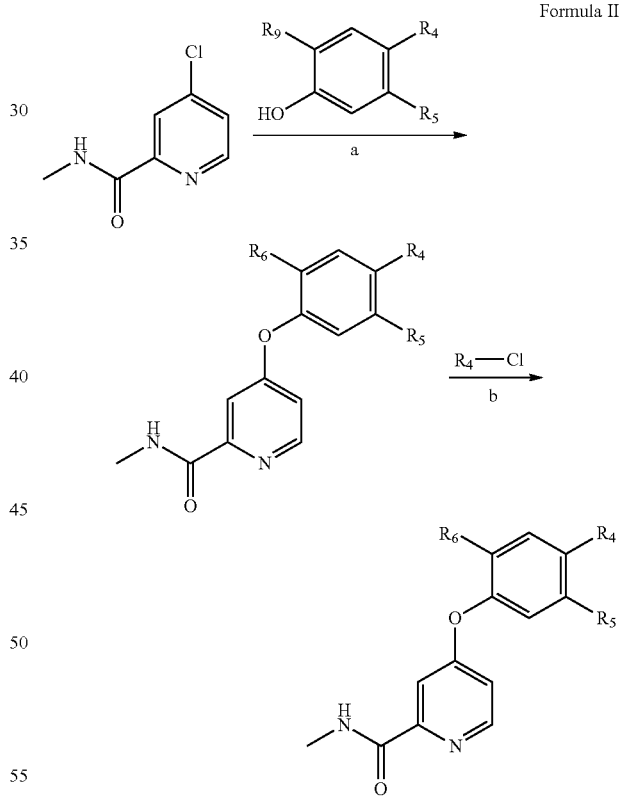

Formula II

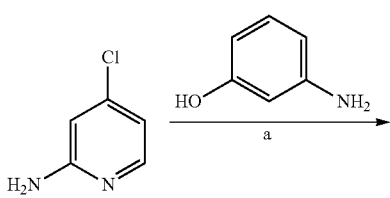

Formula III

-continued

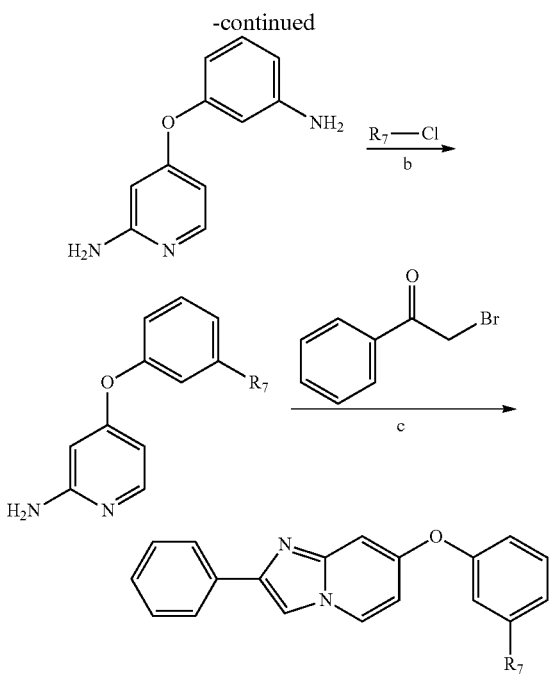

General synthetic procedure for Formula I, II, III: a, K₂CO₃, DMF; b, pyridine, THF; c. Et₃N, dioxane The compounds of the invention thus synthesized can be further purified by chromatography or crystallization or any other proer method known in the art.

The present invention also provides a pharmaceutical composition comprising one or more of the above-described compounds and a pharmaceutically acceptable carrier. The pharmaceutical composition of the invention may be used for increasing expression levels or biological activity of SHP-1 in a cell, or treating a disease or condition characterized by decreased expression levels or biological activity of SHP-1. Also within the scope of this invention is the use of any of the above-described compounds for increasing expression levels or biological activity of SHP-1 in a cell, or treating a disease or condition characterized by decreased expression levels or biological activity of SHP-1 as described herein and for the manufacture of a medicament for treating the same.

The present invention also provides a method for increasing SHP-1 expression levels or biological activity in a cell, comprising contacting the cell with an effective amount of a compound or a pharmaceutical composition as described herein. Further provided is a method for treating a disease or condition characterized by decreased expression levels or biological activity of SHP-1 in a subject in need thereof, comprising administering to the subject an effective amount of a compound or a pharmaceutical composition as described herein.

The term "treating" or "treatment" includes prophylaxis of the specific disorder or condition, or alleviation of the symptoms associated with a specific disorder or condition and/or preventing or eliminating said symptoms.

The compounds of the present invention can be used for the treatment of diseases or conditions characterized by decreased expression levels or biological activity of SHP-1. A compound of the invention can be administered to a human patient by itself or in pharmaceutical compositions where it is mixed with suitable carriers or excipients at doses to treat or ameliorate various conditions characterized by decreased expression levels or biological activity of SHP-1. Increased or decreased expression levels or biological activity of a factor (e.g. SHP-1) can be readily detected by the gene product of the factor such as a protein or RNA, in a sample from a subject (e.g. from blood or biopsy tissue) and assaying it in vitro for RNA levels, structure and/or activity of the expressed proteins and the like, using detection methods known in the art such as enzyme-linked immunosorbent assay (ELISA), Western blotting and Northern blotting. Particular examples of the diseases or conditions characterized by decreased expression levels or biological activity of SHP-1 according to the invention include, but are not limited to, cancer (e.g. hepatocellular carcinoma, leukemia, lung cancer, breast cancer, renal cancer, and osteoporosis.

A "subject" is particularly a mammal, such as a human, but can also be a companion animal (e.g., dogs, cats, and the like), farm animals (e.g., cows, sheep, pigs, horses, and the like) or laboratory animals (e.g., rats, mice, guinea pigs, and the like) in need of the treatment as described herein.

"An effective amount" as used herein refers to the amount of an active agent required to confer therapeutic effects on a subject, either alone or in combination with one or more other active agents. Effective amounts vary, as recognized by those skilled in the art, depending on route of administration, excipient usage, and co-usage with other active agents.

Suitable routes of administration may, for example, include oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections, and optionally in a depot or sustained release formulation.

The pharmaceutical compositions of the present invention may be manufactured in a manner known in the art, e.g., by means of conventional mixing, dissolving, emulsifying, encapsulating, entrapping, or lyophilizing processes. Pharmaceutical compositions for use in accordance with the present invention thus may be formulated in conventional manner using one or more physiologically acceptable carriers comprising excipients and/or auxiliaries that facilitate processing of the active compounds into preparations, which can be used pharmaceutically. As used herein, "acceptable" means that the carrier must be compatible with the active ingredient of the composition (and preferably, capable of stabilizing the active ingredient) and not deleterious to the subject to be treated. Proper formulation is dependent upon the route of administration chosen.

In particular, for injection, the compounds of the invention may be formulated in, for example, physiologically compatible buffers, such as Hank's solution, Ringer's solution, or physiological saline buffer. For oral administration, the compounds of the invention may be formulated by combining the active compounds with pharmaceutically acceptable carriers known in this art, such as lactose, sucrose, mannitol, sorbitol, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), to enable the compounds of the invention to be formulated as tablets, pills, dragees, capsules, liquids, gels, syrups, slurries, suspensions and the like. For administration by inhalation, the compounds of the invention can be formulated in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas.

Without further elaboration, it is believed that the above description has adequately enabled the present invention. The following specific example is, therefore, to be construed as merely illustrative, and not limitative of the remainder of the disclosure in any way whatsoever. All of the publications, including patents, cited herein are hereby incorporated by reference in their entireties.

EXAMPLE 1

Chemical Synthesis 1.1 Materials

Proton nuclear magnetic resonance ($^1$H-NMR) spectra were recorded on Bruker DPX300 (400 MHz) instruments. Chemical shifts are reported as values (ppm) downfield from internal deuterated Chloroform of the indicated organic solution. Peak multiplicities are expressed as follows: s, singlet; d, doublet; t, triplet; q, quartet; dd, doublet of doublet; ddd, doublet of doublet of doublets; dt, doublet of triplet; brs, broad singlet; m, multiplet. Coupling constants (J values) are given in hertz (Hz). Reaction progress was determined by thin layer chromatography (TLC) analysis on silica gel 60 F254 plate (Merck). Chromatographic purification was carried on silica gel columns 60 (0.063-0.200 mm or 0.040-0.063 mm, Merck), basic silica gel. Commercial reagents and solvents were used without additional purification. Abbreviations are used as follows: CDCl$_3$, deuterated chloroform; DMSO-d6, dimethyl sulfoxide-d6; EtOAc, ethyl acetate; DMF, N,N-dimethylformamide; MeOH, methanol; THF, tetrahydrofuran; EtOH, ethanol; DMSO, dimethyl sulfoxide; NMP, N-methylpyrrolidone. High resolution mass spectra were recorded on a FINNIGAN MAT 95S mass spectrometer.

1.2 Methods

Figure 1:
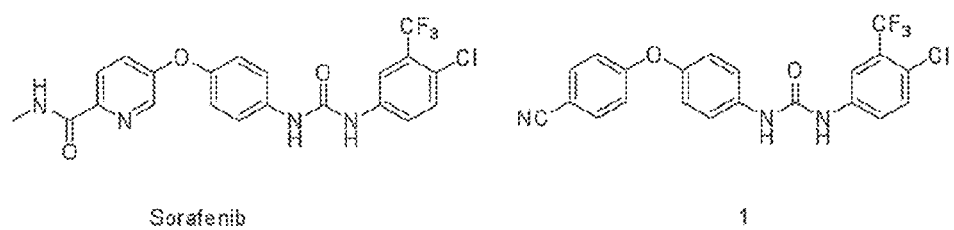
FIG. 1 shows the chemical structure of sorafenib and compound SC-1.
Figure 2:
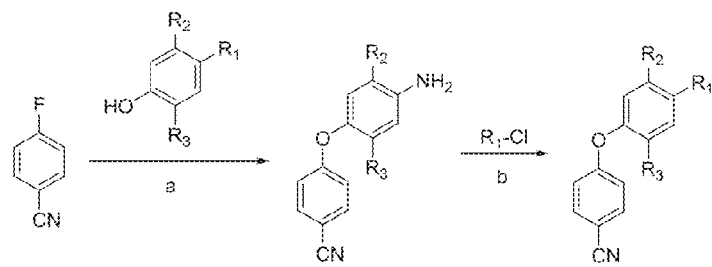
FIG. 2 shows the general synthetic procedure for formulae I, II and III of the invention.
Figure 2:
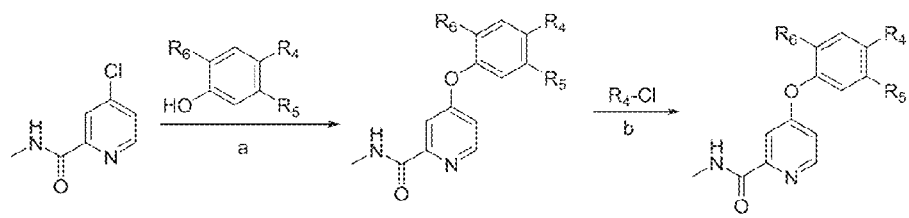
Figure 2:
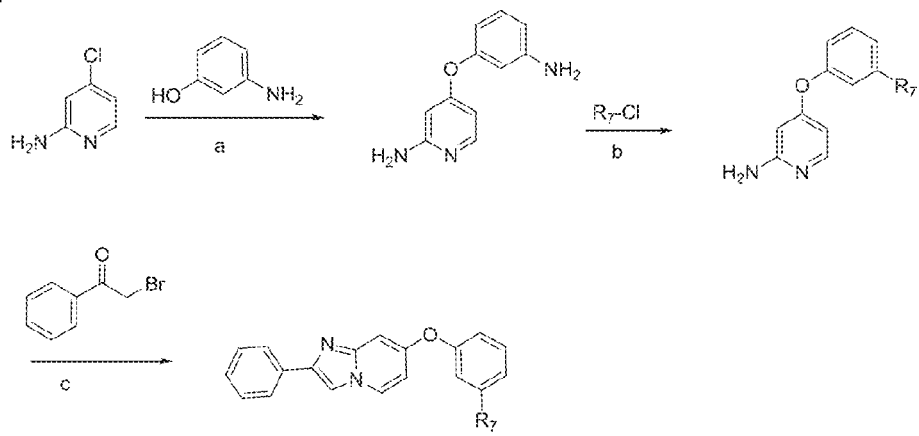

The structural design of the compounds of the invention is described below. First, to address the relationship between Raf kinase repression and downregulation of P-STAT3 by sorafenib, we used a chemical approach to reduce the hydrogen bonding interaction between the amide group of sorafenib with Raf by replacing amido group by a phenylcyano group (compound 1, FIG. 1). We also modified SC-1 based on functional groups which contain different size, hydrogen donor, hydrogen acceptor, hydrophobic and hydrophilic ability to generate a series of compounds SC-48, SC-49, SC-54, SC-55, SC-56, SC-58, SC-43, SC-44, SC-45, SC-50, SC-51, SC-52, SC-59, SC-60 and SC-40. In addition, we replaced the urea functional group in the sorafenib backbone with various amide and sulfonamide yielding compounds 2-11. Further, we replaced the pyridine ring with quinoline and used it as a platform to carry out structural modification, generating a series of compounds 12-19 and 20-25. These SC-1 derivatives were synthesized according to a general procedure described above in formula II FIG. 2. Moreover, we extend the length of compound by adding one phenyl ring to explore the structure activity relationship with different functional group 36-38.

1.2.1 Synthesis Procedures for Compound 1 (Formula I)

To a 50 mL THF solution of triphosgen (0.30 g, 1.0 mmol), 4-chloro-3-(trifluoromethyl)aniline (0.21 g, 1.1 mmol) and 2 equivalent of triethyl amine were added. The mixture was heated to 50° C. for 30 min After the temperature was back to room temperature, 4-(4-aminophenoxyl)benzonitrile in the 10 mL THF solution was added to the mixture and heated to 50° C. for another 30 min. The mixture was evaporated, diluted with water and extracted with EtOAc. The extract was washed with brine, dried over anhydrous magnesium sulfate, and concentrated under reduced pressure to give 1. (0.34 g, 80%)

1.2.1.1.

1-(4-Chloro-3-(trifluoromethyl)phenyl)-3-(4-(4-cyanophenoxyl)phenyl)urea (1)

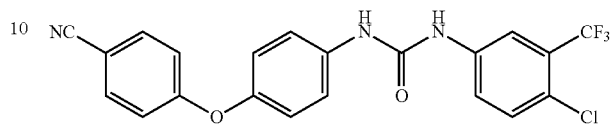

SC-1

$^1$H NMR (400 MHz, CDCl$_3$): δ 9.17 (s, 1H), 8.94 (s, 1H), 8.10 (s, 1H), 7.81 (d, 2H, J=6.8), 7.63-7.59 (m, 2H), 7.54 (d, 2H, J=7.2 Hz), 7.10 (d, 2H, J=6.8 Hz), 7.05 (d, 2H, J=7.2 Hz); $^{13}$C NMR (100 MHz, methanol-d$_4$): δ 163.7, 163.6, 154.8, 151.4, 151.2, 140.1, 137.7, 137.4, 135.3, 132.9, 129.7, 129.4, 129.1, 128.8, 128.3, 125.6, 125.5, 125.4, 124.2, 122.9, 122.4, 122.3, 122.1, 120.2, 119.7, 118.8, 118.7, 118.6, 118.6, 106.5, 106.4; HRMS calculated for C$_{21}$H$_{13}$ClF$_3$N$_3$O$_2$ (M+H): 431.0648. Found: 431.0656.

1.2.1.2.

1-(3-(4-cyanophenoxyl)phenyl)-3-(4-chloro-3-(trifluoromethyl)phenyl)urea (43)

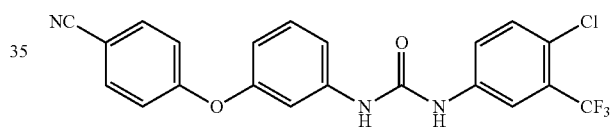

43

$^1$H NMR (400 MHz, DMSO): δ 9.17 (s, 1H), 9.03 (s, 1H), 8.04 (d, J=2.4 Hz, 1H), 7.83 (d, J=8.8 Hz, 2H), 7.64-7.55 (m, 2H), 7.41-7.32 (m, 2H), 7.23 (d, J=7.2 Hz, 1H), 7.11 (d, J=8.0 Hz, 2H), 6.75 (dd, J=8.0 Hz, 2.4 Hz, 1H); HRMS calculated for C$_{21}$H$_{12}$N$_3$O$_2$F$_3$Cl [M−H]$^−$: 430.0570. Found: 430.0576.

1.2.1.3.

4-(3-(3-(trifluoromethyl)benzen-sulfonylamino)phenoxy)benzonitrile (44)

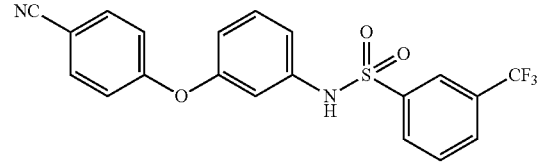

44

$^1$H NMR (400 MHz, CDCl$_3$): δ 8.00 (s, 1H), 7.96 (d, J=8.0 Hz, 1H), 7.81 (d, J=8.0 Hz, 1H), 7.65-7.54 (m, 3H), 7.26 (t, J=8.0 Hz, 1H), 7.08 (s, 1H), 7.05-6.97 (m, 1H), 6.94-6.86 (m, 3H), 6.84 (t, J=2.0 Hz, 1H), 6.81 (dd, J=8.4 Hz, 2.0 Hz, 1H); HRMS calculated for C$_{20}$H$_{12}$N$_2$O$_3$F$_3$S [M−H]$^−$: 417.0521. Found: 417.0518.

1.2.1.4.

4-(3-(3-(trifluoromethoxy)benzylamino)phenoxy)benzonitrile (45)

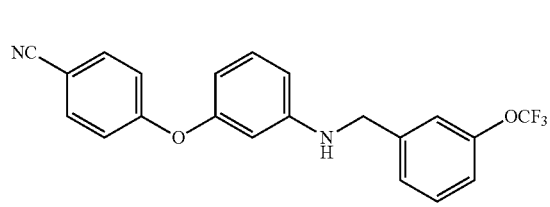

¹H NMR (400 MHz, CDCl₃): δ 7.61 (d, J=8.8 Hz, 2H), 7.43 (t, J=8.0 Hz, 1H), 7.33 (d, J=8.4 Hz, 1H), 7.29-7.16 (m, 3H), 7.04 (d, J=8.8 Hz, 2H), 6.55 (dd, J=8.0 Hz, 2.4 Hz, 1H), 6.46 (dd, J=8.0 Hz, 2.0 Hz, 1H), 6.34 (t, J=2.4 Hz, 1H), 4.41 (s, 2H); HRMS calculated for $C_{21}H_{16}N_2O_2F_3$ [M+H]⁺: 385.1164. Found: 385.1157.

1.2.1.5.

1-(4-(4-cyanophenoxyl)phenyl)-3-(3,4-dimethoxybenzyl)urea (48)

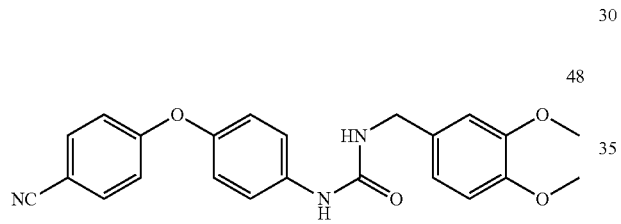

¹H NMR (400 MHz, CDCl3): δ 7.56 (d, J=6.8 Hz, 2H), 7.34 (d, J=8.8 Hz, 2H), 6.98-6.94 (m, 4H), 6.88-6.75 (m, 4H), 6.56 (brs, 1H), 4.36 (s, 2H), 3.84 (s, 6H); HRMS calculated for $C_{23}H_{20}N_3O_4$ [M−H]⁻: 402.1454. Found: 402.1462.

1.2.1.6.

1-(4-chloro-3-(trifluoromethyl)phenyl)-3-(4-(4-cyanophenoxyl)benzyl)urea (49)

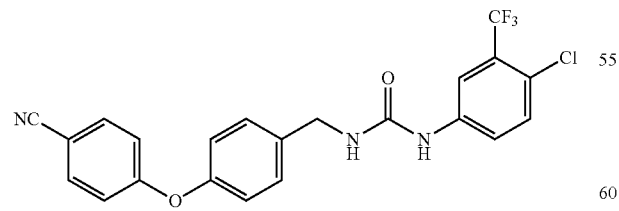

¹H NMR (400 MHz, CDCl₃): δ 7.76 Hz (s, 1H), 7.51-7.39 (m, 3H), 7.29 (dd, J=8.8 Hz, 2.4 Hz, 1H), 7.13 (d, J=8.4 Hz, 3H), 6.83 (dd, J=8.8 Hz, 4.8 Hz, 4H), 5.93 (t, J=6.0 Hz, 1H), 4.24 (d, J=6.0 Hz, 2H); HRMS calculated for $C_{22}H_{14}N_3O_2F_3Cl$ [M−H]⁻: 444.0727. Found: 444.0732.

1.2.1.7.

1-(3-(4-cyanophenoxyl)phenyl)-3-(3-fluorophenyl)urea (50)

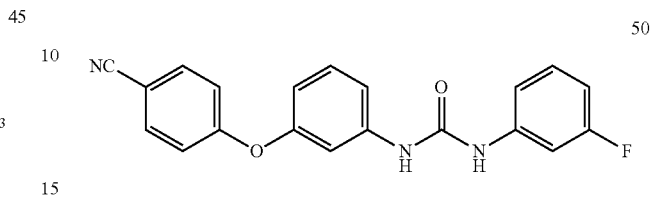

¹H NMR (400 MHz, MeOD): δ 7.66 (d, J=9.2 Hz, 2H), 7.60 (s, 1H), 7.41-7.34 (m, 2H), 7.22 (q, J=8.0 Hz, 1H), 7.18 (dd, J=8.0 Hz, 2.0 Hz, 1H), 7.10-7.02 (m, 3H), 6.71 (dd, J=8.8 Hz, 2.4 Hz, 2H); HRMS calculated for $C_{20}H_{13}N_3O_2$ [M−H]⁻: 346.0992. Found: 346.0999.

1.2.1.8.

N-(3-(4-cyanophenoxyl)phenyl)benzamide (51)

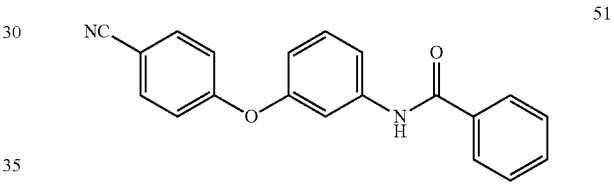

¹H NMR (400 MHz, CDCl₃): δ 8.82 (s, 1H), 7.75 (d, J=7.6 Hz, 2H), 7.53 (s, 1H), 7.46-7.35 (m, 4H), 7.28 (t, J=8.0 Hz, 2H), 7.22 (t, J=8.0 Hz, 1H), 6.90 (d, J=8.8 Hz, 2H), 6.72 (dd, J=8.0 Hz, 2.0 Hz, 1H); HRMS calculated for $C_{20}H_{13}N_2O_2$ [M−H]⁻: 313.0977. Found: 313.0971.

1.2.1.9.

N-(3-(4-cyanophenoxyl)phenyl)benzenesulfonamide (52)

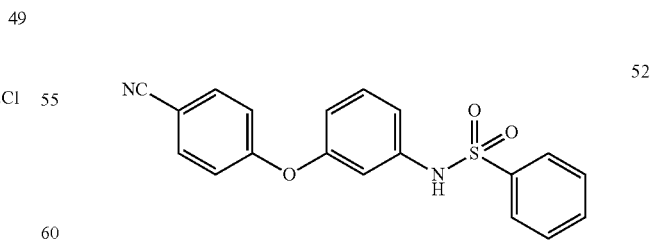

¹H NMR (400 MHz, CDCl₃): δ 7.79 (d, J=8.4 Hz, 2H), 7.53 (t, J=4.4 Hz, 3H), 7.42 (t, J=8.0 Hz, 2H), 7.20 (t, J=8.0 Hz, 1H), 6.93 (dd, J=8.0 Hz, 2.0 Hz, 1H), 6.86-6.83 (m, 3H), 6.73 (dd, J=8.0 Hz, 2.0 Hz, 1H); HRMS calculated for $C_{19}H_{13}N_2O_3S$ [M−H]⁻: 349.0647. Found: 2349.0643.

1.2.1.10.

1-(4-(4-cyanophenoxyl)benzyl)-3-(3,4-dimethoxybenzyl)urea (54)

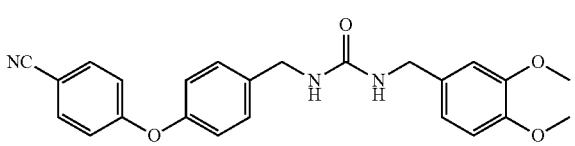

54

¹H NMR (400 MHz, DMSO): δ 7.81 (d, J=9.2 Hz, 2H), 7.33 (d, J=8.4 Hz, 2H), 7.06 (dd, J=15.6 Hz, 9.2 Hz, 4H), 6.86 (d, J=9.2 Hz, 2H), 6.76 (dd, J=8.0 Hz, 2.0 Hz, 1H), 6.45 (t, J=6.0 Hz, 1H), 6.38 (t, J=6.0 Hz, 1H), 4.23 (d, J=5.2 Hz, 2H), 4.14 (d, J=5.2 Hz, 2H), 3.69 (s, 6H); HRMS calculated for $C_{24}H_{24}N_3O_4$ [M+H]⁺: 418.1767. Found: 418.1773.

1.2.1.11.

1-(4-(4-cyanophenoxyl)benzyl)-3-(3-(trifluoromethoxy)benzyl)urea (55)

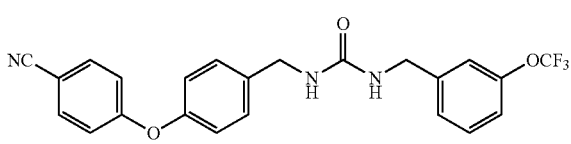

55

¹H NMR (400 MHz, CDCl₃): δ 7.49 (d, J=9.2 Hz, 2H), 7.17 (t, J=8.0 Hz, 1H), 7.10 (d, J=8.4 Hz, 2H), 7.00-6.92 (m, 3H), 6.88 (d, J=9.2 Hz, 2H), 6.84 (d, J=8.4 Hz, 2H), 6.17-6.05 (m, 2H), 4.10 (m, 4H); HRMS calculated for $C_{23}H_{19}N_3O_3F_3$ [M+H]⁺: 442.1379. Found: 442.1381.

1.2.1.12.

(R)-1-(4-(4-cyanophenoxyl)phenyl)-3-(1-(naphthalen-1-yl)ethyl)urea (56)

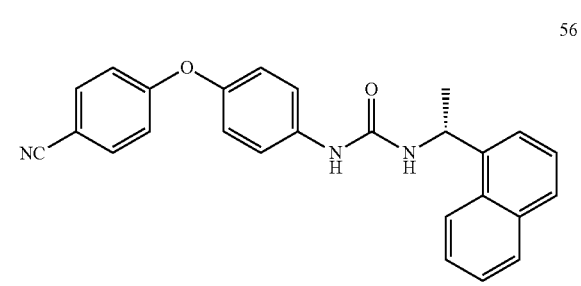 [SMILES: C[C@@H](NC(=O)Nc1ccc(Oc2ccc(C#N)cc2)cc1)c1cccc2ccccc12]

56

¹H NMR (400 MHz, MeOD): δ 8.17 (d, J=8.0 Hz, 1H), 7.87 (d, J=8.0 Hz, 1H), 7.78 (d, J=8.0 Hz, 1H), 7.65 (d, J=8.8 Hz, 2H), 7.58 (d, J=7.2 Hz, 1H), 7.53 (d, J=7.2 Hz, 1H), 7.50-7.45 (m, 2H), 7.41 (d, J=8.8 Hz, 2H), 6.99 (t, J=9.2 Hz, 4H), 5.74 (d, J=6.8 Hz, 1H), 1.63 (d, J=6.8 Hz, 3H); HRMS calculated for $C_{26}H_{20}N_3O_2$ [M-H]⁻: 406.1556. Found: 406.1563.

1.2.1.13.

1-(4-chloro-3-(trifluoromethyl)benzyl)-3-(4-(4-cyanophenoxy)phenyl)urea (58)

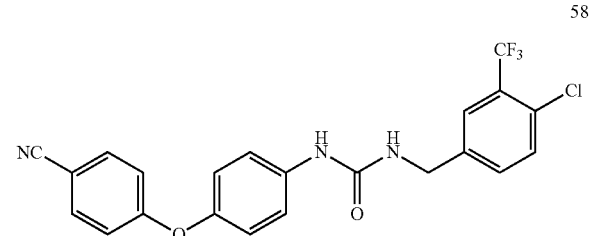

58

¹H NMR (400 MHz, MeOD): δ 7.74 (brs, 1H), 7.66 (d, J=9.2 Hz, 2H), 7.56 (d, J=2.0 Hz, 2H), 7.44 (d, J=9.2 Hz, 2H), 7.05-6.98 (m, 4H), 4.43 (s, 2H); HRMS calculated for $C_{22}H_{14}N_3O_2F_3Cl$ [M-H]⁻: 444.0727. Found: 444.0736.

1.2.1.14.

1-(4-chloro-3-(trifluoromethyl)phenyl)-3-(3-(4-cyanophenoxy)-4-methylphenyl) urea (59)

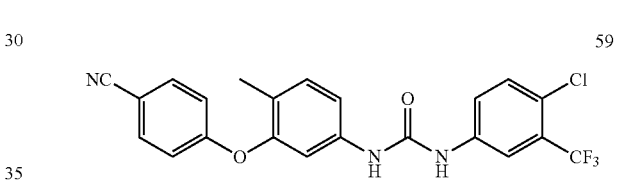

59

¹H NMR (400 MHz, MeOD): δ 7.87 (d, J=2.8 Hz, 1H), 7.60 (d, J=9.2 Hz, 2H), 7.54 (dd, J=8.4 Hz, 2.4 Hz, 1H), 7.39 (d, J=8.8 Hz, 1H), 7.25 (d, J=2.4 Hz, 1H), 7.18 (d, J=8.0 Hz, 1H), 7.12 (dd, J=8.0 Hz, 2.4 Hz, 1H), 6.93 (d, J=9.6 Hz, 2H), 2.02 (s, 3H); HRMS calculated for $C_{22}H_{14}N_3O_2F_3Cl$ [M-H]⁻: 444.0727. Found: 444.0725.

1.2.1.15.

1,3-bis(3-(4-cyanophenoxy)-4-methylphenyl)urea (60)

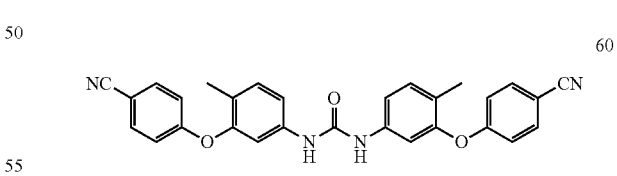

60

¹H NMR (400 MHz, DMSO): δ 8.77 (s, 2H), 7.80 (d, J=8.0 Hz, 4H), 7.29 (s, 2H), 7.24 (d, J=8.0 Hz, 2H), 7.13 (d, J=8.4 Hz, 2H), 6.98 (d, J=8.4 Hz, 4H), 2.02 (s, 6H); HRMS calculated for $C_{29}H_{21}N_4O_3$ [M-H]⁻: 473.1614. Found: 473.1619.

1.2.2 General Procedures for Compound 2-25

In a 25 mL two-necked round flask, aniline derivatives (1 mmol) and catalytic amount of pyridine were placed in anhydrous THF (10 mL) at room temperature. Acyl chloride or sulfonyl chloride compounds were added to the mixture and stirred for 2 h at room temperature. The solvent was removed under vacuum and the crude residue purified by chromatography on a silica gel column using EtOAc/Hexane as eluent (1/10 to 1/2). This procedure afforded the expected coupling product as a white solid from 70% to 95% yield.

1.2.2.1.

N-Methyl-4-(4-(phenylsulfonamido)phenoxy)picolinamide (2)

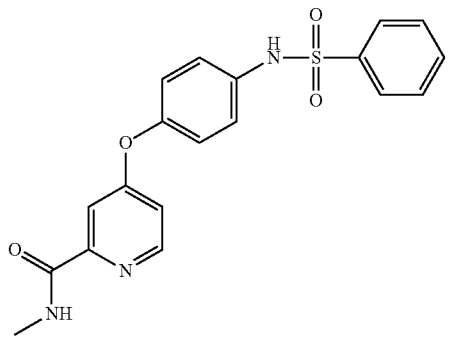 [SMILES: CNC(=O)c1cc(Oc2ccc(NS(=O)(=O)c3ccccc3)cc2)ccn1]

$^1$H NMR (400 MHz, CDCl$_3$): δ 8.36 (d, 1H, J=5.6 Hz), 8.01 (brs, 1H), 7.76 (d, 2H, J=7.6 Hz), 7.59 (s, 1H), 7.54 (t, 1H, J=8.0 Hz), 7.46 (t, 2H, J=8.0 Hz), 7.12 (d, 2H, J=8.8 Hz), 6.94 (d, 2H, J=8.8 Hz), 6.92-6.90 (m, 1H), 3.00 (d, 3H, J=5.2 Hz); $^{13}$C NMR (100 MHz, CDCl$_3$): δ 166.0, 164.6, 152.1, 151.0, 149.7, 138.9, 134.2, 133.0, 129.0, 127.1, 123.9, 121.6, 114.3, 109.9, 26.1; HRMS calculated for C$_{19}$H$_{17}$N$_3$O$_4$S (M+H): 383.0940. Found: 383.0941.

1.2.2.2.

N-Methyl-4-(4-(4-nitrophenylsulfonamido)phenoxy)picolinamide (3)

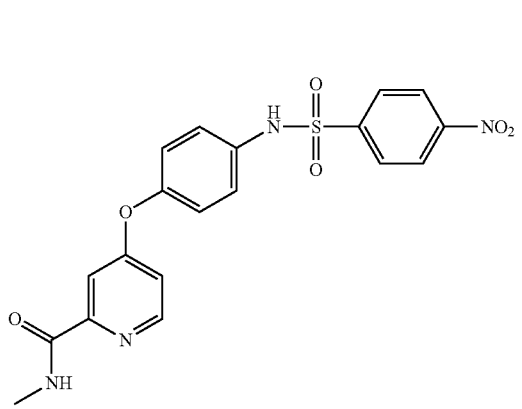 [SMILES: CNC(=O)c1cc(Oc2ccc(NS(=O)(=O)c3ccc([N+](=O)[O-])cc3)cc2)ccn1]

$^1$H NMR (400 MHz, CDCl$_3$): δ 8.39 (d, 1H, J=5.6 Hz), 8.30 (d, 2H, J=8.8 Hz), 8.07 (brs, 1H), 7.93 (d, 2H, J=8.8 Hz), 7.49 (s, 1H), 7.17 (d, 2H, J=8.8 Hz), 7.01-6.98 (m, 3H), 3.00 (d, 3H, J=5.2 Hz); HRMS calculated for C$_{19}$H$_{16}$N$_4$O$_6$S (M+H): 428.0791. Found: 428.0798.

1.2.2.3.

4-(4-(4-Fluorophenylsulfonamido)phenoxy)-N-methylpicolinamide (4)

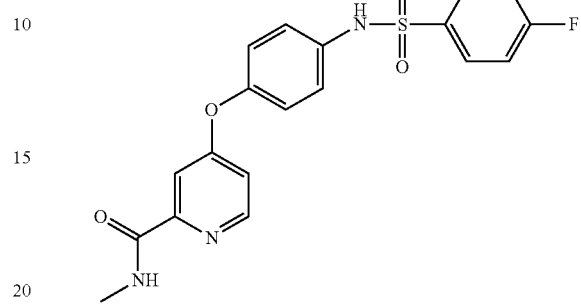

$^1$H NMR (400 MHz, CDCl$_3$): δ 8.37 (d, 1H, J=5.6 Hz), 8.00 (brs, 1H), 7.77-7.43 (m, 2H), 7.57 (s, 1H), 7.17-7.09 (m, 4H), 6.99-6.93 (m, 4H), 3.00 (d, 3H, J=4.8 Hz); NMR (100 MHz, CDCl$_3$): δ 166.5, 165.9, 164.6, 163.9, 152.1, 151.2, 149.7, 135.0, 134.0, 130.0, 129.9, 124.1, 121.7, 116.4, 116.2, 114.5, 109.8, 26.19; HRMS calculated for C$_{19}$H$_{16}$FN$_3$O$_4$S (M+H): 401.0846. Found: 401.0849.

1.2.2.4.

4-(4-(4-tert-Butylphenylsulfonamido)phenoxy)-N-methylpicolinamide (5)

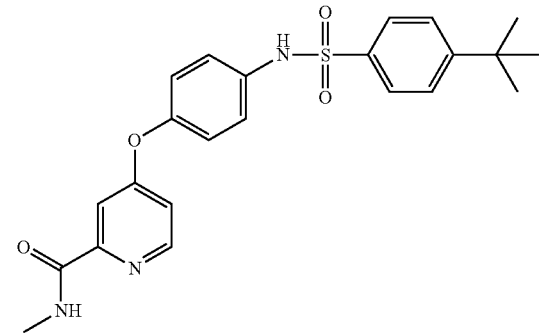 [SMILES: CNC(=O)c1cc(Oc2ccc(NS(=O)(=O)c3ccc(C(C)(C)C)cc3)cc2)ccn1]

$^1$H NMR (400 MHz, CDCl$_3$): δ 8.33 (d, 1H, J=6.0 Hz), 8.21 (brs, 1H), 7.79 (brs, 1H), 7.69 (d, 2H, J=6.8 Hz), 7.62 (s, 1H), 7.44 (d, 2H, J=6.8 Hz), 7.15 (d, 2H, J=6.8 Hz), 6.91 (s, 2H, J=6.8 Hz), 6.88-6.86 (m, 1H), 2.98 (d, 3H, J=5.2 Hz); $^{13}$C NMR (100 MHz, CDCl$_3$): δ 166.0, 164.6, 156.8, 152.2, 150.8, 149.7, 136.1, 134.4, 127.0, 126.1, 123.6, 121.6, 114.1, 110.1, 35.1, 30.1, 26.1; HRMS calculated for C$_{23}$H$_{25}$N$_3$O$_4$S (M+H): 439.1566. Found: 439.1564.

1.2.2.5.

N-Methyl-4-(4-(naphthalene-2-sulfonamido)phenoxy)picolinamide (6)

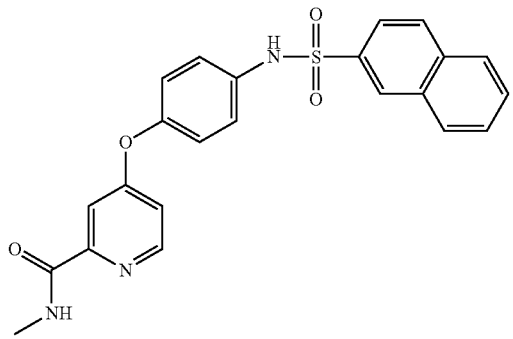 [SMILES: CNC(=O)c1cc(Oc2ccc(NS(=O)(=O)c3ccc4ccccc4c3)cc2)ccn1]

$^1$H NMR (400 MHz, CDCl$_3$): δ 8.34 (s, 1H), 8.30 (d, 1H, J=5.2 Hz), 8.05-8.02 (m, 1H), 7.89-7.83 (m, 4H), 7.74 (dd, 1H, J=8.4, 1.6 Hz), 7.60-7.52 (m, 3H), 7.16 (d, 2H, J=8.8 Hz), 6.88 (d, 2H, J=8.8 Hz), 6.84-6.82 (m, 1H); $^{13}$C NMR (100 MHz, CDCl$_3$): 165.9, 164.6, 152.1, 151.0, 149.7, 135.9, 134.9, 134.2, 132.0, 129.4, 129.3, 128.9, 128.7, 127.9, 127.5, 123.9, 122.2, 121.6, 114.2, 110.1, 26.2; HRMS calculated for C$_{23}$H$_{19}$N$_3$O$_4$S (M+H): 433.1096. Found: 433.1079.

1.2.2.6. 4-(4-(2-Bromo-4-(trifluoromethyl)phenylsulfonamido)phenoxy)-N-methylpicolinamide (7)

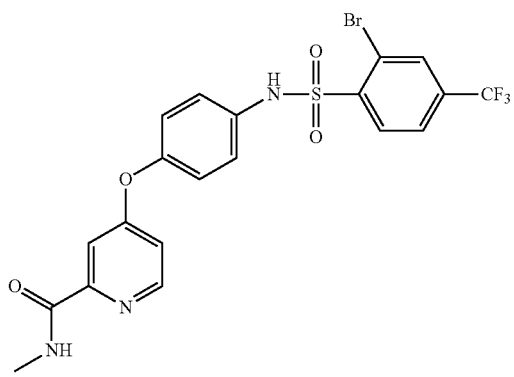 [SMILES: CNC(=O)c1cc(Oc2ccc(NS(=O)(=O)c3ccc(C(F)(F)F)cc3Br)cc2)ccn1]

$^1$H NMR (400 MHz, CDCl$_3$): δ 8.35 (d, 1H, J=5.6 Hz), 8.15 (d, 1H, J=8.0 Hz), 7.79 (brs, 1H), 7.96 (s, 1H), 7.67 (d, 2H, J=8.0 Hz), 7.57 (s, 1H), 7.18 (d, 2H, J=9.2 Hz), 6.95 (d, 2H, J=9.2 Hz), 6.90-6.88 (m, 1H), 2.98 (d, 3H, J=5.2 Hz); $^{13}$C NMR (100 MHz, CDCl$_3$): δ 165.7, 164.5, 152.2, 151.6, 149.8, 141.5, 136.1, 135.8, 135.5, 135.2, 132.7, 132.2 (m), 124.9 (m), 124.1, 123.5, 121.7, 120.8, 120.4, 114.5, 110.0, 26.1; HRMS calculated for C$_{20}$H$_{15}$BrF$_3$N$_3$O$_4$S (M+H): 528.9919. Found: 528.9917.

1.2.2.7.

N-Methyl-4-(4-(2-nitrophenylsulfonamido)phenoxy)picolinamide (8)

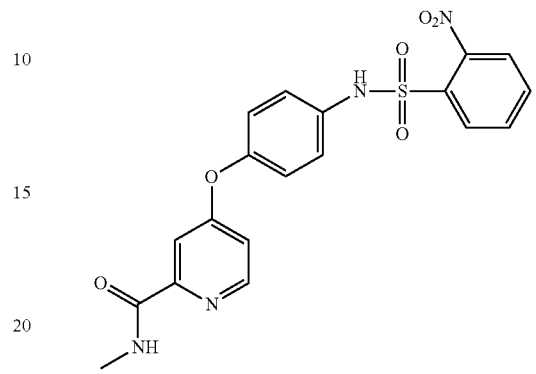

$^1$H NMR (400 MHz, CDCl$_3$): δ 8.37 (d, 1H, J=6.0 Hz), 7.98 (brs, 1H), 7.86-7.83 (m, 2H), 7.72-7.68 (m, 2H), 7.55 (s, 1H), 7.24 (d, 2H, J=8.8 Hz), 6.98 (d, 2H, J=8.8 Hz), 6.94-6.92 (m, 1H), 2.98 (d, 3H, J=4.8 Hz); HRMS calculated for C$_{19}$H$_{16}$N$_4$O$_6$S (M+H): 428.0791. Found: 428.0796.

1.2.7.8

4-(4-(3,5-Bis(trifluoromethyl)benzamido)phenoxy)-N-methylpicolinamide (9)

$^1$H NMR (400 MHz, CDCl$_3$): δ 9.92 (s, 1H), 8.40 (s, 1H), 8.33 (d, 1H, J=5.6 Hz), 8.10 (q, 1H, J=5.2 Hz), 7.90 (s, 1H), 7.71 (d, 2H, J=8.8 Hz), 7.40 (d, 1H, J=2.8 Hz), 6.99-6.97 (m, 1H), 6.93 (d, 2H, J=8.8 Hz), 2.91 (d, 3H, J=4.8 Hz); $^{13}$C NMR (100 MHz, methanol-d$_4$): δ 167.8, 166.8, 165.1, 153.4, 151.8, 151.6, 138.6, 137.6, 133.6, 133.3, 133.0, 132.6, 129.4 (d), 126.2 (m), 126.0, 124.2, 123.2, 122.4, 115.2, 110.7, 26.4; HRMS calculated for C$_{22}$H$_{15}$F$_6$N$_3$O$_3$ (M+H): 483.1018. Found: 483.1017.

1.2.2.9

4-(4-(5-Fluoro-2-(trifluoromethyl)benzamido)phenoxy)-N-methylpicolinamide (10)

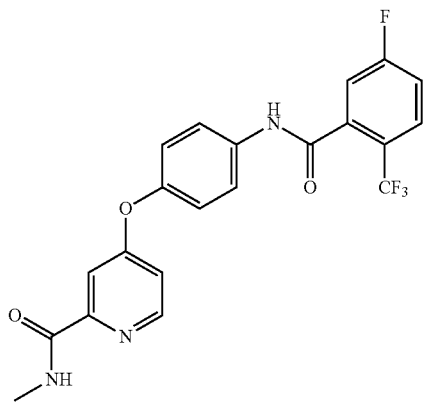 [SMILES: CNC(=O)c1cc(Oc2ccc(NC(=O)c3cc(F)ccc3C(F)(F)F)cc2)ccn1]

$^1$H NMR (400 MHz, CDCl$_3$): δ 8.66 (d, 1H, J=12.4 Hz), 8.31-8.26 (m, 2H), 7.93 (s, 1H), 7.70-7.65 (m, 3H), 7.56 (t, 1H, J=2.4 Hz), 7.24-7.19 (m, 1H), 7.02 (d, 2H, J=6.4 Hz), 6.89-6.87 (m, 1H), 2.90 (d, 3H, J=3.2 Hz); $^{13}$C NMR (100 MHz, methanol-d$_4$): δ 166.2, 164.5, 162.9, 160.4, 160.0, 159.9, 152.2, 150.4, 149.7, 135.0, 130.6 (m), 129.8 (m), 128.3, 128.1, 127.7, 127.4, 124.5, 122.5, 122.4, 122.3, 121.8, 121.5, 117.2, 117.0, 114.1, 110.1, 26.1; HRMS calculated for C$_{21}$H$_{15}$F$_4$N$_3$O$_3$ (M+H): 433.1050. Found: 433.0152.

1.2.2.10.

N-Methyl-4-(4-(4-(trifluoromethyl)benzamido)phenoxy)picolinamide (11)

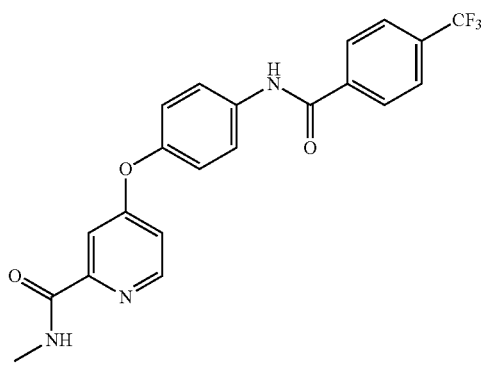 [SMILES: CNC(=O)c1cc(Oc2ccc(NC(=O)c3ccc(C(F)(F)F)cc3)cc2)ccn1]

$^1$H NMR (400 MHz, CDCl$_3$): δ 9.45 (s, 1H), 8.31 (d, 1H, J=5.6 Hz), 8.15 (s, 1H), 8.08 (d, 2H, J=8.0 Hz), 7.71-7.65 (m, 3H), 7.50 (d, 1H, J=2.4 Hz), 7.47 (t, 1H, J=8.0 Hz), 6.96-6.91 (m, 3H), 2.92 (d, 3H, J=5.2 Hz); $^{13}$C NMR (100 MHz, CDCl$_3$): δ 166.4, 164.8, 164.7, 151.8, 149.9, 149.8, 138.8, 135.5, 131.4, 131.1, 130.8, 130.7, 130.5, 129.1, 128.1, 125.0, 124.3 (m), 122.6, 122.3, 121.2, 114.4, 109.5, 26.1; HRMS calculated for C$_{21}$H$_{16}$F$_3$N$_3$O$_3$ (M+H): 415.1144. Found: 415.1146.

1.2.2.11.

2-Nitro-N-(4-(quinolin-4-yloxy)phenyl)-4-(trifluoromethyl)benzenesulfonamide (12)

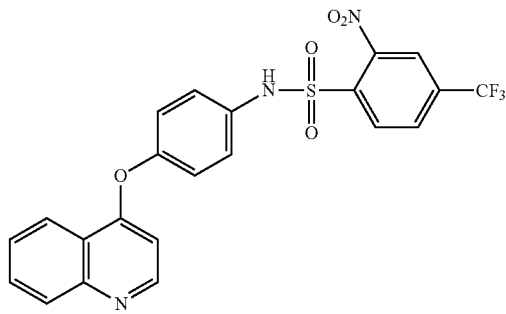 [SMILES: O=[N+]([O-])c1cc(C(F)(F)F)ccc1S(=O)(=O)Nc1ccc(Oc2ccnc3ccccc23)cc1]

$^1$H NMR (400 MHz, CDCl$_3$): δ 8.71 (d, 1H, J=5.2 Hz), 8.28 (d, 1H, J=8.4 Hz), 8.12 (d, 1H, J=8.4 Hz), 8.10 (s, 1H), 8.05 (d, 1H, J=8.4 Hz), 7.89 (d, 1H, J=8.4 Hz), 7.80-7.76 (m, 1H), 7.61-7.57 (m, 1H), 7.31 (d, 2H, J=8.8 Hz), 7.13 (d, 1H, J=8.8 Hz), 6.53 (d, 1H, J=5.2 Hz); HRMS calculated for C$_{22}$H$_{14}$F$_3$N$_3$O$_5$S (M+H): 489.0606. Found: 489.0610.

1.2.2.12.

2-Nitro-N-(4-(8-nitroquinolin-4-yloxy)phenyl)-4-(trifluoromethyl)benzenesulfonamide (13)

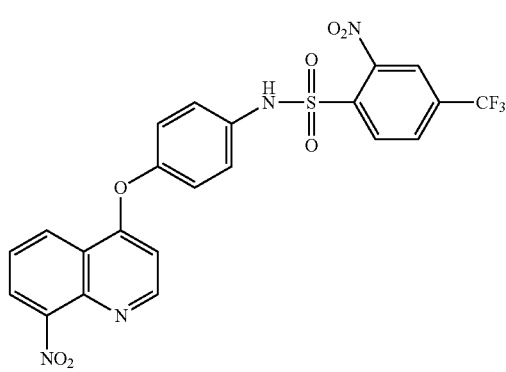 [SMILES: O=[N+]([O-])c1cc(C(F)(F)F)ccc1S(=O)(=O)Nc1ccc(Oc2ccnc3c([N+](=O)[O-])cccc23)cc1]

$^1$H NMR (400 MHz, CDCl$_3$): δ 8.78 (d, 1H, J=5.2 Hz), 8.51 (d, 1H, J=8.8 Hz), 8.19 (s, 1H), 8.12-8.02 (m, 3H), 7.89 (t, 1H, J=9.6 Hz), 7.62 (t, 1H, J=8.4 Hz), 7.34 (d, 2H, J=9.6 Hz), 7.15 (d, 2H, J=9.6 Hz), 6.91 (d, 1H, J=6.8 Hz), 6.59 (d, 1H, J=5.2 Hz), 6.55 (d, 1H, J=6.8 Hz); HRMS calculated for C$_{22}$H$_{13}$F$_3$N$_4$O$_7$S (M+H): 534.0457. Found: 534.0423.

1.2.2.13

2-Bromo-N-(4-(quinolin-4-yloxy)phenyl)-4-(trifluoromethyl)benzenesulfonamide (14)

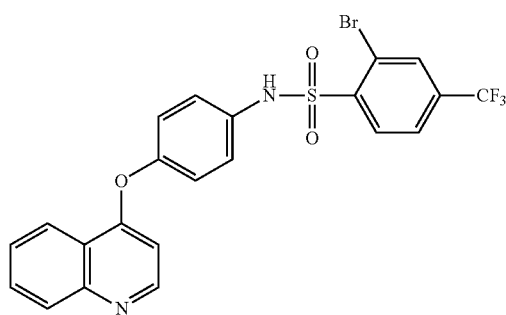 [SMILES: O=S(=O)(Nc1ccc(Oc2ccnc3ccccc23)cc1)c1ccc(C(F)(F)F)cc1Br]

$^1$H NMR (400 MHz, CDCl$_3$): δ 8.65 (d, 1H, J=5.2 Hz), 8.25 (d, 1H, J=8.4 Hz), 8.18 (d, 1H, J=8.4 Hz), 8.07 (d, 1H, J=8.4 Hz), 7.98 (s, 1H), 7.73 (t, 1H, J=7.6 Hz), 7.67 (d, 1H, J=8.4 Hz), 7.54 (t, 1H, J=7.6 Hz), 7.24 (d, 2H, J=8.8 Hz), 7.05 (d, 2H, J=8.8 Hz), 6.43 (d, 1H, J=5.2 Hz); $^{13}$C NMR (100 MHz, CDCl$_3$): δ 161.3, 152.6, 150.9, 149.7, 141.4, 135.9, 135.6, 135.3, 132.7, 132.4, 132.2 (m), 130.3, 129.1, 126.3, 124.9 (m), 124.4, 123.5, 122.1, 122.0, 121.9, 121.6, 121.3, 120.8, 120.4, 116.3, 104.4; HRMS calculated for C$_{22}$H$_{14}$BrF$_3$N$_2$O$_3$S (M+H): 521.9861. Found: 521.9858.

1.2.2.14.

2-Bromo-N-(4-(8-nitroquinolin-4-yloxy)phenyl)-4-(trifluoromethyl)benzenesulfonamide (15)

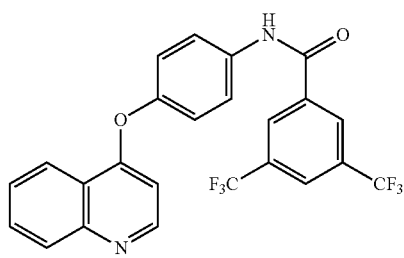 [SMILES: O=C(Nc1ccc(Oc2ccnc3ccccc23)cc1)c1cc(C(F)(F)F)cc(C(F)(F)F)c1]

$^1$H NMR (400 MHz, CDCl$_3$): δ 8.76 (d, 1H, J=5.2 Hz), 8.49 (d, 1H, J=8.4 Hz), 8.18 (d, 1H, J=8.4 Hz), 8.04 (d, 1H, J=7.6 Hz), 7.99 (s, 1H), 7.68 (d, 1H, J=8.4 Hz), 7.60 (t, 1H, J=8.4 Hz), 7.25 (d, 2H, J=8.4 Hz), 7.07 (d, 2H, J=8.4 Hz), 6.53 (d, 1H, J=5.2 Hz); HRMS calculated for C$_{22}$H$_{13}$BrF$_3$N$_3$O$_5$S (M+H): 566.9711. Found: 566.9706.

1.2.2.15. N-(4-(Quinolin-4-yloxy)phenyl)-3,5-bis(trifluoromethyl)benzamide (16)

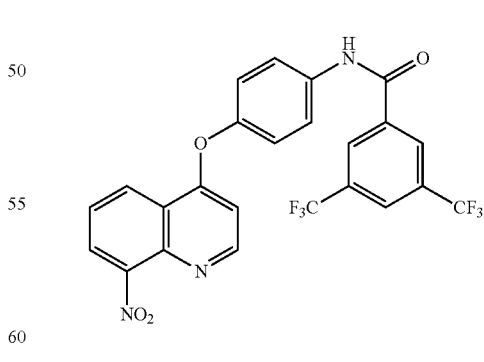

$^1$H NMR (400 MHz, CDCl$_3$): δ 10.02 (s, 1H), 8.59 (d, 1H, J=5.6 Hz), 8.37 (s, 2H), 8.34 (d, 1H, J=8.4 Hz), 7.99 (d, 1H, J=8.4 Hz), 7.92 (s, 1H), 7.80 (d, 2H, J=9.2 Hz), 7.70 (t, 1H, J=7.6 Hz), 6.56 (t, 1H, J=7.6 Hz), 7.14 (d, 2H, J=9.2 Hz), 6.52 (d, 1H, J=5.2 Hz); $^{13}$C NMR (100 MHz, DMSO-d$_6$): δ 162.6, 161.0, 151.5, 150.0, 149.2, 137.0, 136.1, 131.0, 130.7, 130.4, 130.3, 130.0, 128.8, 128.5 (m), 126.4, 125.2 (m), 124.5, 122.5, 121.7, 121.5, 121.3, 120.6, 104.3; HRMS calculated for C$_{24}$H$_{14}$F$_6$N$_2$O$_2$ (M+H): 476.0959. Found: 476.0958.

1.2.2.16

N-(4-(8-Nitroquinolin-4-yloxy)phenyl)-3,5-bis(trifluoromethyl)benzamide (17)

$^1$H NMR (400 MHz, CDCl$_3$): δ 9.05 (s, 1H), 8.69 (d, 1H, J=5.0 Hz), 8.59 (d, 1H, J=5.0 Hz), 8.35 (s, 2H), 8.06 (d, 1H, J=7.8 Hz), 7.97 (s, 1H), 7.80 (d, 2H, J=9.0 Hz), 7.63 (t, 1H, J=8.6 Hz), 7.16 (d, 2H, J=9.0 Hz), 6.62 (d, 1H, J=5.0 Hz); HRMS calculated for C$_{24}$H$_{13}$F$_6$N$_3$O$_4$ (M+H): 521.0810. Found: 521.0814.

1.2.2.17 2-Fluoro-N-(4-(quinolin-4-yloxy)phenyl)-5-(trifluoromethyl)benzamide (18)

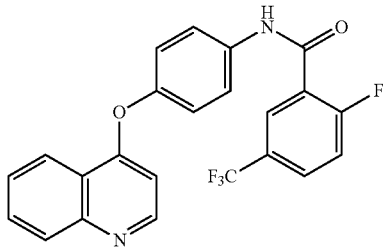 [SMILES: O=C(Nc1ccc(Oc2ccnc3ccccc23)cc1)c1cc(C(F)(F)F)ccc1F]

¹H NMR (400 MHz, CDCl₃): δ 8.83 (d, 1H, J=12.8 Hz), 8.68 (d, 1H, J=5.2 Hz), 8.39-8.30 (m, 2H), 8.11 (d, 1H, J=8.4 Hz), 7.79-7.67 (m, 4H), 7.58 (t, 1H, J=8.0 Hz), 7.27-7.22 (m, 1H), 7.18 (d, 2H, J=9.2 Hz), 6.56 (d, 1H, J=5.2 Hz); ¹³C NMR (100 MHz, methanol-d₄): δ 164.4, 164.2, 163.8, 161.7, 151.9, 151.8, 149.7, 137.5, 132.1 (m), 131.2 (m), 128.9 (m), 128.3, 128.1, 127.9, 126.5, 126.3, 123.7, 123.6, 123.0, 122.7, 122.6, 119.1, 119.8, 118.7, 118.5, 105.2; HRMS calculated for C₂₃H₁₄F₄N₂O₂ (M+H): 426.0991. Found: 426.0991.

1.2.2.18.

2-Fluoro-N-(4-(8-nitroquinolin-4-yloxy)phenyl)-5-(trifluoromethyl)benzamide (19)

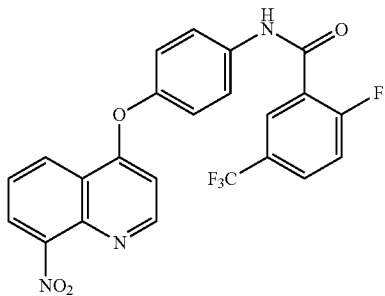 [SMILES: O=C(Nc1ccc(Oc2ccnc3c([N+](=O)[O-])cccc23)cc1)c1cc(C(F)(F)F)ccc1F]

¹H NMR (400 MHz, CDCl₃): δ 8.81 (d, 1H, J=5.2 Hz), 8.59 (d, 1H, J=8.8 Hz), 8.53-8.47 (m, 2H), 8.06 (d, 1H, J=7.6 Hz), 7.83-7.77 (m, 3H), 7.64 (t, 1H, J=7.6 Hz), 7.37-7.32 (m, 1H), 7.23-7.20 (m, 2H), 6.68 (d, 1H, J=5.2 Hz); HRMS calculated for C₂₃H₁₃F₄N₃O₄ (M+H): 471.0842. Found: 471.0850.

1.2.2.19

N-(3-Methyl-4-(8-nitroquinolin-4-yloxy)phenyl)-3,5-bis(trifluoromethyl)benzamide (20)

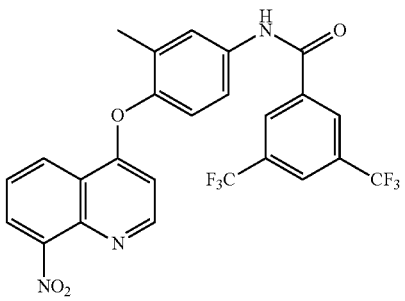 [SMILES: Cc1cc(NC(=O)c2cc(C(F)(F)F)cc(C(F)(F)F)c2)ccc1Oc1ccnc2c(N)cccc12]

¹H NMR (400 MHz, CDCl₃): δ 9.86 (s, 1H), 8.45 (d, 1H, J=5.2 Hz), 8.38 (s, 2H), 8.31 (d, 1H, J=8.4 Hz), 7.92 (s, 1H), 7.89 (d, 1H, J=8.4 Hz), 7.69-7.63 (m, 2H), 7.53 (t, 1H, J=7.6 Hz), 7.33 (s, 1H), 7.28 (d, 1H, J=8.4 Hz), 6.33 (d, 1H, J=5.2 Hz); HRMS calculated for C₂₅H₁₅F₆N₃O₄ (M+H): 535.0967 Found: 535.0956.

1.2.2.20.

N-(4-(8-Aminoquinolin-4-yloxy)-3-methylphenyl)-3,5-bis(trifluoromethyl)benzamide (21)

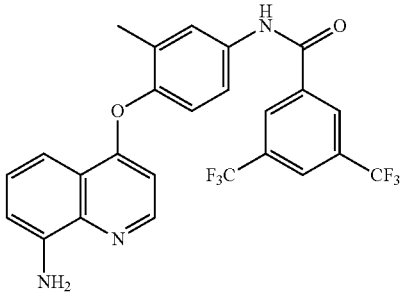

¹H NMR (400 MHz, CDCl₃): δ 8.49 (d, 1H, J=2.0 Hz), 8.27 (s, 1H), 8.02 (s, 1H), 7.94 (s, 1H), 7.65 (d, 1H, J=8.0 Hz), 7.48-7.45 (m, 2H), 7.37-7.32 (m, 2H), 6.96 (d, 1H, J=7.6 Hz), 4.95 (s, 2H), 2.16 (s, 3H); HRMS calculated for C₂₅H₁₇F₆N₃O₂ (M+H): 505.1225. Found: 505.1216.

1.2.2.21.

N-(4-(8-Acetamidoquinolin-4-yloxy)-3-methylphenyl)-3,5-bis(trifluoromethyl)benzamide (22)

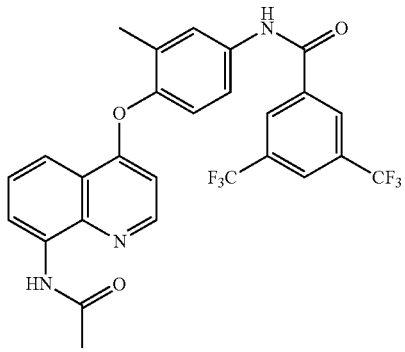 [SMILES: CC(=O)Nc1cccc2c(Oc3ccc(NC(=O)c4cc(C(F)(F)F)cc(C(F)(F)F)c4)cc3C)ccnc12]

$^1$H NMR (400 MHz, CDCl$_3$): δ 9.77 (s, 1H), 9.36 (s, 1H), 8.65 (d, 1H, J=7.2 Hz), 8.46 (s, 2H), 8.44 (d, 1H, J=5.2 Hz), 7.97 (s, 1H), 7.87 (d, 1H, J=8.4 Hz), 7.72 (d, 1H, J=8.4 Hz), 7.50 (d, 1H, J=2.0 Hz), 7.37 (t, 1H, J=8.0 Hz), 7.28 (d, 1H, J=8.4 Hz), 6.41 (d, 1H, J=5.2 Hz), 2.26 (s, 3H), 2.10 (s, 3H); $^{13}$C NMR (100 MHz, CDCl$_3$): δ 169.2, 163.0, 161.2, 152.0, 148.8, 139.5, 137.2, 136.7, 133.8, 132.6, 132.3, 132.2, 132.0, 131.6, 127.8, 127.1, 126.3, 125.2 (m), 124.2, 121.5, 120.4, 118.8, 118.3, 116.7, 115.7, 113.8, 25.0, 15.4; HRMS calculated for C$_{27}$H$_{19}$F$_6$N$_3$O$_3$ (M+H): 547.1331. Found: 547.1325.

1.2.2.22.

N-(3-(8-Nitroquinolin-4-yloxy)phenyl)-3,5-bis(trifluoromethyl)benzamide (23)

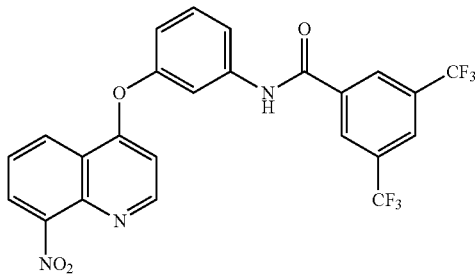

$^1$H NMR (400 MHz, CDCl$_3$): δ 8.78 (d, 1H, J=5.6 Hz), 8.58 (d, 1H, J=8.4 Hz), 8.52 (s, 1H), 8.31 (s, 2H), 8.22 (s, 1H), 8.08-8.04 (m, 2H), 7.71 (s, 1H), 7.64 (t, 1H, J=8.0 Hz), 7.53-7.49 (m, 2H), 7.03 (d, 1H, J=7.2 Hz), 6.71 (d, 1H, J=4.8 Hz); HRMS calculated for C$_{24}$H$_{13}$F$_6$N$_3$O$_4$ (M+H): 521.0810. Found: 521.0821.

1.2.2.23.

N-(3-(8-Aminoquinolin-4-yloxy)phenyl)-3,5-bis(trifluoromethyl)benzamide (24)

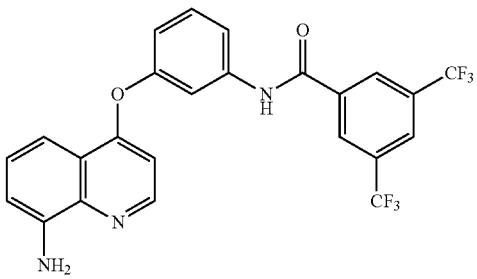 [SMILES: O=C(Nc1cccc(Oc2ccnc3c([N+](=O)[O-])cccc23)c1)c1cc(C(F)(F)F)cc(C(F)(F)F)c1]

$^1$H NMR (400 MHz, CDCl$_3$): δ 8.55 (d, 1H, J=4.8 Hz), 8.29 (s, 2H), 8.05 (s, 1H), 7.90 (s, 1H), 7.60 (d, 1H, J=8.4 Hz), 7.55 (s, 1H), 7.70-7.43 (m, 2H), 7.34 (t, 1H, J=8.0 Hz), 7.01 (d, 1H, J=8.0 Hz), 6.96 (d, 1H, J=7.9 Hz), 6.63 (d, 1H, J=4.8 Hz); $^{13}$C NMR (100 MHz, CDCl$_3$): δ 163.1, 161.3, 155.3, 147.9, 143.6, 139.9, 138.8, 136.5, 132.7, 132.4, 132.1, 131.7, 130.6, 127.5 (d), 127.0, 126.8, 125.3 (m), 124.1, 122.0, 118.7, 117.4, 117.2, 113.1, 111.1, 110.0, 105.4; HRMS calculated for C$_{24}$H$_{15}$F$_6$N$_3$O$_2$ (M+H): 491.1068. Found: 491.1068.

1.2.2.24.

N-(3-(8-Acetamidoquinolin-4-yloxy)phenyl)-3,5-bis(trifluoromethyl)benzamide (25)

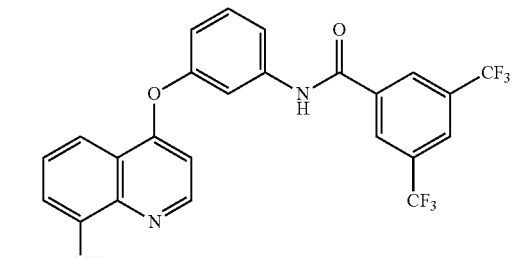

$^1$H NMR (400 MHz, CDCl$_3$): δ 9.77 (s, 1H), 8.74 (d, 1H, J=7.6 Hz), 8.54 (d, 1H, J=5.2 Hz), 8.48 (s, 1H), 8.39 (s, 2H), 8.04 (s, 1H), 7.87 (d, 1H, J=8.4 Hz), 7.67-7.60 (m, 2H), 7.50-7.43 (m, 2H), 7.37 (t, 1H, J=8.0 Hz), 7.00 (d, 1H, J=8.4 Hz), 6.65 (d, 1H, J=5.2 Hz), 2.30 (s, 3H); $^{13}$C NMR (100 MHz, CDCl$_3$): δ 169.3, 163.1, 161.7, 154.6, 148.7, 139.6, 136.6, 133.8, 132.7, 132.4, 132.1, 131.7, 130.8, 127.8 (d), 126.9, 126.5, 125.3 (m), 124.2, 121.5, 120.8, 117.7, 117.3, 116.8, 115.7, 113.2, 104.9, 25.0; HRMS calculated for C$_{26}$H$_{17}$F$_6$N$_3$O$_3$ (M+H): 533.1174. Found: 533.1167.

1.2.2.25

N-(3-(trifluoromethyl)benzene-sulfonyl)-3-(3-amino-4-nitrophenoxy)benzenamine (SC-40)

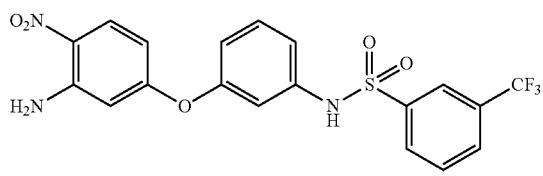 [SMILES: Nc1cc(Oc2cccc(NS(=O)(=O)c3cccc(C(F)(F)F)c3)c2)ccc1[N+](=O)[O-]]

¹H NMR (400 MHz, CDCl₃): δ 8.06 (d, J=9.6 Hz, 1H), 8.00 (s, 1H), 7.96 (d, J=8.0 Hz, 1H), 7.81 (d, J=8.0 Hz, 1H), 7.61 (t, J=8.0 Hz, 1H), 7.27 (t, J=8.0 Hz, 1H), 6.91-6.80 (m, 3H), 6.19 (dd, J=9.6 Hz, 2.4 Hz, 1H), 6.14 (d, J=2.4 Hz, 1H), 6.10 (brs, 2H); ¹³C NMR (100 MHz, CDCl₃): δ 163.1, 155.5, 146.7, 140.0, 137.6, 132.0, 131.6, 130.9, 130.3, 130.0, 129.9 (m), 128.8, 128.0, 124.4, 124.3, 124.2, 124.2, 124.0, 121.6, 117.8, 117.6, 113.6, 107.6, 104.3; LC-MS (ESI): M/Z 452 [M–H]⁻; HRMS calculated for $C_{19}H_{13}N_3O_5F_3S$ [M–H]⁻: 452.0528. Found: 452.0529.

1.2.3 Compound 36-38
1.2.3.1

3-(2-phenylH-imidazo[1,2-a]pyridin-7-yloxy)-N-(3-(trifluoromethoxy)benzyl)benzenemine (36)

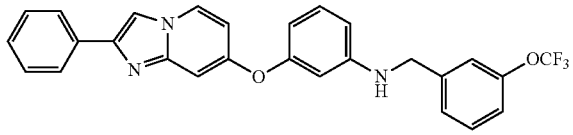

¹H NMR (400 MHz, CDCl₃): δ 7.96 (d, J=8.0 Hz, 1H), 7.89 (d, J=8.0 Hz, 2H), 7.71 (s, 1H), 7.40 (t, J=7.2 Hz, 2H), 7.35-7.24 (m, 3H), 7.18 (s, 1H), 7.14 (t, J=8.0 Hz, 1H), 7.09 (d, J=7.6 Hz, 1H), 6.98 (d, J=2.4 Hz, 1H), 6.60 (dd, J=7.2 Hz, 2.4 Hz, 1H), 6.46-6.40 (m, 2H), 6.32 (t, J=2.4 Hz, 1H), 4.31 (s, 1H), 4.20 (s, 1H); HRMS calculated for $C_{27}H_{21}N_3O_2F_3$ [M+H]⁺: 476.1586. Found: 476.1592.

1.2.3.2

N-(3-(2-phenylimidazo[1,2-a]pyridin-7-yloxy)phenyl)-3-(trifluoromethyl)benzenesulfonamide (37)

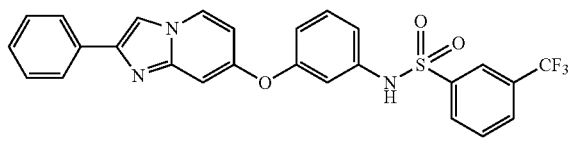

¹H NMR (400 MHz, CDCl₃): δ 8.03 (d, J=6.8 Hz, 2H), 7.92 (d, J=8.0 Hz, 1H), 7.87 (d, J=6.8 Hz, 2H), 7.76 (d, J=6.0 Hz, 2H), 7.60 (t, J=7.6 Hz, 1H), 7.39 (t, J=8.0 Hz, 2H), 7.30 (t, J=6.4 Hz, 1H), 7.21 (d, J=8.8 Hz, 1H), 6.96-6.90 (m, 2H), 6.83 (dd, J=13.6 Hz, 2.4 Hz, 1H), 6.82 (t, J=2.0 Hz, 2H), 6.60 (dd, J=7.2 Hz, 2.4 Hz, 1H); HRMS calculated for $C_{26}H_{19}N_3O_3F_3S$ [M+H]⁺: 510.1099. Found: 510.1100.

1.2.3.3

N-(3-(2-phenylimidazo[1,2-a]pyridin-7-yloxy)phenyl)benzenesulfonamide (38)

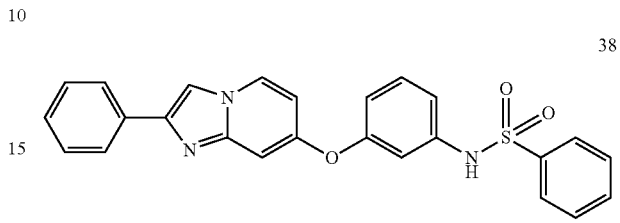

¹H NMR (400 MHz, DMSO): δ 8.52 (d, J=7.2 Hz, 1H), 8.33 (s, 1H), 7.93 (d, J=7.2 Hz, 2H), 7.76-7.70 (m, 2H), 7.66-7.54 (m, 3H), 7.43 (t, J=7.6 Hz, 2H), 7.33-7.26 (m, 2H), 6.92 (d, J=7.6 Hz, 1H), 6.84-6.76 (m, 3H), 6.64 (dd, J=7.6 Hz, 2.4 Hz, 1H); HRMS calculated for $C_{25}H_{20}N_3O_3S$ [M+H]⁺: 442.1225. Found: 442.1216.

Example 2

Bioassay 2.1 Materials and Methods
2.1.1. Reagents and Antibodies

Sorafenib (Nexavar®) was kindly provided by Bayer Pharmaceuticals (West Haven, Conn.). Sodium vanadate and SHP-1 inhibitor were purchased from Cayman Chemical (Ann Arbor, Mich.). Antibodies for immunoblotting such as Raf-1, cylcin D1, and PARP were purchased from Santa Cruz Biotechnology (San Diego, Calif.). Other antibodies such as anti-pVEGFR2 (Y1175), VEGFR2, survivin, phospho-STAT3 (Tyr705), and STAT3 were from Cell Signaling (Danvers, Mass.).

2.1.2. Cell Culture

The Huh-7 HCC cell line was obtained from the Health Science Research Resources Bank (Osaka, Japan; JCRB0403). The PLC/PRF/5 (PLC5), Sk-Hep-1, and Hep3B cell lines were obtained from American Type Culture Collection (Manassas, Va.). The cells were maintained in DMEM supplemented with 10% FBS, 100 units/mL penicillin G, 100 μg/mL streptomycin sulfate and 25 μg/mL amphotericin B in a 37° C. humidified incubator in an atmosphere of 5% CO₂ in air. Other cell lines, including breast cancer cells e.g. MDAMB231, MDAMB468, MCF-7, and leukemia cancer cells e.g. HL-60, KG-1 and ML-1 are also provided for the assays described below.

2.1.3. Cell Death Detection ELISA

The effect of the compounds of the invention on cell viability was assessed by cell death ELISA assay (Roche Applied Science. Mannheim, Germany). Cells were treated with a test compound at 5 and 10 μM for 24 h, for example. The cells were collected and applied to the standard protocol provided by manufacture.

2.1.4. Apoptosis Analysis

Apoptotic cells were measured by flow cytometry (sub-G1). After treatment with various compounds, cells were trypsinized, collected by centrifugation and resuspended in PBS. After centrifugation, the cells were washed in PBS and resuspended in potassium iodide (PI) staining solution.

Specimens were incubated in the dark for 30 min at 37° C. and then analyzed with an EPICS Profile II flow cytometer (Coulter Corp., Hialeah, Fla.). All experiments were performed in triplicate 2.1.5. Phospho-STAT3-Level A PathScan Phospho-Stat3 (Tyr705) Sandwich ELISA Kit was used for the detection of phospho-STAT3 (Cell Signaling, Danvers, Mass.). Cells were pre-treated with IL-6 1 ng/ml and then exposed with various compounds at 10 µM for 24 h. After incubation with cell lysates, both non-phospho- and phospho-Stat3 proteins are captured by the coated antibody. The expression of phospho-STAT3 was measured at 450 nm absorbance.

2.1.6. Western Blot

Cells were treated with various compounds at 5 and 10 µM for 24 h. Cell lysates were analyzed by western blot.

2.1.7. Gene Knockdown Using siRNA

Smart-pool siRNA, including control (D-001810-10), Raf-1, SHP-1, SHP-2, and PTP-1B, were all purchased from Dharmacon Inc. (Chicago, Ill.). The procedure has been described previously (Chen K F et al. *J Biol Chem* 2009; 284:11121-11133).

2.1.8. PLC5 with Ectopic Expression of STAT3

STAT3 cDNA (KIAA1524) and STAT3-C were purchased from Addgene plasmid repository (http://www.addgene-.org/). Briefly, following transfection, cells were incubated in the presence of G418 (0.78 mg/mL). After 8 weeks of selection, surviving colonies, i.e., those arising from stably transfected cells, were selected and individually amplified.

2.1.9. Phosphatase and Kinase Activity

The RediPlate 96 EnzChek® Tyrosine Phosphatase Assay Kit (R-22067) was used for SHP-1 activity assay (Molecular Probes, Carlsbad, Calif.). The Raf-1 kinase cascade assay kit (Upstate-Millipore, Billerica, Mass.) was used to examine the Raf-1 kinase activity. The JAK2 kinase activity kit was purchased from Reaction Biology Corp. (Malvern, Pa.).

2.1.10. STAT3 Reporter Assay

Cells were seeded in 96-well plate and pre-treated with IL-6 at the dose 10 ng/µl for 30 min. The STAT3 reporter kit was purchased from SABiosciences (Frederick, Md.).

2.1.11. Xenograft Tumor Growth

Male NCr athymic nude mice (5-7 weeks of age) were obtained from the National Laboratory Animal Center (Taipei, Taiwan). All experimental procedures using these mice were performed in accordance with protocols approved by National Taiwan University. When Huh-7 tumors reached 100-200 mm$^3$, mice received sorafenib tosylate (10 mg/kg) p.o. (oral) once daily, or SC-1(10 mg/kg) p.o. (oral) once daily. Controls received vehicle (Chen K F et al. *Cancer Res.* 2008; 68:6698-6707).

2.1.12. Statistical Analysis.

Comparisons of mean values were performed using the independent samples t test in SPSS for Windows 11.5 software (SPSS, Inc., Chicago, Ill.) (Chen K F et al. Cancer Res 2008; 68:6698-6707).

2.2 Results 2.2.1 Compound 1 does not Affect Raf Kinase Activity

Figure 3:
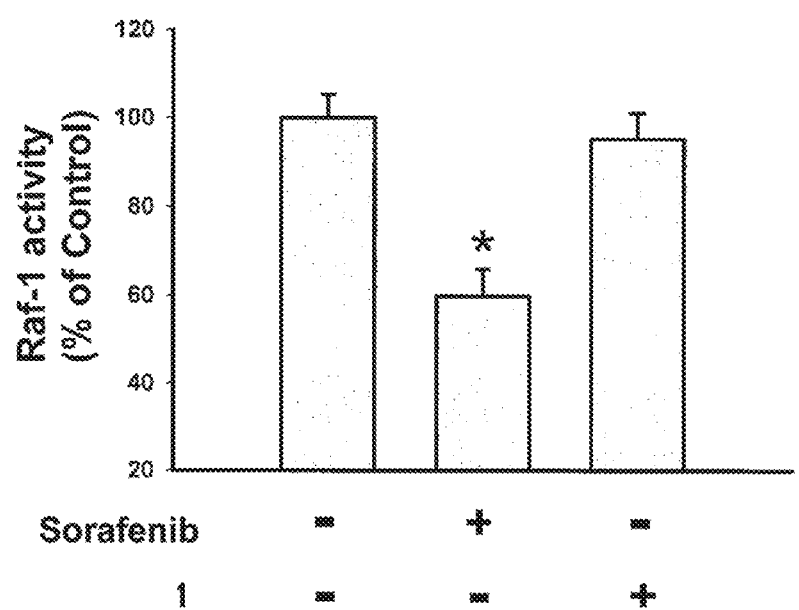
FIG. 3 shows Raf-1 activity in the cells treated by sorafenib and compound 1, respectively. Huh-7 cells were exposed to sorafenib or compound 1 at 10 μM for 24 hours and cell lysates were analyzed for raf-1 activity. Columns, mean; bars, SD (n=3). *P<0.05.

As above described, we synthesized a sorafenib derivative without providing hydrogen donor ability by replacing the pyridine ring and amide functional group with phenyl cyanide. Then, we tested compound 1 for its ability to inhibit Raf kinase activity in PLC5 cells, compared with that of sorafenib. As shown in FIG. 3, sorafenib was able to inhibit 50% of the Raf-1 kinase activity of the untreated cells in the PLC5 cells at 5 µM; however, compound 1 treated cells showed the same Raf-1 activity as vehicle control. The loss of Raf-1 inhibition can presumably be attributed to the loss of hydrogen bonding ability, as a result of the replacement of the pyridine ring and amide functional group with phenyl cyanide.

2.2.2. Structure Activity Relationship of Replacement of Urea Group and Pyridine Ring in Cell Death As above described, we replaced the urea functional group linkage of sorafenib with various amide and sulfonamide, generating compounds 2-11. These compounds were analyzed by MTT assay for cell growth inhibition in the PLC5 cells. Table 4 shows the results.

TABLE 4

| Cpd | R$_4$ | IC$_{50}$ (µM) in PLC5 cells |
|---|---|---|
| Sorafenib | | 8.3 |
| 1 | | 7.5 |
| 2 | | >40 |
| 3 | | >40 |
| 4 | | >40 |
| 5 | | >40 |
| 6 | | >40 |

TABLE 4-continued

[Structure: 4-phenoxy-N-methylpyridine-2-carboxamide core with R4 substituent on para-aminophenyl]

| Cpd | R4 | IC₅₀ (μM) in PLC5 cells |
|---|---|---|
| 7 | [t-Bu-sulfonyl-(2-Br,4-CF₃)phenyl] | >40 |
| 8 | [t-Bu-sulfonyl-(2-NO₂)phenyl] | >40 |
| 9 | [pivaloyl-(3,5-bis-CF₃)phenyl] | >40 |
| 10 | [pivaloyl-(2-F,5-CF₃)phenyl] | >40 |
| 11 | [pivaloyl-(4-CF₃)phenyl] | >40 |

The results show that none of these derivatives within the electron donating or electron withdrawing group showed greater cell toxicity than sorafenib and compound 1.

Next, we changed the pyridine to a quinoline ring and amide linker to generate compounds 12-25. These compounds were also analyzed by MTT assay for cell growth inhibition in the PLC5 cells. Table 5 shows the results.

TABLE 5

[Structure: 4-phenoxyquinoline core with R4 substituent on para-aminophenyl]

| Cpd | R4 | IC₅₀ (μM) in PLC5 cells |
|---|---|---|
| 12 | [t-Bu-sulfonyl-(2-NO₂,4-CF₃)phenyl] | >40 |
| 14 | [t-Bu-sulfonyl-(2-Br,4-CF₃)phenyl] | >40 |
| 16 | [pivaloyl-(3,5-bis-CF₃)phenyl] | 16.0 |
| 18 | [pivaloyl-(2-F,5-CF₃)phenyl] | 21.1 |

TABLE 6

[Structure: 4-(phenoxy)-8-nitroquinoline with NH-R4 at para position of phenyl]

| Cpd | R4 | IC50 (μM) in PLC5 cells |
|---|---|---|
| 13 | t-Bu-SO2-(2-NO2,4-CF3-phenyl) | >40 |
| 15 | t-Bu-SO2-(2-Br,4-CF3-phenyl) | >40 |
| 17 | t-Bu-C(O)-(3,5-bis-CF3-phenyl) | >40 |
| 19 | t-Bu-C(O)-(2-F,5-CF3-phenyl) | >40 |

TABLE 6-continued

[Structure: 4-(phenoxy)-8-nitroquinoline with NH-R4 and R6 substituent on phenyl]

| Cpd | R4 | R6 | IC50 (μM) in PLC5 cells |
|---|---|---|---|
| 20 | t-Bu-C(O)-(3,5-bis-CF3-phenyl) | Me | >40 |
| 23 | t-Bu-C(O)-(3,5-bis-CF3-phenyl) | H | >40 |

[Structure: 4-(phenoxy)-8-nitroquinoline with NH-R4 and R6 substituent on phenyl]

| Cpd | R4 | R6 | IC50 (μM) in PLC5 cells |
|---|---|---|---|
| 21 | t-Bu-C(O)-(3,5-bis-CF3-phenyl) | Me | 25.4 |
| 24 | t-Bu-C(O)-(3,5-bis-CF3-phenyl) | H | 19.0 |

TABLE 6-continued

| Cpd | R4 | R6 | IC$_{50}$ (μM) in PLC5 cells |
|---|---|---|---|
| 22 | 3,5-bis(CF$_3$)-benzoyl | Me | >40 |
| 25 | 3,5-bis(CF$_3$)-benzoyl | H | 10.8 |

The amide linker showed different conformation from the sulfonyl linker, exhibiting better activity than sulfonyl linker compounds. For example, compound 16 showed a better cell toxicity than compound 12. Compound 25 showed cytotoxicity comparable to sorafenib and 1. We concluded that the urea and amide linkers exhibited the most potent cell toxicity in PLC5 cells.

2.2.3. Mechanistic Validation of the Mode of Action of Sorafenib Derivatives

Figure 4:
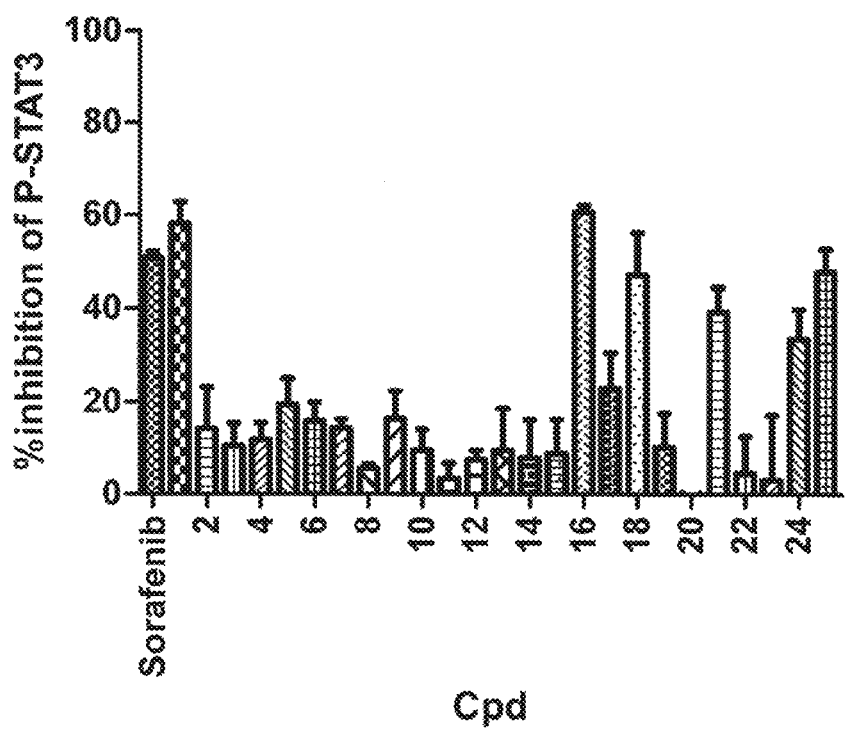
FIG. 4 shows the results of the ELISA analysis for the inhibitory effects of compounds 1-25 versus sorafenib, each at 10 μM, on the IL-6 stimulated P-STAT in PLC5 cells after 24 h of treatment. Columns, mean, bars, SD (N=3).

To check the dephosphorylation of STAT3 by sorafenib derivatives, we assessed P-STAT3 state in PLC5 cells exposed to 10 uM of each compound for 24 h by ELISA. As showed in FIG. 4, sulfonyl linker compounds showed no appreciable change in P-STAT3; however, compound 1 and some of the amide linker compounds showed a high degree of dephosphorylation of STAT3. The decreased level of P-STAT3 induced by these derivatives was correlated with cell toxicity. In the other words, these derivatives induced cell death in part through inhibition of STAT3.

Figure 5:
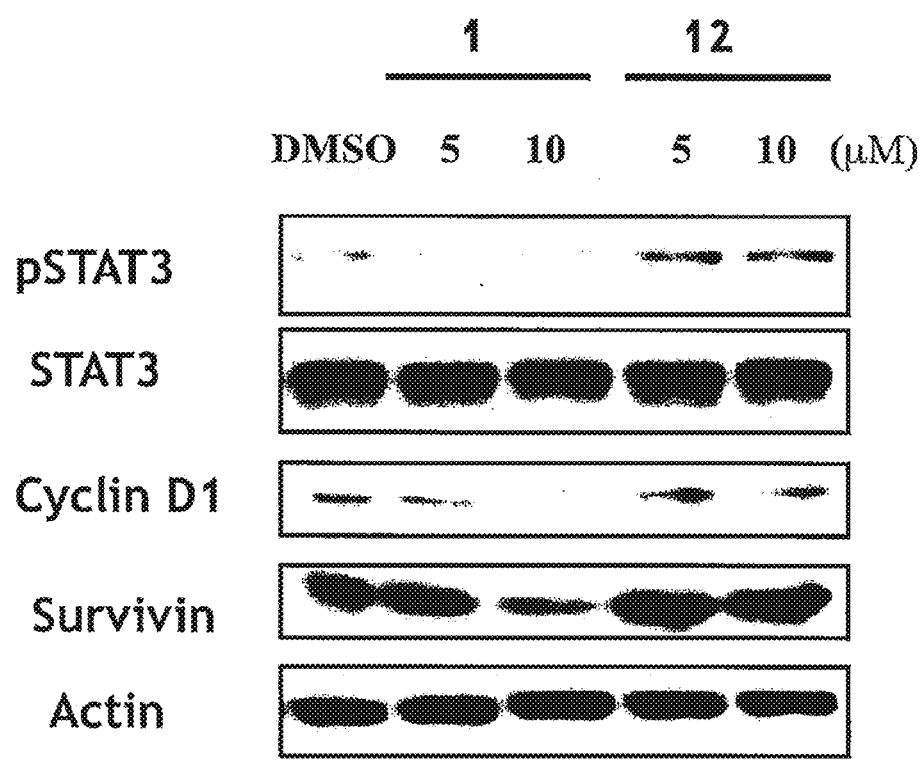
FIG. 5 shows the results of Western blot analysis for the effect of compounds 1 and 12, each at 5 μM and 10 μM on the phosporylation of P-STAT3, STAT3, cyclin D and survivin in PLC5 cells in FBS-containing medium after 24 h of treatment.
Figure 6:
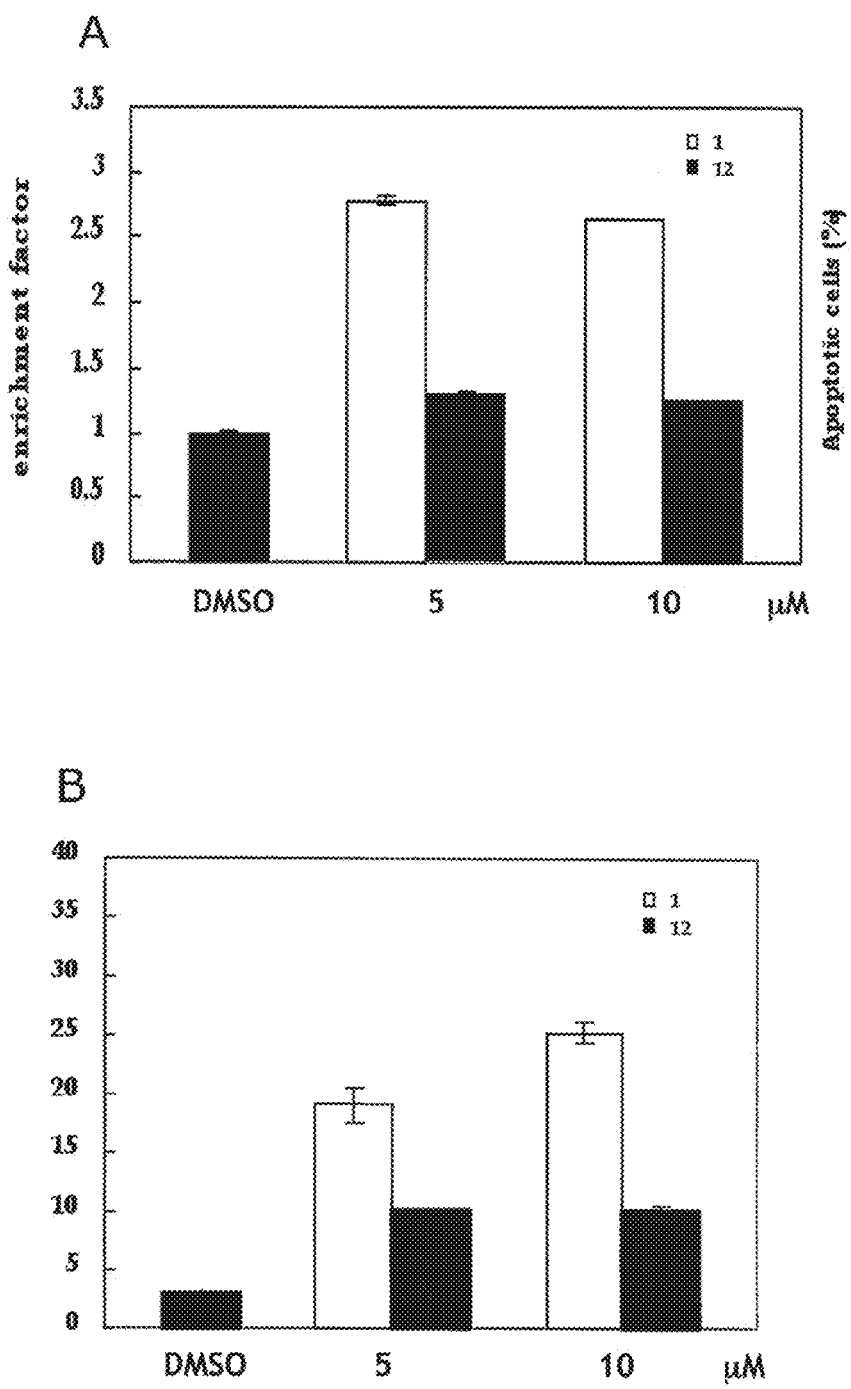
FIG. 6 shows (A) the results of ELISA analysis for cell death induced by compound 1 and 12, at 5, and 10 μM, after 24 h of treatment in PLC5 cells; and (B) shows the results of flow cytometry analysis of cell death induced by compound 1 and 12, at 5, and 10 μM, after 24 h of treatment in PLC5 cells.

In addition, we tested the downstream signal pathway after the inhibition of P-STAT3. Expression levels of the cyclin D1 and survivin, downstream target genes of STAT3, were assessed using compounds 1 and 12. As shown in FIG. 5, compound 1 with STAT3 inhibitory activity, was able to reduce cyclin D1 and survivin level, but compound 12 had no effect on either protein. Further, DNA fragmentation and flow cytometry analysis of PLC5 cells treated with compound 1 were conducted, and the results show that cell death was attributed to the inhibition of STAT3 and further induced the apoptotic signal (FIG. 6).

Our premise that sorafenib inhibition of Raf and STAT3 could be structurally dissociated was borne out by compound 1, which, devoid of Raf activity, exhibited the same level of downregulation of P-STAT3 as sorafenib did. We suggest that the cyanide group of compound 1 reduces its interaction with Raf. Subsequent modifications of sorafenib by changing the linker and pyridine ring to amide and quinoline (compounds 1, 16, and 25, respectively) resulted in a decrease in STAT3-repressing potency.

2.2.4. SC-1, a Sorafenib Derivative, Lacking Inhibitory Function of Raf-1 Showed Similar Cell Death Effect to Sorafenib in HCC Cell Lines.

Figure 7:
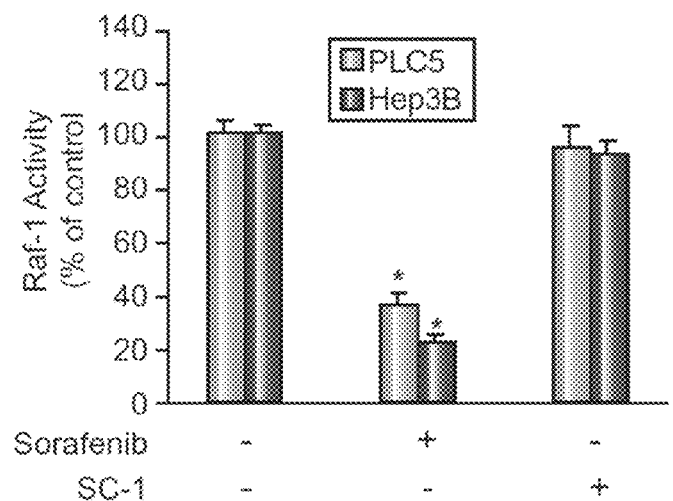
FIG. 7 shows (A) the effects of sorafenib and SC-1 on phospho-VEGFR2 in HUVEC cells, wherein the cells were exposed to sorafenib or SC-1 at 10 μM for 24 h; (B) the effects of sorafenib and SC-1 on Raf-1 activity, wherein the cells were exposed to sorafenib or SC-1 at 10 μM for 24 h. Points, mean; bars, SD (n=6).
Figure 7:
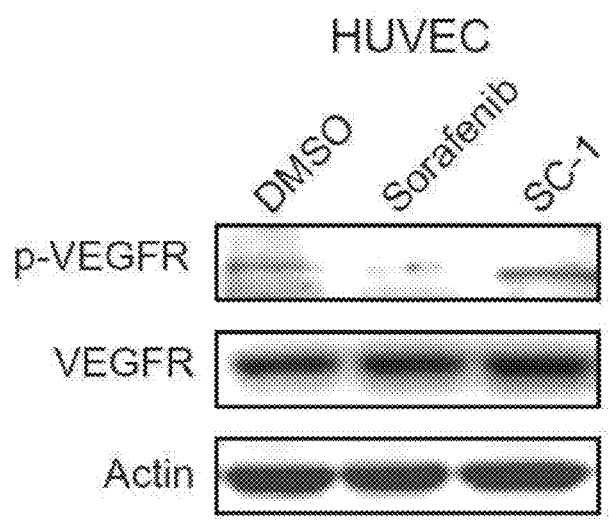

In this experiment, we again examined the effects of sorafenib and SC-1 on Raf-1 activity. Raf-1 immunoprecipitated from PLC5 or Hep3B cell extracts was incubated with MEK recombinant protein and the phospho-MEK was status assayed in the sorafenib or SC-1-treated cells. We observed a 20-40% reduction in Raf-1 kinase activity in the presence of sorafenib; however, SC-1 did not inhibit the activity of Raf-1, suggesting that SC-1 is not a Raf-1 inhibitor (FIG. 7A). In addition, we assayed the phosphorylation of VEGFR2, a key target of sorafenib in cancer treatment. The expression of p-VEGFR2 (Tyr1175) was decreased in PLC5 cells treated with sorafenib whereas SC-1 did not have significant effect (FIG. 7B). These data suggest that SC-1 derived from sorafenib does not affect kinase inhibition.

Figure 8:
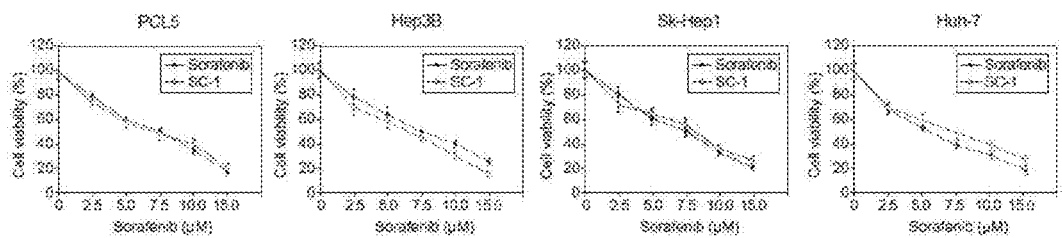
FIG. 8 shows (A) the dose-escalation effects of sorafenib and SC-1 on cell viability in four HCC cell lines, wherein cells were exposed to sorafenib or SC-1 at the indicated doses for 72 h and cell viability was assessed by MTT assay; and the dose-escalation effects of sorafenib and SC-1 on apoptosis in four HCC cell lines, wherein Cells were exposed to sorafenib or SC-1 at the indicated doses for 24 h, and cell lysates were analyzed by flow cytometry (B), or cell death ELISA (C). Points, mean; bars, SD (n=6).
Figure 8:
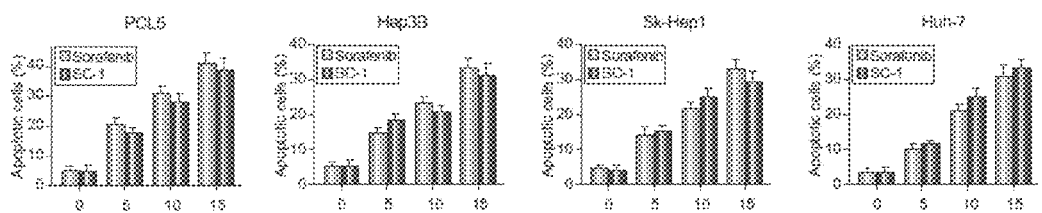
Figure 8:
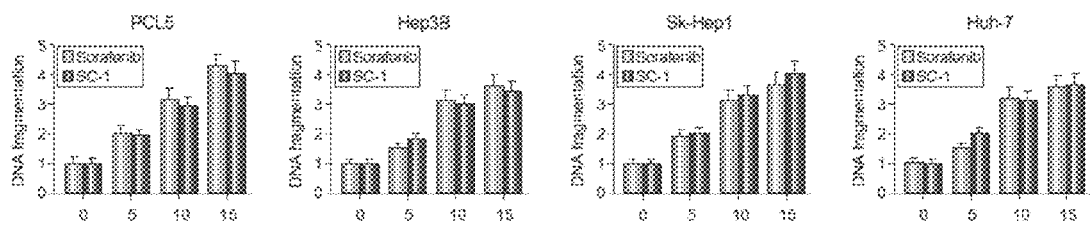

Next, we examined the anti-proliferation effects of sorafenib and SC-1. Both SC-1 and sorafenib decreased the viability of various HCC cells including PLC5, SK-Hep1, Huh7, and Hep3B in a dose-dependent manner (FIG. 8A). In addition, HCC cells treated with SC-1 or sorafenib showed a significant increase in sub-G1 phase population after 24 h exposure (FIG. 8B). Both drugs induced significant apoptotic cell death as detected by the induction of DNA fragmentation in SC-1 or sorafenib-treated HCC cells (FIG. 8C). These data indicate that SC-1 has a significant effect on apoptosis and as potent as sorafenib in inhibiting HCC cell growth even though SC-1 does not have the ability to block kinase activity, suggesting that the mechanism by which sorafenib induces apoptosis in HCC may not be related to its kinase inhibition activity.

2.2.5. STAT3 is a Vital to the Sensitizing Effect of Sorafenib and SC-1 in HCC Cell Lines.

Figure 9:
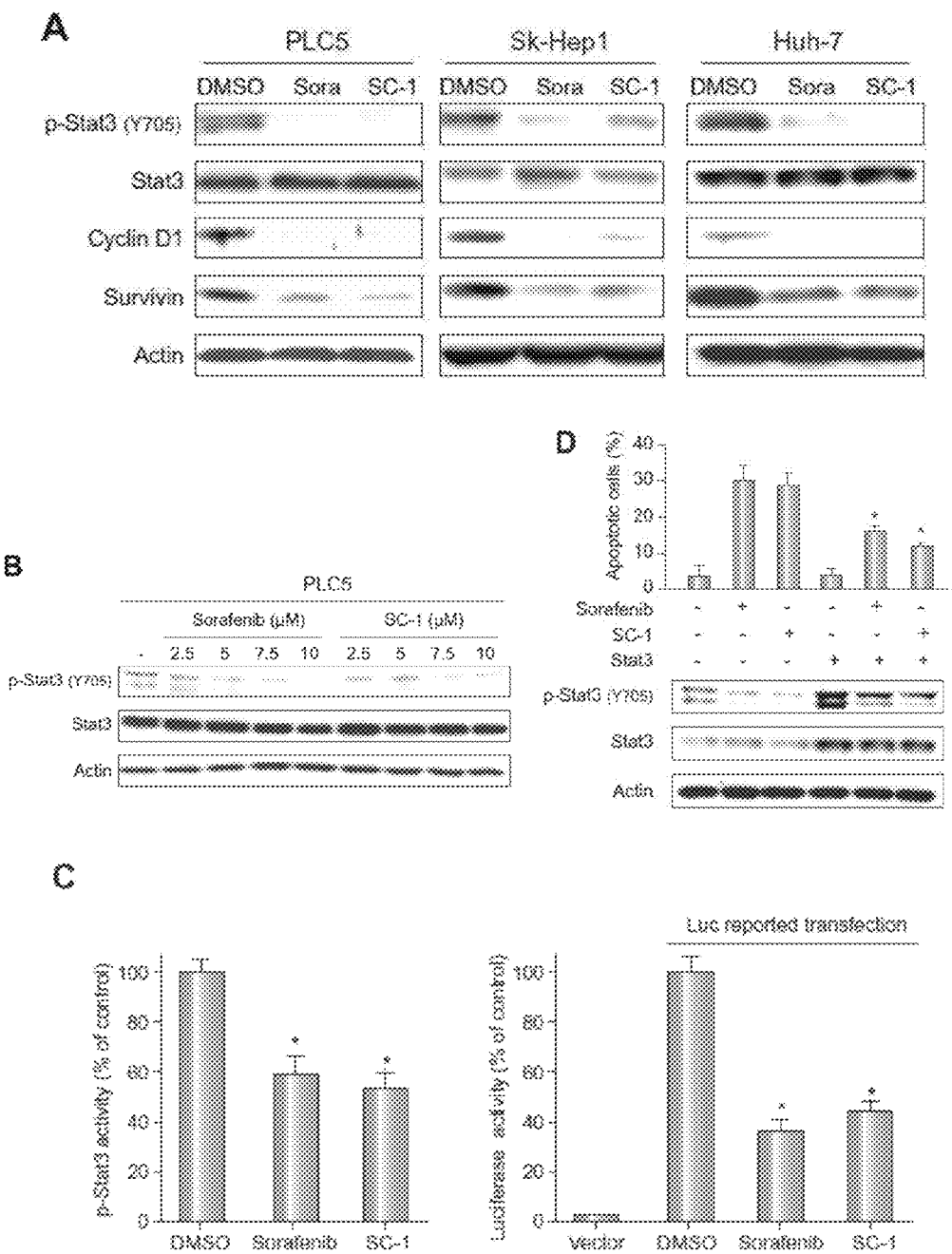
FIG. 9 shows (A) the effects of sorafenib or SC-1 on STAT3-related proteins, wherein cells were treated with sorafenib or SC-1 at 10 μM for 24 h; (B) the dose-escalation effects of sorafenib or SC-1 on phospho-STAT3 in PLC5 cells, wherein cells were treated with drugs at the indicated concentrations for 24 h; (C) the effects of sorafenib and SC-1 on STAT3 activity (left, Phospho-STAT3 ELISA; Right, luciferase reporter assay of STAT3), wherein cells were treated with sorafenib or SC-1 at 10 μM for 24 hs and phospho-STAT3 ELISA or luciferase activity was measured; (D) the protective effects of STAT3 on apoptosis induced by sorafenib in PLC5 cells, wherein cells (wild type or ectopic expression of STAT3) were exposed to sorafenib or SC-1 at 10 μM for 24 h, and apoptotic cells were analyzed by flow cytometry. Columns, mean; bars, SD (n=3). *P<0.05.

To verify whether down-regulation of p-STAT3 is dependent on the kinase inhibition of sorafenib, we further assayed the STAT3-related signaling pathway in SC-1-treated HCC cells. Given the fact that STAT3 was down-regulated by sorafenib and resulted in the induction of cell death, apoptotic related molecules including Mcl-1, cyclinD1, and survivin were examined. We found that suppression of p-STAT3 plays a role in mediating SC-1-induced or sorafenib-induced cell death. SC-1 reduced the expression of STAT3-related proteins in HCC cells. The phosphorylation of STAT3 at tyrosine 705 is critical for STAT3 transactivation. SC-1 as well as sorafenib down-regulated p-STAT3 at Y705 residue and suppressed Mcl-1 and cyclin D1 in all tested HCC cell lines including PLC5, Huh7, and Sk-Hep1 (FIG. 9A). Notably, total STAT3 protein was not affected by sorafenib and SC-1 (FIG. 9A). Moreover, SC-1 and SC-1 down-regulated p-STAT3 in a dose- and time-dependent manner (FIG. 9B). These data further suggest that sorafenib inhibited STAT3 by a kinase-independent mechanism.

We also assayed the activation status of p-STAT3 by STAT3 ELISA. Twenty-four hours before exposure to sorafenib or SC-1, Sk-Hep1 cells were pre-treated with recombinant IL-6 to mimic high expression level of STAT3 and then were treated with SC-1 or sorafenib for another 24 hours under the presence of IL-6. SC-1 or sorafenib-treated cell extracts were incubated with antibody against phosphorylated STAT3 at Y705. The ELISA results showed that sorafenib as well as SC-1 decreased the activity of p-STAT3 significantly (FIG. 9C, left). To evaluate the transcriptional activity, STAT3-binding region was cloned into Luc reporter. We found that transcription activity of STAT3 was significantly decreased in the presence of sorafenib or SC-1 (FIG. 9C, right). The firefly luciferase activity was evaluated and normalized by Renilla luciferase. These results showed that both sorafenib and SC-1 potently reduced the level of phosphorylation of STAT3 through the suppression of transcription. We then established STAT3-overexpressed stable clone of HCC cells to validate the effect of sorafenib in HCC. As shown in FIG. 9D, both sorafenib-induced and SC-1-induced apoptosis were abolished in STAT3-overexpressed HCC cells as evidenced by sub-G1 analysis, suggesting that STAT3 is a major mediator of sorafenib- and SC-1-induced apoptosis.

2.2.6. SHP-1 Phosphatase Plays a Role in the Effect of Sorafenib and SC-1 on Phospho-STAT3 and Apoptosis.

Figure 10:
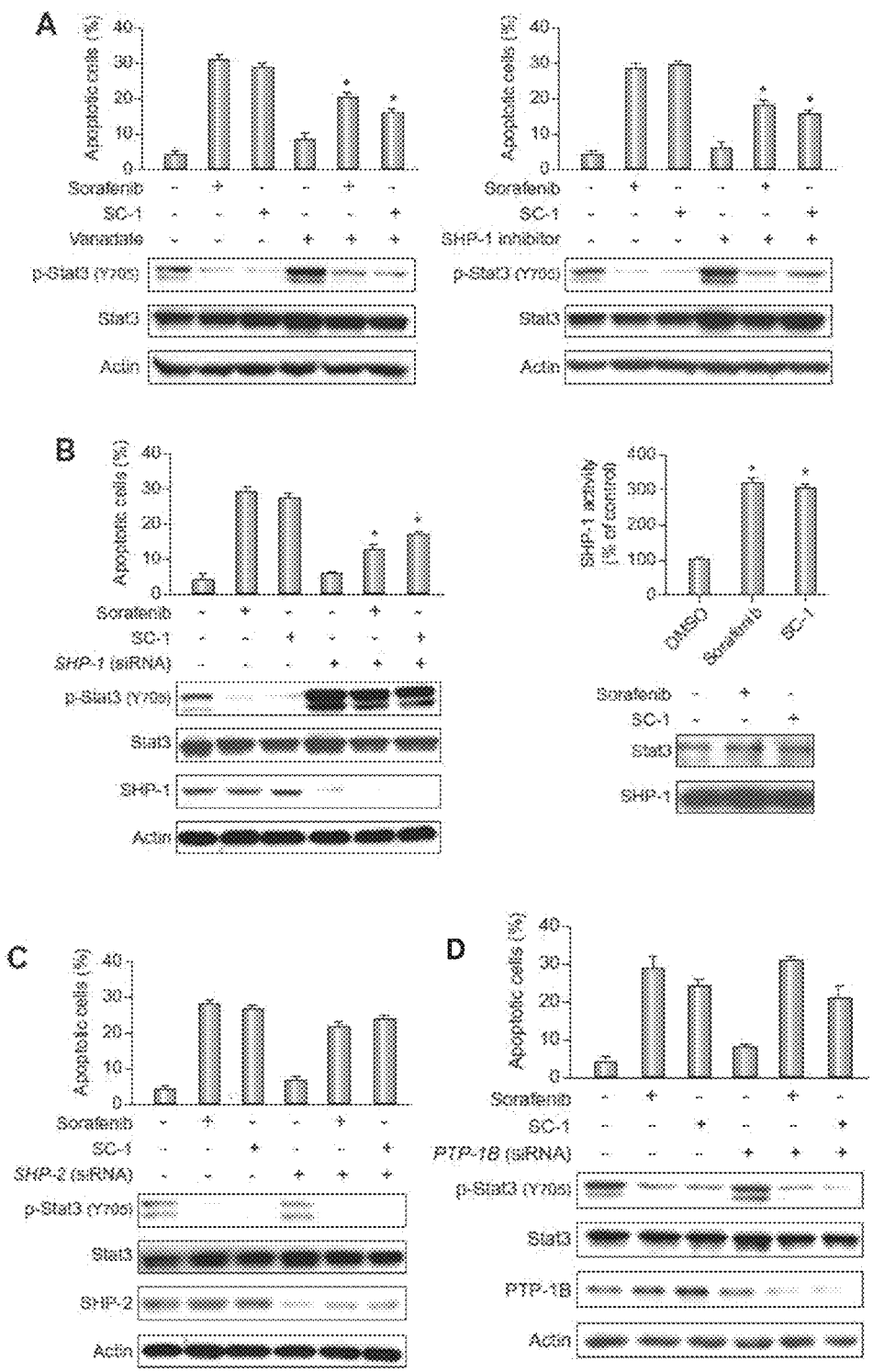
FIG. 10 shows inhibition of SHP-1 reverses effects of sorafenib and SC-1 on phospho-STAT3 and apoptosis. A, left, vanadate, a non-specific phosphatase inhibitor. Right, specific SHP-1 inhibitor. Columns, mean; bars, SD (n=3). *P<0.05. B, left, silencing SHP-1 by siRNA reduces effects of sorafenib or SC-1 on p-STAT3 in HCC cells. PLC5 cells were transfected with control siRNA or SHP-1 siRNA for 24 h then treated with sorafenib or SC-1 for another 24 h. Middle, the activity of SHP-1 in PLC5 cells. Columns, mean; bars, SD (n=3). *P<0.05. Right, effects of sorafenib or SC-1 on protein interactions between SHP-1 and STAT3. PLC5 cells were treated with sorafenib or SC-1 at 10 μM for 24 hours. C, knock-down of SHP-2 does not affect the effects of sorafenib or SC-1 on p-STAT3 and apoptosis. D, knock-down of PTP-1B does not affect effects of sorafenib on p-STAT3 and apoptosis. PLC5 cells were transfected with control siRNA or SHP-2 siRNA or PTP-1B siRNA for 24 h then treated with sorafenib or SC-1 at 10 μM for 24 h.

To further study how sorafenib inhibits STAT3 in HCC, we examined several protein phosphatases which may involved in regulating p-STAT3. Our results showed that sodium vanadate, a general phosphatase inhibitor, decreased apoptosis and increased p-STAT3 (FIG. 10A, left). These data suggest that sorafenib and SC-1 may affect p-STAT3 by targeting STAT3-related protein phosphatases. Furthermore, we found that SHP-1 phosphatase-specific inhibitor reversed sorafenib-induced cell death and inhibition of p-STAT3 (FIG. 10A, right). To further verify the role of SHP-1 in SC-1 and sorafenib-induced inhibition of p-STAT3, we applied siRNA specific to SHP-1 to examine the influence of sorafenib and SC-1. We found that silencing of SHP-1 reversed sorafenib- or SC-1-induced apoptosis and inhibition of p-STAT3 (FIG. 10B, left). In addition, both sorafenib and SC-1 increased SHP-1 activity up to 3-fold in comparison with control cells (P<0.05) (FIG. 10B, middle). Sorafenib or SC-1-treated PLC5 cells were immunoprecipitated by SHP-1 specific antibody, and then SHP-1-containing complex underwent fluorescence-based phospho-group assay. Notably, neither sorafenib nor SC-1 affected the interaction of STAT3 and SHP-1 as evidenced by SHP-1 immunoprecipitation (FIG. 10B, right). These data suggest that sorafenib induced cell death through SHP-1-dependent STAT3 inactivation.

In addition to SHP-1, other phosphatases such as SHP-2 and PTP-1B, have been reported to regulate p-STAT3. As shown in FIG. 10C, the effects of sorafenib on apoptosis and p-STAT3 were not reversed by silencing SHP-2 or PTP-1B, suggesting that neither SHP-2 nor PTP-1B played a role in mediating the effect of sorafenis or SC-1 on p-STAT3.

2.2.7. SC-1 Down-Regulates p-STAT3 and Induces Apoptosis in HUVEC Cells.

Figure 11:
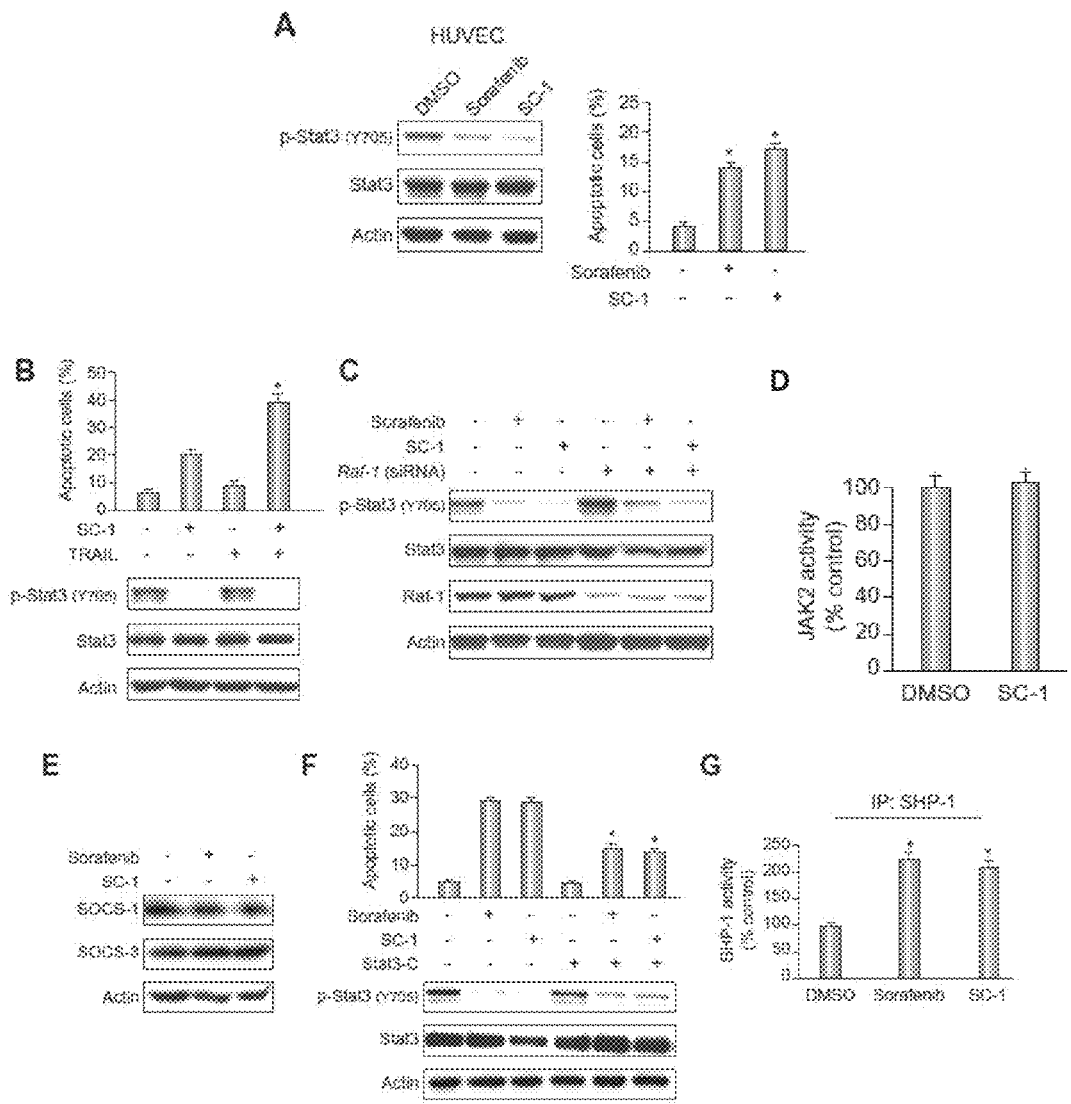
FIG. 11 shows that SC-1 down-regulates p-STAT3 and induces apoptosis in HUVEC cells. A, effects of sorafenib or SC-1 on p-STAT3 (left) and apoptosis (right) in HUVEC cells. Cells were exposed to sorafenib or SC-1 at 10 μM for 24 h. Apoptotic cells were assayed by flow cytometry (sub-G1). B, effects of SC-1 on TRAIL sensitization in HCC. PLC5 cells were treated with SC-1 (10 μM) and/or TRAIL (100 ng/ml) for 24 h. C, silencing Raf-1 does not affect the effects of the drugs on p-STAT3. PLC5 cells were transfected with control siRNA or Raf-1 siRNA for 24 h then treated with sorafenib or SC-1 at 10 μM for 24 h. D, effect of sorafenib and SC-1 on JAK2 activity. PLC5 cells were exposed to sorafenib or SC-1 at 10 μM for 24 h. Points, mean; bars, SD (n=6). E, effects of sorafenib and SC-1 on SOLS-1 and SOLS-3. Sk-Hep1 cells were pre-treated with IL-6 for 24 h then were treated with sorafenib or SC-1 at the indicated doses for another 24 h in the presence of IL-6. F, effects of STAT-C on apoptosis induced by SC-1 in PLC5 cells. Cells (wild type or ectopic expression of STAT3-C) were exposed to sorafenib or SC-1 at 10 μM for 24 h. G, effects of sorafenib and SC-1 on SHP-1. Columns, mean; bars, SD (n=3). *P<0.05.

To clarify the effect of sorafenib on p-VEGFR2, a key target of sorafenib in cancer treatment, we examined the effect of sorafenib and SC-1 in HUVEC cells. As shown in FIG. 11A, left, sorafenib and SC-1 both down-regulated p-STAT3 in HUVEC cells and induced significant apoptotic cell death in HCC (P<0.05). Notably, sorafenib but not SC-1 down-regulated the phosphorylation of VEGFR in HUVEC cells (FIG. 7A, middle). These results indicate that neither Raf-1 nor VEGFR mediates the effect of sorafenib on apoptosis and p-STAT3.

Previous study has also suggested that Mc1-1 is crucial in mediating the effect of sorafenib on TRAIL-sensitization. Interestingly, our data showed that SC-1 also showed similar enhancement of TRAIL-induced apoptosis in HCC by the down-regulation of p-STAT3 (FIG. 11B). To further investigate whether inhibition of p-STAT3 by sorafenib is associated with Raf-1, we knocked down Raf-1 by using small interference RNA. Silencing Raf-1 did not affect the effects of sorafenib or SC-1 on p-STAT3 (FIG. 11C), indicating that Raf-1 does not mediate the effect of sorafenib on p-STAT3. Notably, neither sorafenib nor SC-1 altered the kinase activity of JAK2 (FIG. 11D), suggesting that JAK2 does not mediate effects of both compounds on p-STAT3. In addition, our data showed that sorafenib and SC-1 did not affect the protein levels of SOLS-1 and SOLS-3 (FIG. 11E). Interestingly, HCC cells with constitutively active STAT-3 (STAT3-C) were not completely resistant to SC-1 (FIG. 11F). As SC-1 enhanced the activity of SHP-1 (FIG. 11B, middle), our data suggest that besides STAT-3, other SHP-1-related molecules may also play a role in mediating the effect of SC-1. To examine whether sorafenib or SC-1 targets SHP-1 directly, PLC5 cells were immunoprecipitated with SHP-1 antibody then incubated with sorafenib or SC-1 for 6 hours. As shown in FIG. 11G, sorafenib and SC-1 increase the activity of SHP-1 in these lysates, suggesting that sorafenib and SC-1 targets SHP-1 directly.

2.2.8. Therapeutic Evaluation of Effect of SC-1 and Sorafenib on Huh7-Bearing Mice.

Figure 12:
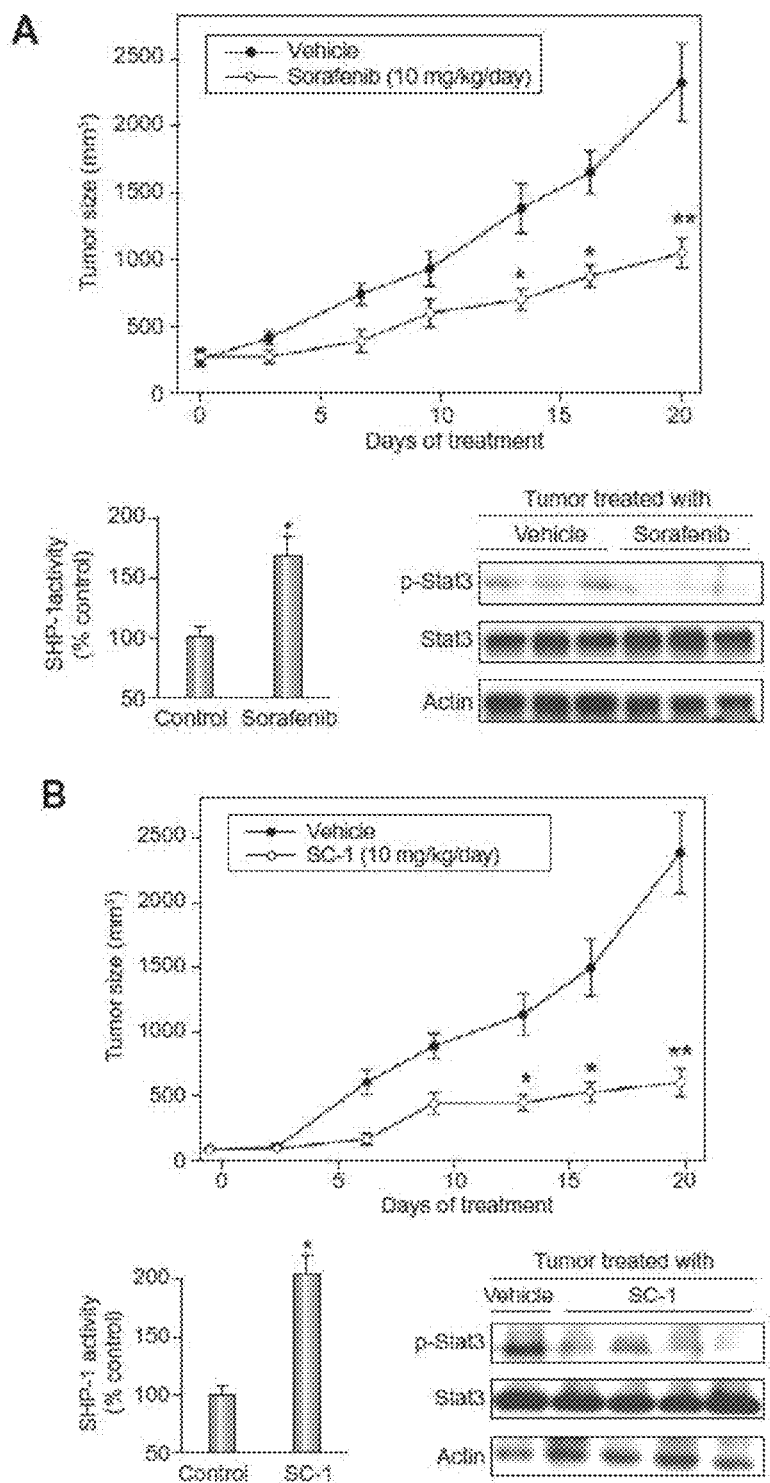
FIG. 12 shows in vivo effect of sorafenib and SC-1 on Huh-7 xeonograft nude mice A, sorafenib shows antitumor effect on Huh-7 tumors. Left, points, mean (n=6); bars, SE. *, P<0.05; **, P<0.01. Right Upper, western blot analysis of p-STAT3 and STAT3 in Huh-7 tumors. Right Lower, the activity of SHP-1 in Huh-7 tumors. B, SC-1 shows a significant antitumor effect on Huh-7 tumors. Left, points, mean (n=6); bars, SE. Right Upper, western blot analysis of p-STAT3 and STAT3 in Huh-7 tumors. Right Lower, the activity of SHP-1 in Huh-7 tumors.

To verify the therapeutic effect of SC-1, we further applied SC-1 to HCC xenograft to evaluate its significance in vivo. First, Huh7-bearing mice received daily treatment with vehicle or sorafenib at the dose of 10 mg/kg/day orally. Sorafenib treatment significantly inhibited Huh7 xenograft tumor growth and sorafenib-treated animals had a tumor-size of less than half that of control mice (FIG. 12A, left). There were no apparent differences in body weight or toxicity in any mice (data not shown). In addition, tumor extract from vehicle and sorafenib-treated mice were immunoblotted for p-STAT3. p-STAT3 was down-regulated in sorafenib-treated tumor (FIG. 12A, right). p-STAT3/STAT3 was observed in the homogenates of three representative Huh7 tumors. Furthermore, we examined SHP-1 activity in sorafenib-treated Huh7 xenograft. Sorafenib treated tumor showed significant induction of SHP-1 activity in vivo (FIG. 12A, right). Taken together, these results confirmed that sorafenib could increase SHP-1 activity to repress p-STAT3 involved in tumor inhibition in the HCC xenograft model.

In addition, treatment with SC-1 had a strong inhibitory effect (P<0.05) and tumor size in this group was only 25% that of vehicle-treated mice at the end of treatment (FIG. 12B, left) Immunoblot for p-STAT3 and SHP-1 activity assay were also performed on a tumor sample from SC-1-treated animals. Interestingly, SC-1 induced significant rising of SHP-1 activity and down regulated p-STAT3 (FIG. 12B, right). These data indicate that SC-1, a SHP-1 agonist and a STAT3 inhibitor, exhibit therapeutic effects in inhibiting tumor growth.

2.2.9. Inhibition of Cancer Cell Growth

Figure 13:
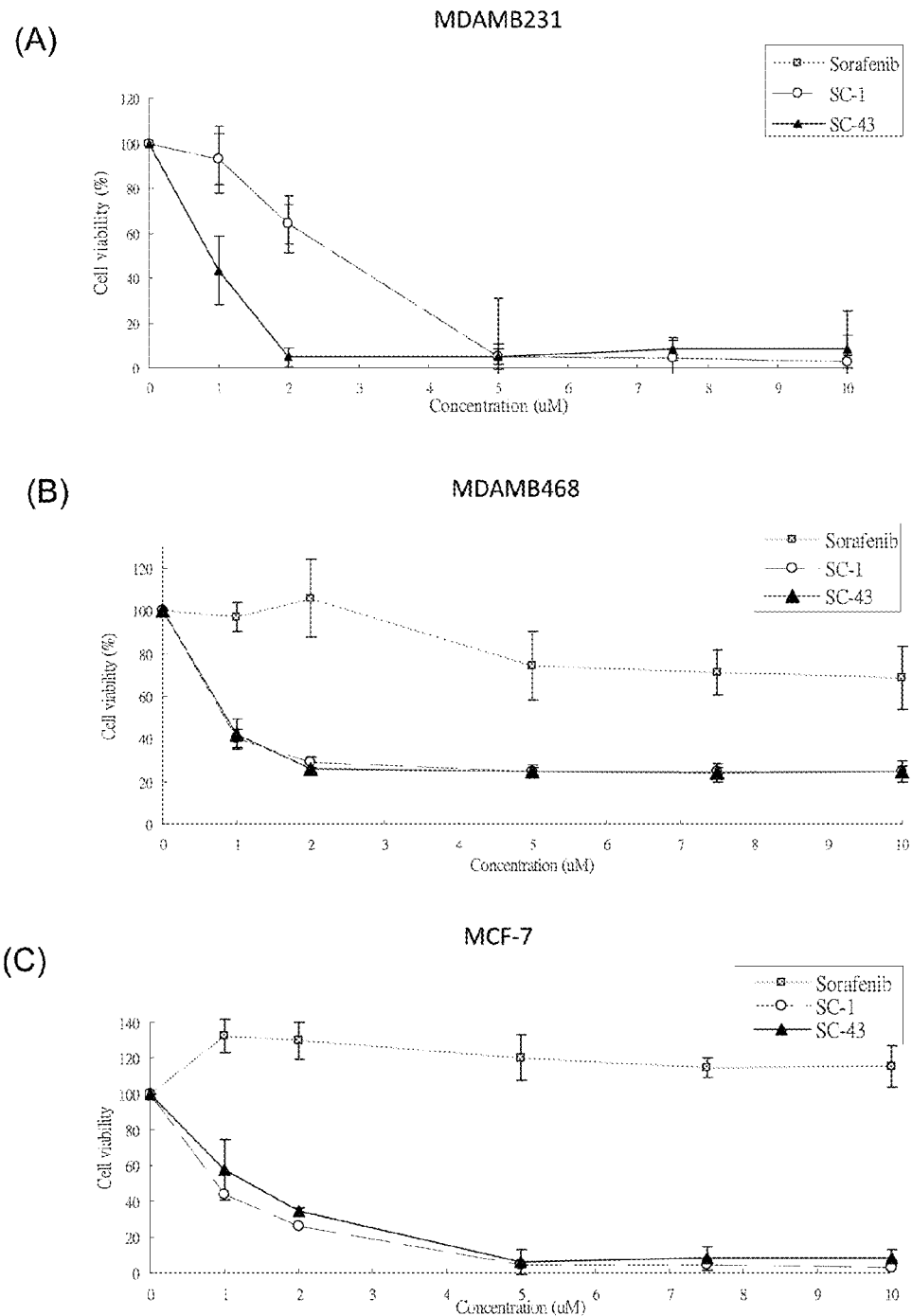
FIG. 13 shows the anti-proliferation effects of SC-1 and SC-43 in various cancer cell lines, including breast cancer cell lines (A) MDAMB231, (B) MDAMB468 and (C) MCF-7, and leukemia cancer cell lines (D) HL-60, (E) KG-1, and (F) ML-1.
Figure 13:
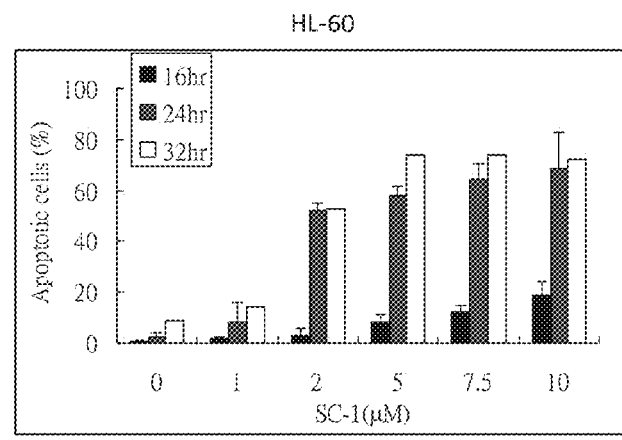
Figure 13:
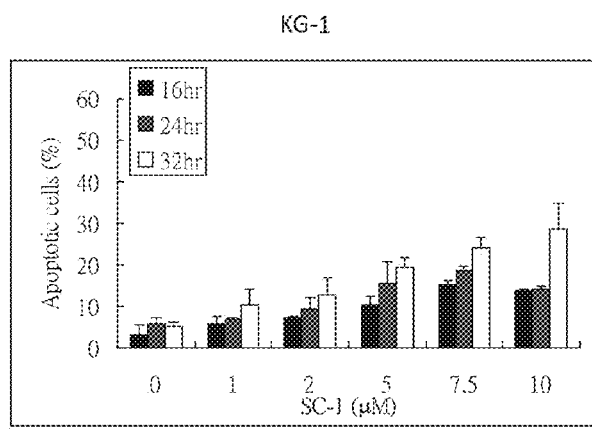
Figure 13:
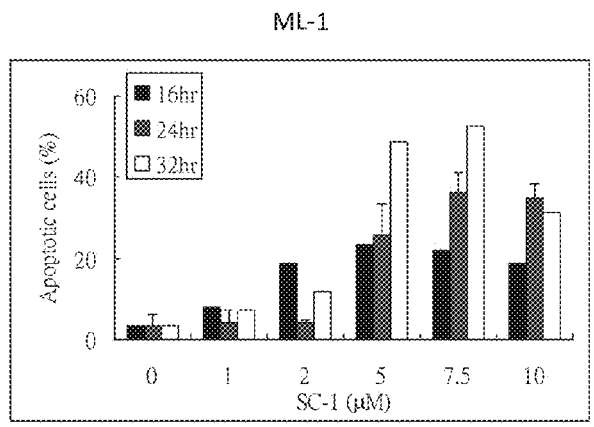

We also examed the effects of SC-1 and SC-43 in other cancer cell lines, including breast cancer cell lines e.g. MDAMB231, MDAMB468, MCF-7, and leukemia cancer cell lines e.g. HL-60, KG-1 and ML-1. FIG. 13 shows the results. These data show that the compounds of the invention are effective in inhibiting the growth of cancer cells.

2.2.10 Anti-Cancer Effects in HCC Cells

Figure 14:
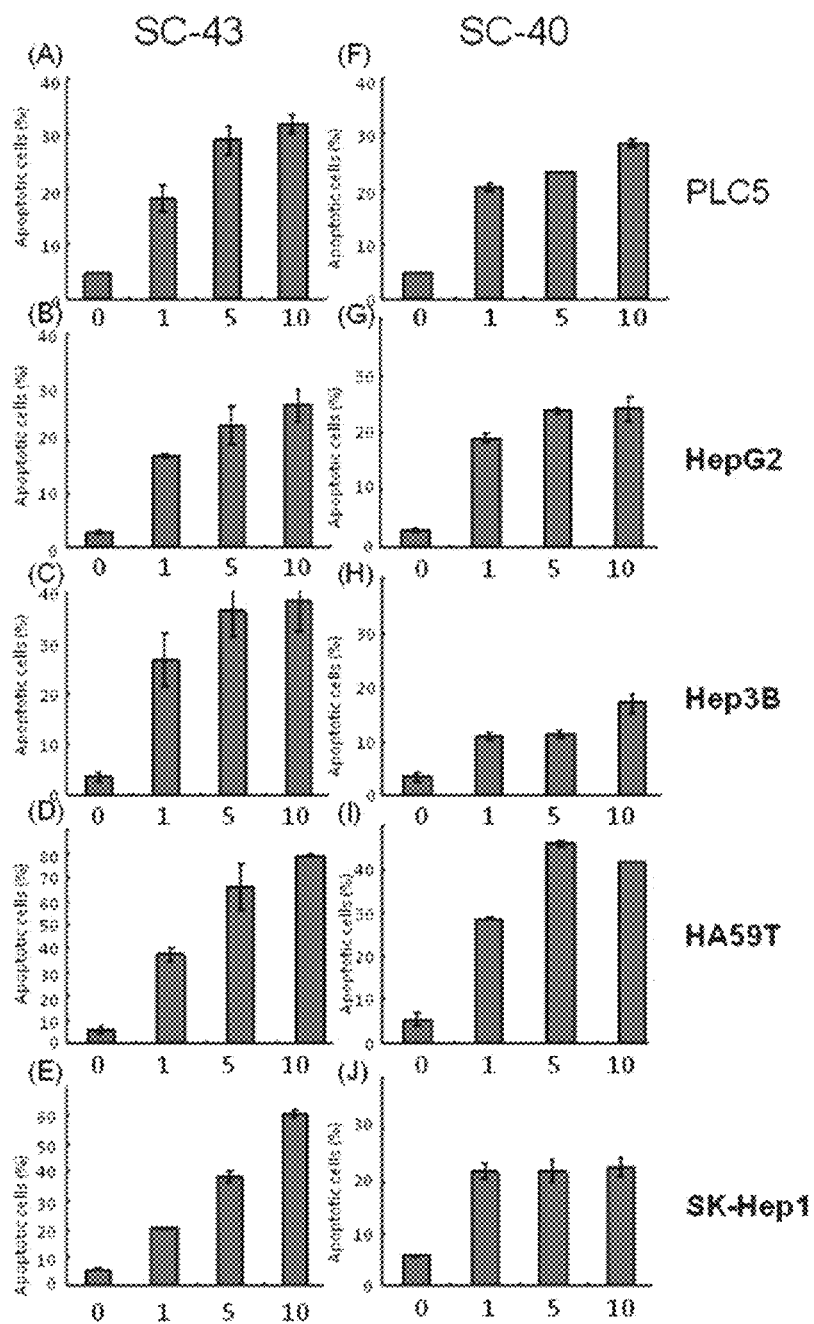
FIG. 14 shows that Sorafenib derivatives induce significant apoptosis in a dose-dependent manner, where (A), (B), (C), (D) and (E) refer to SC-43 for PLC5, HepG2, Hep3B, HA59T and SK-Hep1 cells, respectively; and (F), (G), (H), (I) and (J) refer to SC-40 for PLC5, HepG2, Hep3B, HA59T and SK-Hep1 cells, respectively. Points, mean; bars, SD (n=6).

HCC cells were treated with sorafenib derivatives (SC-43 or SC-40) at the indicated dose for 24h. Collected cells were fixed in 75% Ethanol and stained with 20 ug/ml Propidium Iodide (PI). Sub-G1 analysis was performed by flow-cytometry. FIG. 14 shows that SC-43 and SC-40, sorafenib derivatives, show significant anti-cancer effects in HCC cells, (A), (B), (C), (D) and (E) refer to SC-43 for PLC5, HepG2, Hep3B, HA59T and SK-Hep1 cells, respectively; and (F), (G), (H), (I) and (J) refer to SC-40 for PLC5, HepG2, Hep3B, HA59T and SK-Hep1 cells, respectively. Points, mean; bars, SD (n=6).

2.2.11 Effects of Sorafenib or SC-43 on STAT3-Related Proteins

Figure 15:
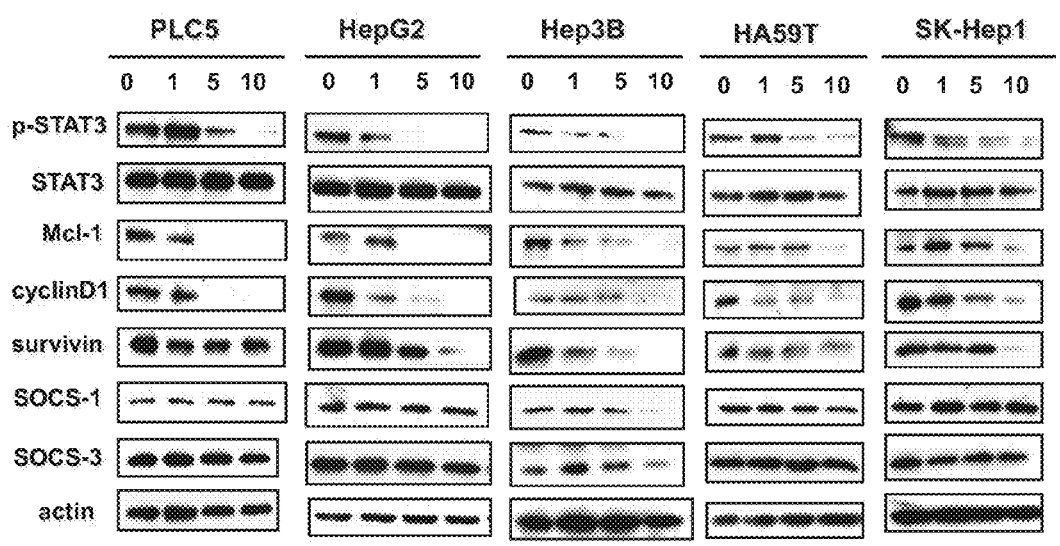
FIG. 15 shows that that SC-43 down-regulates phospho-STAT3-related signaling pathway in HCC cells, including PLC5, HepG2, Hep3B, HA59T and SK-Hep1 cells.

HCC cells treated with SC-43 (10 μM for 24 h) were collected with RIPA lysis buffer. Antibodies for immunoblotting such as cyclin D1 was purchased from Santa Cruz Biotechnology. Other antibodies such as survivin, phospho-STAT3 (Tyr705), STAT3, Mc1-1, SOCS1, and SOCS3 were from Cell Signaling. FIG. 15 shows that SC-43 down-regulates phospho-STAT3-related signaling pathway in HCC.

2.2.12 Effects of Sorafenib or SC-40 on STAT3-Related Proteins

Figure 16:
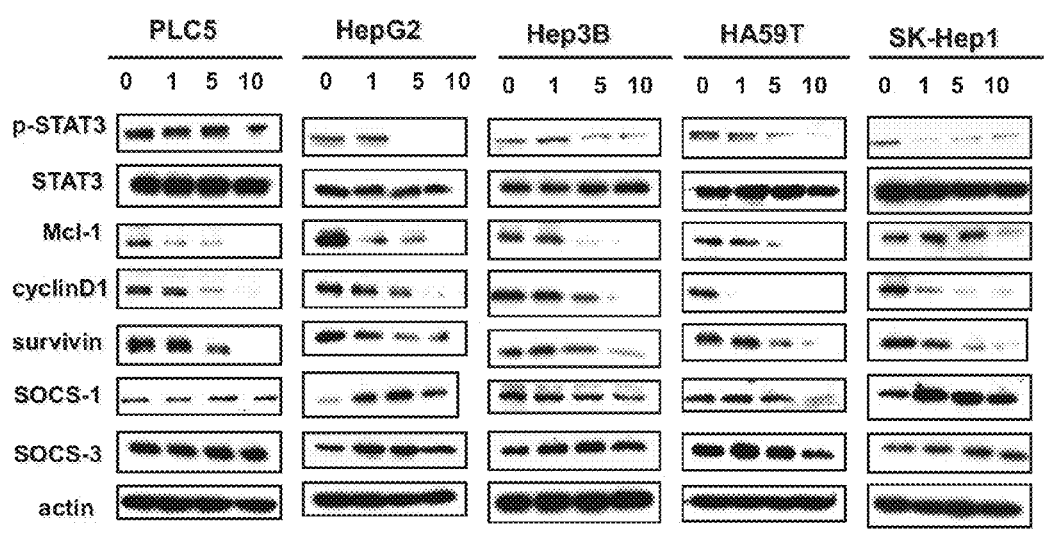
FIG. 16 shows that SC-40 down-regulates phospho-STAT3-related signaling pathway in HCC, cells, including PLC5, HepG2, Hep3B, HA59T and SK-Hep1 cells.

HCC cells treated with SC-40 (10 μM for 24 h) were collected with RIPA lysis buffer. Antibodies for immunoblotting such as cyclin D1 were purchased from Santa Cruz Biotechnology. Other antibodies such as survivin, phospho-STAT3 (Tyr705), STAT3, Mc1-1, SOCS1, and SOCS3 were from Cell Signaling. FIG. 16 shows that SC-40 down-regulates phospho-STAT3-related signaling pathway in HCC.

2.2.13 Effects of Sorafenib or SC-43 on STAT3-Related Proteins

Figure 17:
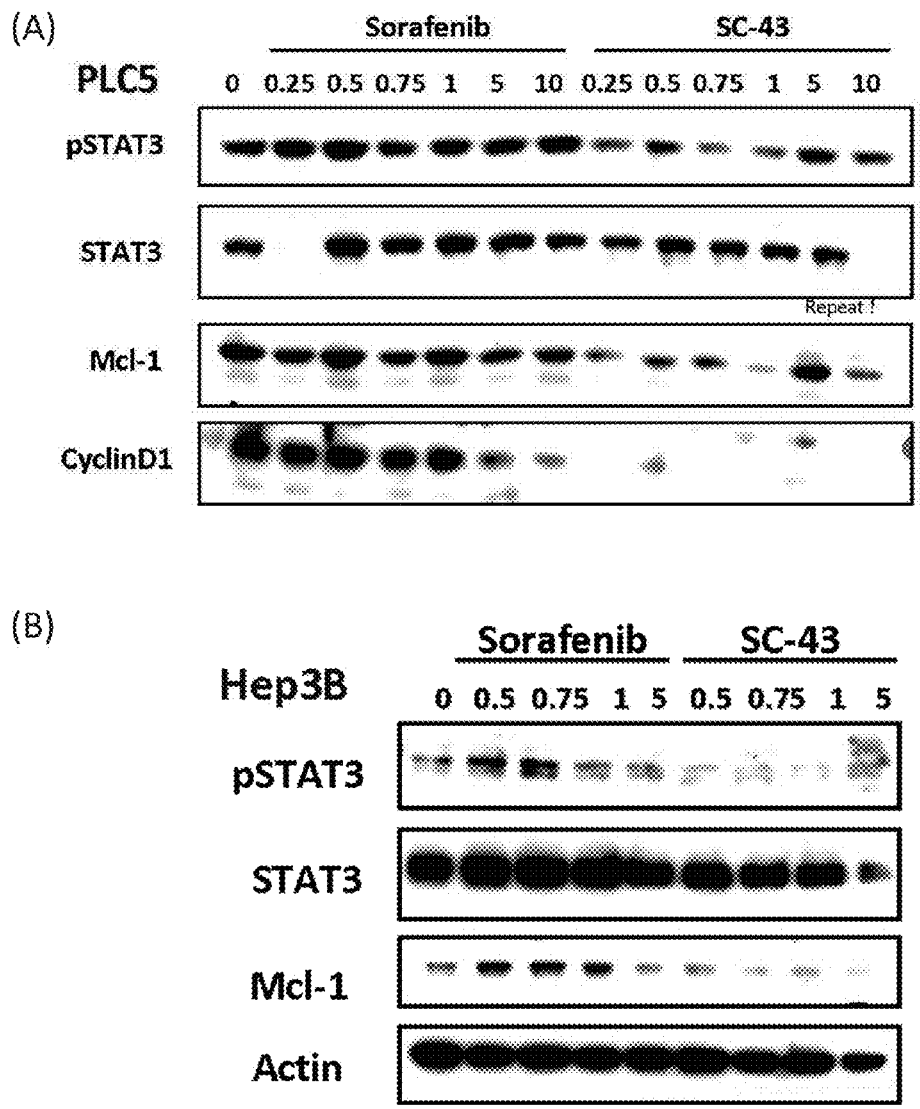
FIG. 17 shows that SC-43 shows better inhibition of p-STAT3-related signaling pathway than sorafenib in HCC cells, (A) PLC5 and (B) Hep 3B.

HCC cells treated with SC-43 (10 μM for 24 h) were collected with RIPA lysis buffer. Antibodies for immunoblotting such as cyclin D1 were purchased from Santa Cruz Biotechnology. Other antibodies such as survivin, phospho-STAT3 (Tyr705), STAT3, and Mc1-1 were from Cell Signaling. FIG. 17 shows that SC-43 shows better inhibition of p-STAT3-related signaling pathway than sorafenib in HCC, (A) PLC5 and (B) Hep 3B. SC-43 shows significant inhibition of p-STAT3-related proteins at low dose treatment than sorafenib.

2.2.14 Effects of SC-43 and SC-40 on STAT3 Activity p-STAT3 activity: PLC5 cells treated with SC derivatives were collected in RIPA buffer and analyzed in p-STAT3 ELISA kit. The assay protocol follows the manufacturer.

STAT3 reporter assay: PLC5 cells were seeded in a 96-well plate. Cells were pretransfected with STAT3 reporter construct for 24 h and treated with derivatives for another 24 h. The STAT3 Reporter Kit was purchased from SABiosciences.

Figure 18:
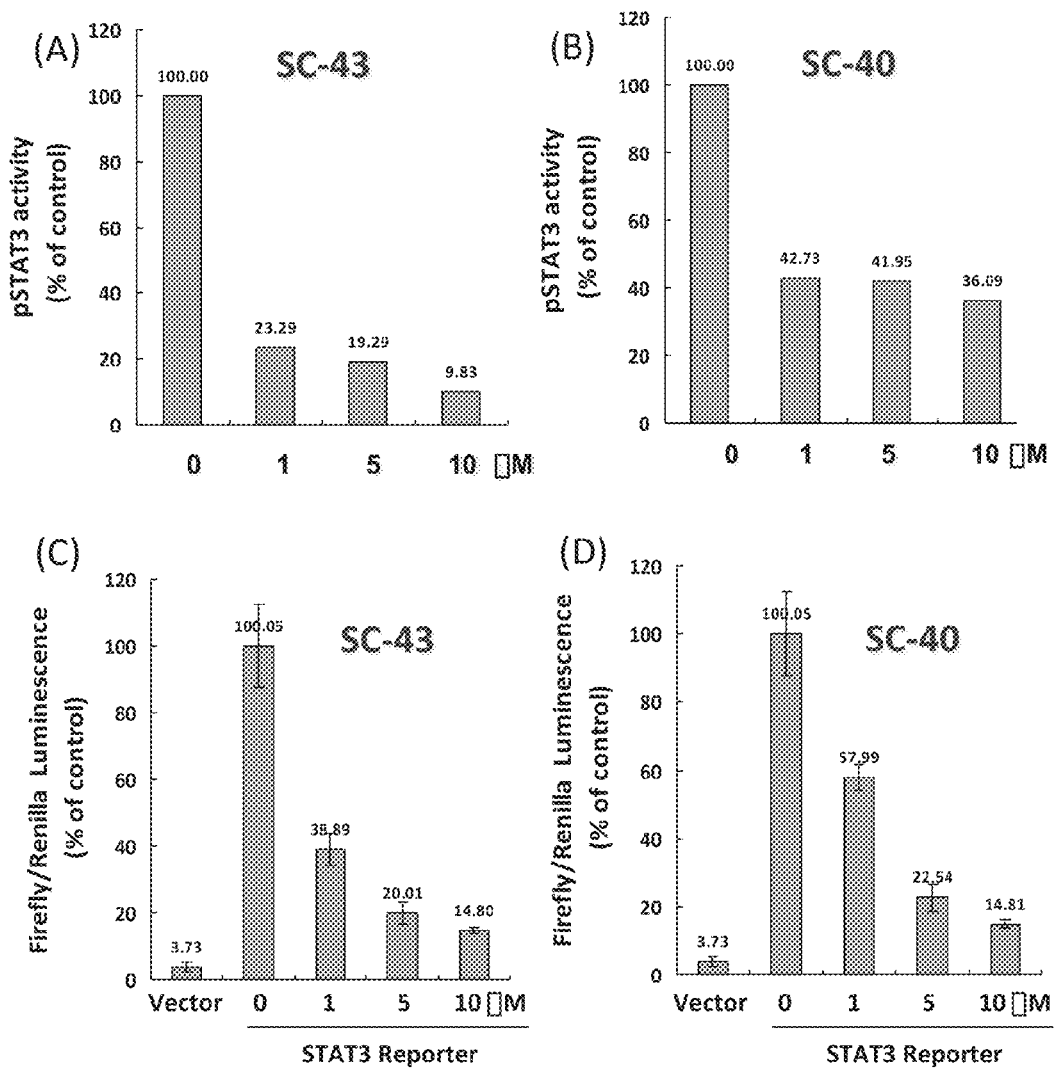
FIG. 18 shows that both SC-43 and SC-40 induce strong inhibition of p-STAT3 activity (A) and (B) p-STAT3 ELISA for SC-43 and SC-40, respectively, and (C) and (D) STAT3 reporter assay for SC-43 and SC-40, respectively.

Cells were treated with SC-43 or SC-40 at 10 μM for 24 h and phospho-STAT3 ELISA or luciferase activity was measured. FIG. 18 shows that both SC-43 and SC-40 induce strong inhibition of p-STAT3 activity, (A) and (B) p-STAT3 ELISA for SC-43 and SC-40, respectively, and (C) and (D) STAT3 reporter assay for SC-43 and SC-40, respectively.

2.2.15 Effects of SC-43/40 on Phosphatase Activity

Figure 19:
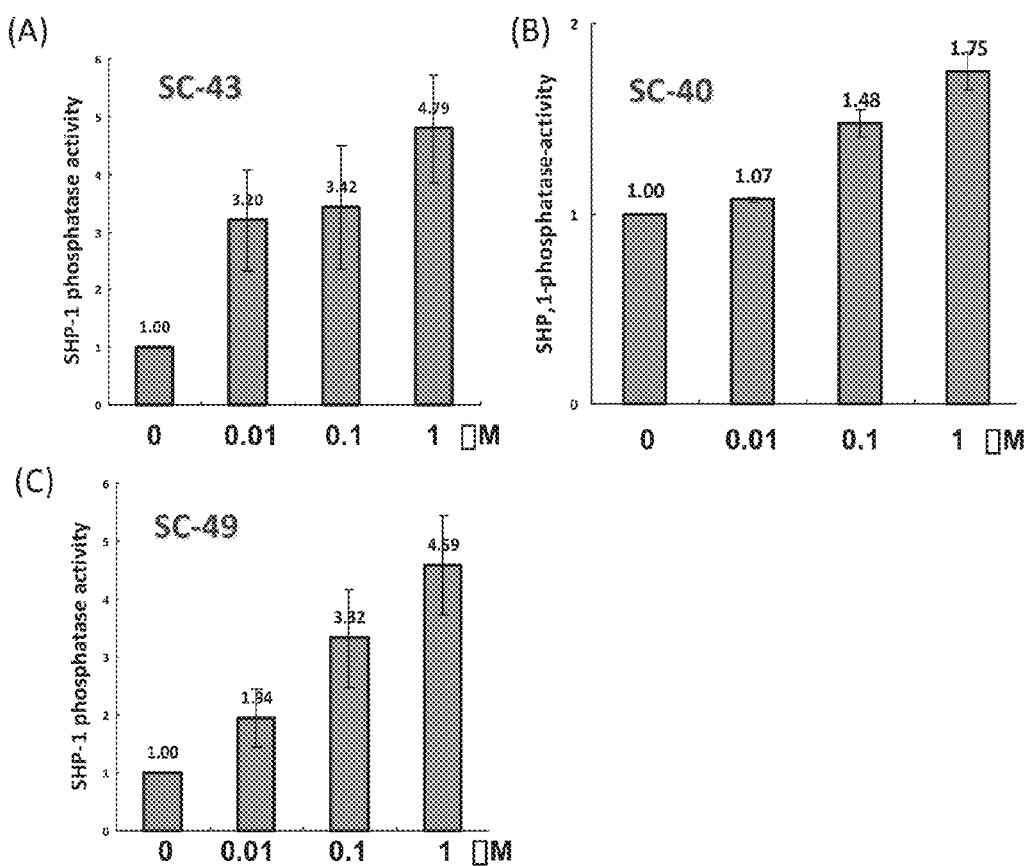
FIG. 19 shows that the SC derivatives increase phosphatase activity of SHP-1 in vitro, (A)SC-43, (B)SC-40, and (C)SC-49.

PLC5 protein extract was incubated with anti-SHP-1 antibody in immunoprecipitation buffer overnight. Protein G Sepharose 4 Fast flow (GE Healthcare Bio-Science) was added to each sample, followed by incubation for 3 hours at 4° C. with rotation. This SHP-1-containing protein extract were further incubated with SC compounds (10 or 100 nmol/L) for 30 min at 4° C. RediPlate 96 EnzChek Tyrosine Phosphatase Assay kit (R-22067) was used for SHP-1 activity assay (Molecular Probes). FIG. 19 shows that the SC derivatives increase phosphatase activity of SHP-1 in vitro, (A)SC-43, (B)SC-40, and (C)SC-49.

2.2.16 Effects of SC Derivatives on Phosphatase Activity in Recombinant SHP-1

RediPlate 96 EnzChek Tyrosine Phosphatase Assay kit (R-22067) was used for SHP-1 activity assay (Molecular Probes). Recombinant SHP-1 protein (25 ng) was incubated with either SC-43 or SC-40 at the indicated dose for 30 minutes and then analyzed by SHP-1 phosphatase activity.

Figure 20:
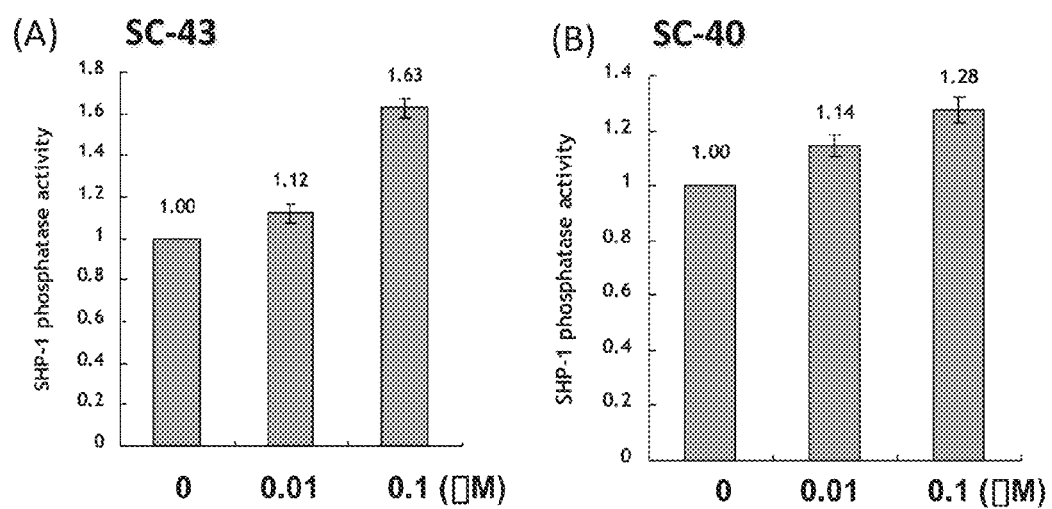
FIG. 20 shows that the SC derivatives increase phosphatase activity of SHP-1 in vitro, (A)SC-43 and (B)SC-40.

FIG. 20 shows that the SC derivatives increase phosphatase activity of SHP-1 in vitro, (A)SC-43 and (B)SC-40.

2.2.17 In Vivo Effect of SC-40 on PLC5-Bearing Xenograft

Male NCr athymic nude mice (5-7 weeks of age) were obtained from the National Laboratory Animal Center (Taipei, Taiwan). All experimental procedures using these mice were done in accordance with protocols approved by the Institutional Laboratory Animal Care and Use Committee of National Taiwan University. Each mouse was inoculated s.c. in the dorsal flank with 1×106 PLC5 cells suspended in 0.1 mL of serum-free medium containing 50% Matrigel (BD Biosciences). When tumors reached 100 to 200 mm3, mice received SC-40 tosylate (10 or 20 mg/kg) orally once daily. Tumors were measured weekly using calipers, and their volumes were calculated using the following standard formula: width×length×height×0.52.

Figure 21:
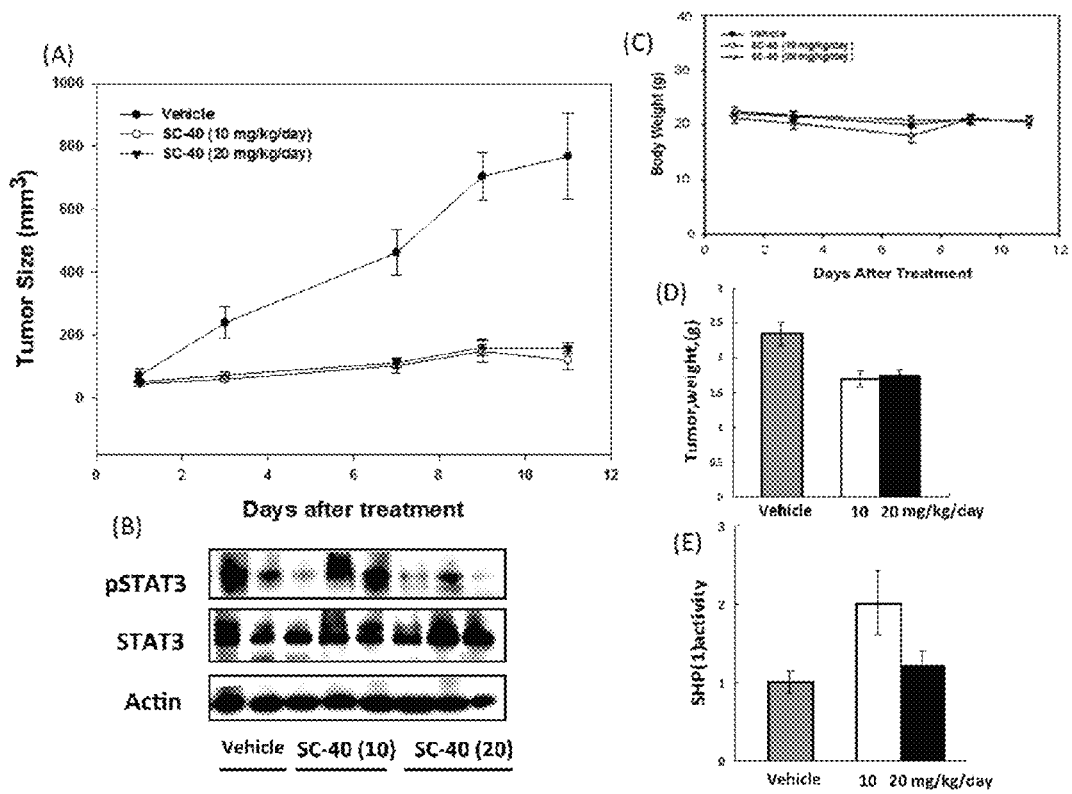
FIG. 21 shows that (A) the antitumor effect of SC-40 on PLC5 tumors; (B) Western blot analysis of p-STAT3 and STAT3 in PLC5 tumors; (C) the body weight of the animals; and (D) the tumor weight and (E) activity of SHP-1 in PLC5 tumors. Points, mean (n=6); bars, SE

FIG. 21 shows that (A) the antitumor effect of SC-40 on PLC5 tumors; points, mean (n=6); bars, SE; (B) Western blot analysis of p-STAT3 and STAT3 in PLC5 tumors; (C) the body weight of the animals; and (D) tumor weight and (E) activity of SHP-1 in PLC5 tumors. The results show that SC-40 has significant anti-tumor effect on PLC5 tumors, but do not affect body weight of the animals. The body weight has no significant differences between control and SC-40-treated mice.

2.2.18 Antitumor Effect of SC-43

Figure 22:
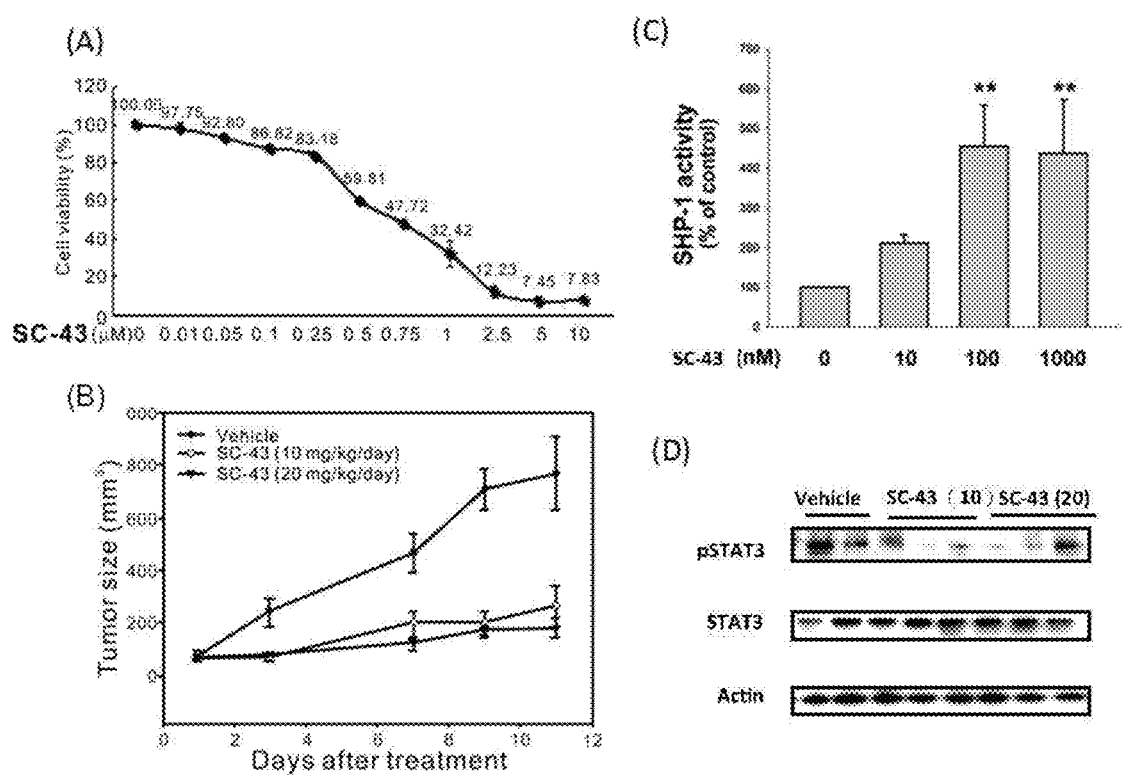
FIG. 22 shows that SC-43 exhibits antitumor effect in vitro and in vivo, (A) the cytotoxicity of SC-43 in HCC cells, (B) the antitumor effect of SC-43 in HCC-bearing mice, (C) the activity of SHP-1 induced by SC-43, and (D) Western blot analysis of p-STAT3 and STAT3 in HCC cells treated by SC-43 (10 μM and 20 μM).

In this example, we show that SC-43 exhibits antitumor effect in vitro and in vivo. SC-43 shows a significant cytotoxicity in HCC cells (IC50~0.5 μM). Also, SC-43 significantly causes tumor growth inhibition in HCC-bearing mice. SHP-1/STAT3-related signaling pathway acts as a vital target for the anti-tumor effect of SC-43. See FIG. 22 (A) the cytotoxicity of SC-43 in HCC cells, (B) the antitumor effect of SC-43 in HCC-bearing mice, (C) the activity of SHP-1 induced by SC-43, and (D) Western blot analysis of p-STAT3 and STAT3 in HCC cells treated by SC-43 (10 μM and 20 μM).

Figure 23:
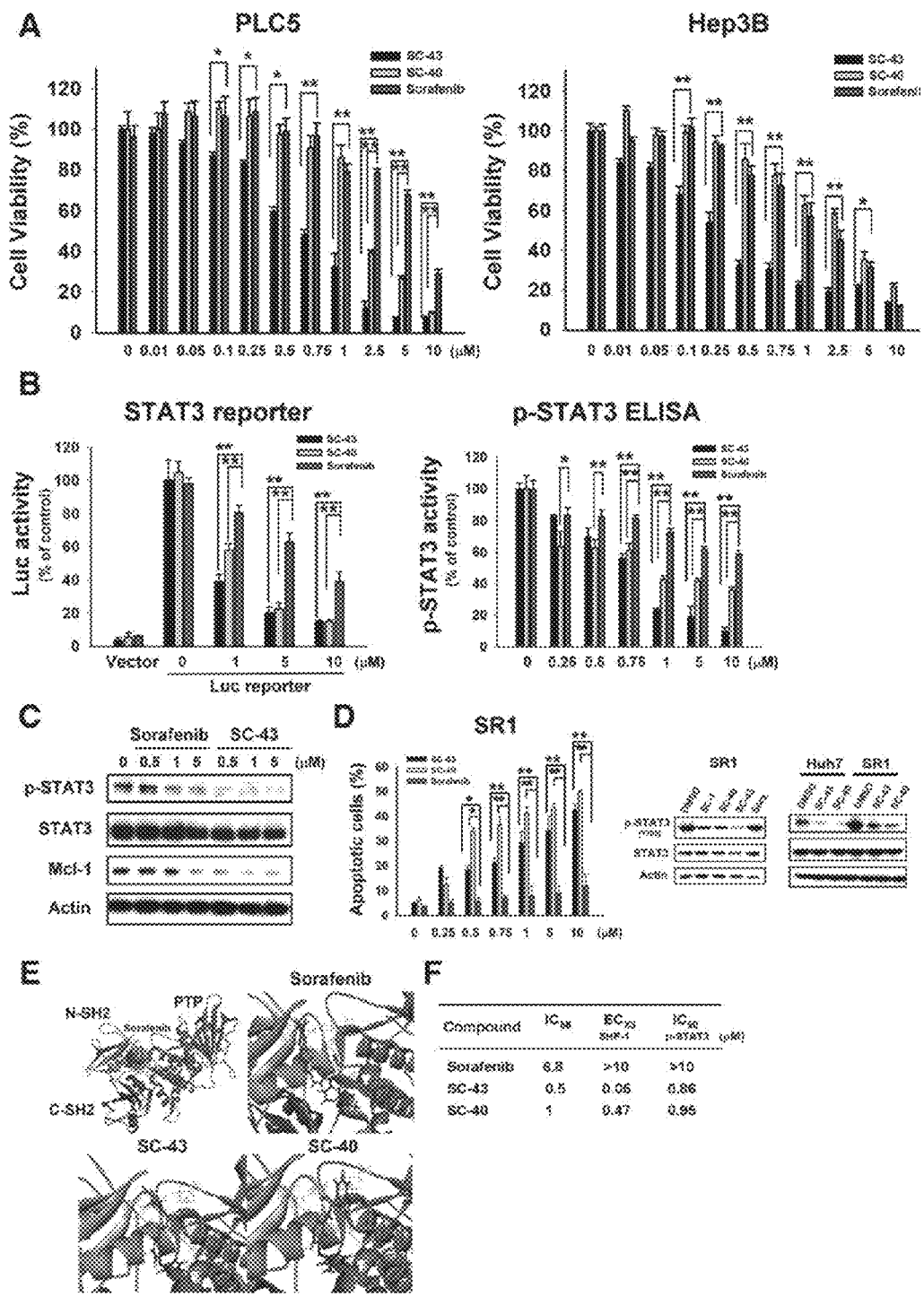
FIG. 23 shows that SC-43 and SC-40 have a significant anti-HCC effect and overcome the resistance of sorafenib. (A)SC-43 and SC-40 showed significant cytotoxicity in HCC cells, compared to sorafenib. Cells were exposed to SC derivatives or sorafenib at indicated doses for 72 hours, and cell viability was assessed by methyl thiazolyl tetrazolium assay. Points, mean; bars, SD (n 5 8). (B) Both SC-43 and SC-40 showed superior inactivation of p-STAT3, compared to sorafenib, in p-STAT3 ELISA and reporter assay. (C) Dose-dependent effect of SC-43 and sorafenib on down-regulation of p-STAT3 and associated protein Mc1-1. (D)SC-43 and SC-40 resulted in significant sorafenib-resistant HCC cell (SR1) death. Cells that were resistant to sorafenib were not resistant to SC derivatives. (E) Modeled docking of sorafenib, SC-43, and SC-40 into the N-SH2 site of SHP-1 (pdb code: 3PS5). The N-SH2 domain is in orange, the C-SH2 domain is in marine, the PTP domain is in hot pink, and the linkers between them are in gray. The small-molecule docking site (by CDOCKER), which is labeled by a transparent red circle, is around the N-SH2 domain and C-terminal residues. Sorafenib forms a hydrogen bond (shown in green dashed lines) with R44. The -CDOCKER interaction energy (CDOCKER docking score) is 32.48. SC-43 forms one hydrogen bond with Q529. The -CDOCKER interaction energy is 37.81. SC-40 shows hydrogen bonds with R44 and Q529. The -CDOCKER interaction energy is 40.74. (F) Comparison of sorafenib, SC-43, and SC-40 in the association of SHP-1/STAT3 targeting and anti-HCC effect. ELISA, enzyme-linked immunosorbent assay.

2.2.19 SC-43 and SC-40 Show a Significant Anti-HCC Effect and Overcome the Resistance of Sorafenib SC-43 and SC-40 decreased the viability of HCC cells in a dose-dependent manner (FIG. 23A). Both SC-43 and SC-40 showed lower 50% inhibitory concentration, compared to sorafenib. In addition, SC-43 and SC-40 showed more potent inhibition of the p-STAT3-related signaling pathway (FIG. 23B). SC-43 revealed submicromolar inactivation of p-STAT3, relative to sorafenib (FIG. 23C). Furthermore, SC-43 and SC-40 resulted in significant apoptosis in sorafenib-resistant cells at submicromolar concentrations (FIG. 23D). The endogenous induction of p-STAT3 was observed in sorafenib-resistant cells, but not in parental Huh7 cells, which may explain why these cells showed resistance to sorafenib.

2.2.20 Molecular Models of the SHP-1/Sorafenib Complex

Our findings provide a molecular rationale for drug optimization on the basis of the crystal structure of SHP-1. We hypothesize that sorafenib binds to the N-SH2 domain and subsequently releases and activates the PTP domain (FIG. 23E). Sorafenib was docked into the pocket between the N-SH2 domain and formed a hydrogen bonding with R44 through the trifluoromethyl group. The interaction of sorafenib and the NSH2 domain might lead to a release of the D61 catalytic site and activation of SHP-1 activity. SC-43 act as a potent SHP-1 enhancer and was also docked in the same site. The trifluoromethyl group of SC-43 formed a hydrogen bond with Q529. In addition, the length of the phenylcyanyl group in SC-43 is shorter than pyridine-mehtylamide of sorafenib, which reduces the steric-hindering effect in the N-SH2 domain. Moreover, the meta connection of the phenyl ring between the urea and phenylcyanyl moiety in SC-43 reduces total length and results in a better fit in the pocket of N-SH2. The discrepancy in potency between sorafenib and SC-43 was likely attributable to these two factors. We further modified SC-43 based on bioisosteric substitution. For example, SC-40, with the replacement of the urea and phenylcyanyl moiety in SC-43 by sulfonamide and nitroaniline, respectively, was able to activate SHP-1 activity. Also, SC-40 demonstrated that the sulfonamide moiety formed hydrogen bonds with R44 and Q529 in the docking model. Together, this discrepancy in binding ability may affect the potency of pharmacological effect among sorafenib, SC-40, and SC-43 (FIG. 23F).

2.2.21 SHP-1 Mediates the Effects of SC Derivatives on p-STAT3 and Apoptosis

Figure 24:
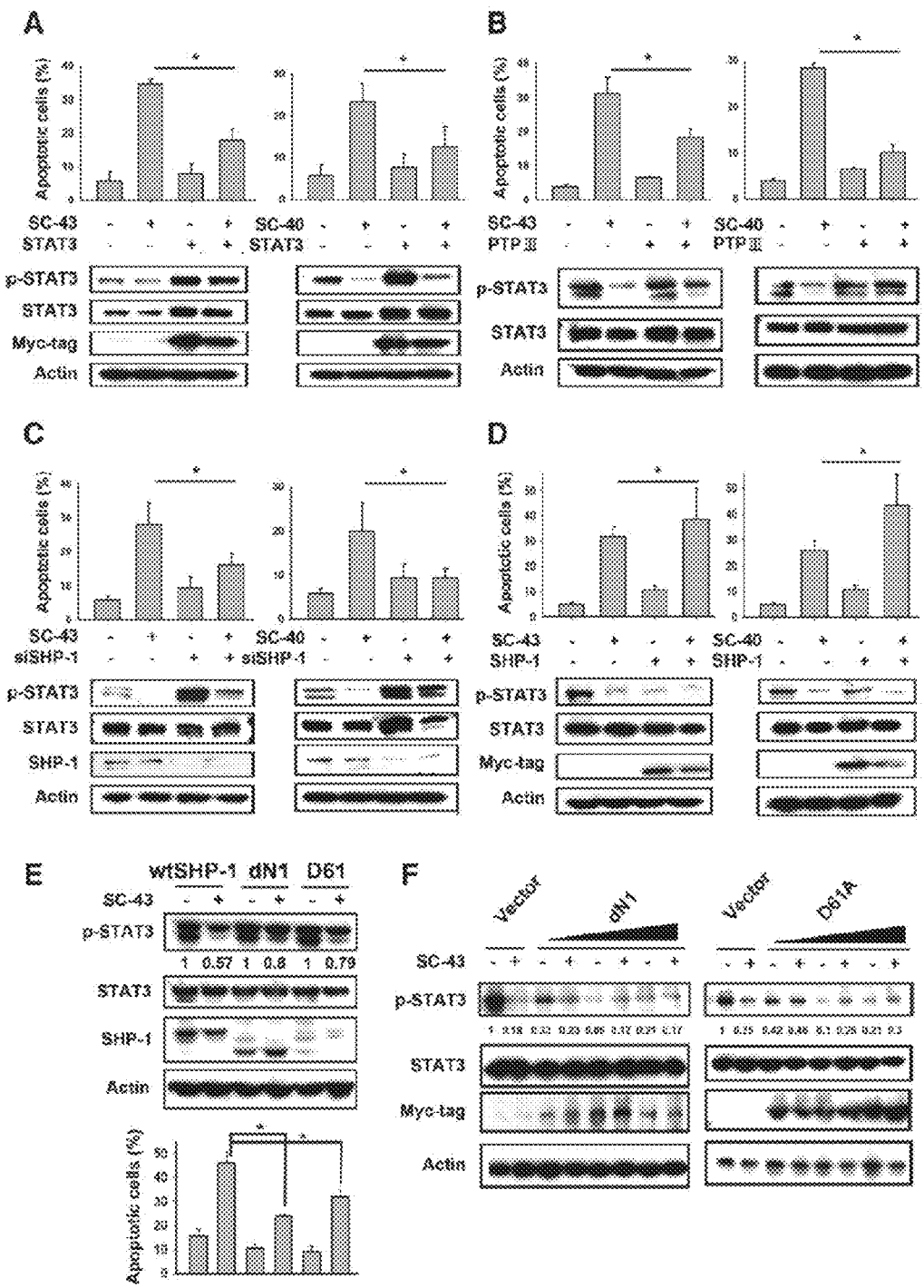
FIG. 24 shows target validation of SC derivatives in the SHP-1/STAT3-related signaling pathway. (A) Overexpression of STAT3 restores the effect of SC-43 and SC-40 on apoptosis. (B) Protective effects of SHP-1 inhibitor on SC derivative-induced apoptosis in PLC5 cells. (C) Inhibition of SHP-1 reversed the biological effects of SC-43 and SC-40 on p-STAT3 and apoptosis. (D) Overexpression of SHP-1 reinforced apoptosis as a result of SC-43 and SC-40 treatment in PLC5 cells. (E) dN1 and D61A mutants of SHP-1 were insensitive to SC-43-induced down-regulation of p-STAT3 and apoptotic effect. Apoptosis was evaluated by sub-G1 analysis. (F) Dose-dependent dN1 and D61A plasmid transfection restored the downregulation of p-STAT3 in SC-43-treated cells. Columns, mean; bars, standard deviation (n>3~6). *P<0.05; **P<0.01.

Apoptosis was inhibited in myc-tagged STAT3-overexpressing HCC cells after exposure to SC derivatives for 24 h as evidenced by sub-G1 analysis (FIG. 24A). In addition, SHP-1 phosphatase-specific inhibitor (PTPIII) reversed SC-induced cell death and inhibition of p-STAT3 (FIG. 24B). Silencing SHP-1 markedly restored SC-43 and SC-40-induced apoptosis and inhibition of p-STAT3 (FIG. 24C). Conversely, overexpression of WT SHP-1 induced potent apoptosis and inhibited p-STAT3 as a result of SC-43 and 40 treatments in PLC5 cells (FIG. 24D). Titration of dN1 or D61A also gradually restored inhibition of p-STAT3 in SC-43-treated cells; and the apoptosis induced by SC-43 was abolished in dN1 and D61A-expressing PLC5 cells (FIG. 24E,F).

2.2.22 SC-43 and 40 Show More Potent Inhibition of Tumor Growth, Compared to Sorafenib in Orthotopic and SC HCC Models Male NCr athymic nude mice (5-7 weeks of age) were obtained from the National Laboratory Animal Center (Taipei, Taiwan). All experimental procedures using these mice were done in accordance with protocols approved by the Institutional Laboratory Animal Care and Use Committee of National Taiwan University. Each mouse was inoculated within liver in the dorsal flank with $1 \times 10^4$ PLC5/luc cells suspended in 0.1 mL of serum-free medium containing 50% Matrigel (BD Biosciences). When tumors formed, mice received sorafenib or SC-43 tosylate (10 mg/kg) orally once daily. Tumor growth was monitored by non-invasive in vivo imaging system (IVIS) image system twice weekly.

Figure 25:
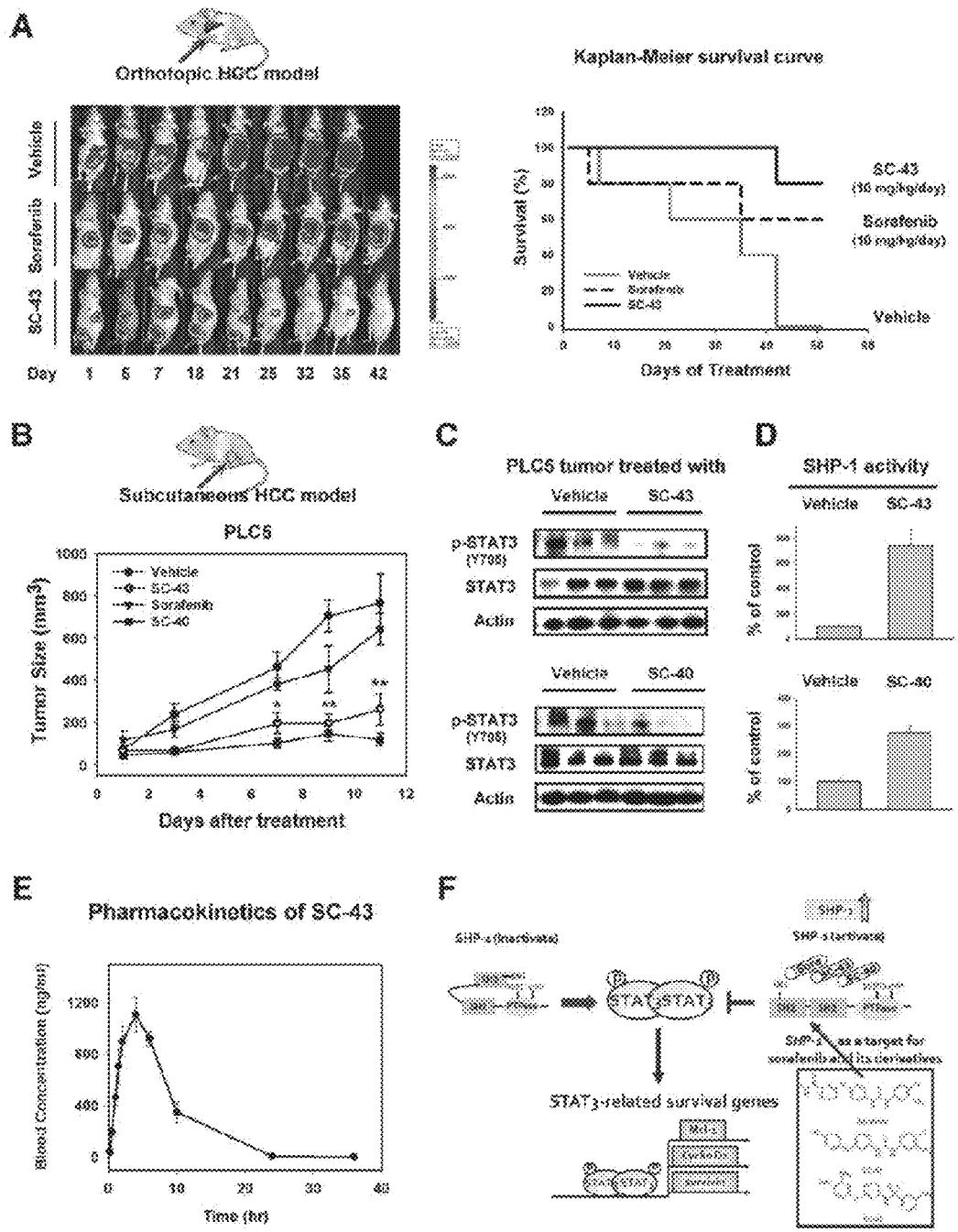
FIG. 25 shows in vivo effects of SC-43 and SC-40 on HCC xenograft and orthotopic animal models. (A)SC-43 treatment resulted in significant tumor growth inhibition and survival benefit in an HCC orthotopic model. Left: Tumor growth was monitored by the In Vivo Imaging System at the indicated times. Right: survival curve of HCC orthotopic mice receiving different adjuvant therapies at indicated times. PLC5/luc2-bearing orthotopic mice received sorafenib, SC-43, or vehicle orally at 10 mg/kg/day (n 5 6). (B)SC-43 and SC-40 treatment resulted in a significant antitumor effect on SC PLC5 tumor-bearing mice, compared to sorafenib. Mice received sorafenib or its derivatives at 10 mg/kg/day, and tumor growth was measured twice-weekly. Points, mean (n 5 10); bars, SE. *P<0.05; **P<0.01. (C) Analysis of p-STAT3 and STAT3 in PLC5 tumors. (D) SHP-1 phosphatase activity in SC-43- and SC-40-treated tumor sample. (E) Pharmacokinetics of SC-43. (F) Summary model. Sorafenib and its potent derivatives relieved the inhibitory N-SH2 domain of SHP-1 and therefore promoted apoptosis in HCC.

We established an HCC orthotopic model using luc2-expressed PLC5 cells inoculated into liver of nude mice. Long-term monitoring showed that SC-43 treatment had an evident anti-HCC effect and significant survival benefit, compared with mice treated with vehicle or sorafenib (FIG. 25A). In addition, SC PLC5 tumor-bearing mice were treated daily with vehicle, sorafenib, SC-43, or SC-40 at the dosage of 10 mg/kg/day orally. Compared to sorafenib, SC treatment had an inhibitory effect on tumor growth and the average tumor sizes of animals were less than half that of control mice at the end of treatment (FIG. 25B). To further correlate the molecular mechanism with the anticancer effect in vivo, p-STAT3 and SHP-1 activity in tumor extract from vehicle- and SC-treated mice was analyzed by immunoblotting. Down-regulation of p-STAT3 and elevation of SHP-1 activity were noted in SC-43/40-treated tumor lysate (FIG. 25C,D). The pharmacokinetics of SC-43 was determined (FIG. 25E). SC-43 exhibited a longer period of stability in vivo than that reported for sorafenib in a previous study.

Taken together, these results confirm that the sorafenib derivatives had increased SHP-1 activity that repressed the p-STAT3 involved in tumor inhibition in PLC5 xenograft and were more potent SHP-1 enhancers than sorafenib.

2.2.23 SC-49 Shows Better Apoptotic Effects than Sorafenib in HCC

Figure 26:
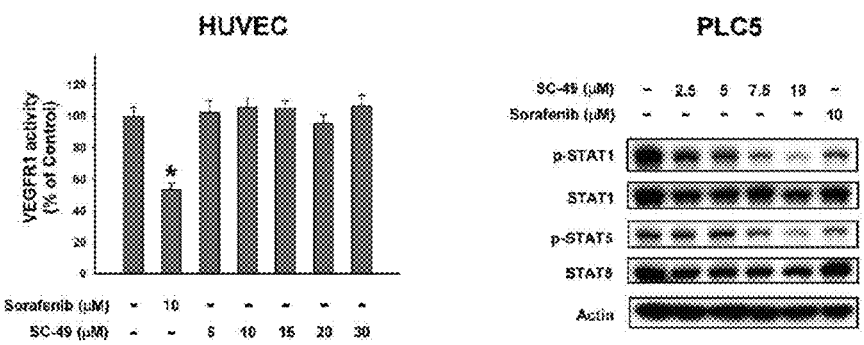
FIG. 26 shows SC-49 better apoptotic effects than sorafenib in HCC. (A) Left, effect of sorafenib and SC-49 on VEGFR1 activity. Right, effect of sorafenib and SC-49 on p-STAT1 and p-STAT5. Cells were exposed to sorafenib or SC-49 at the indicated doses for 24 h. Points show means with bars representing SD (n=6). (B) Dose escalation effects of sorafenib and SC-49 on apoptosis in HCC cells. Cells were exposed to sorafenib or SC-49 at the indicated doses for 24 h. Apoptotic cells were analysed by flow cytometry (sub-G1). (C) Effects of SC-49 on p-STAT3. Cells were treated with SC-49 or sorafenib at the indicated doses for 24 h.
Figure 26:
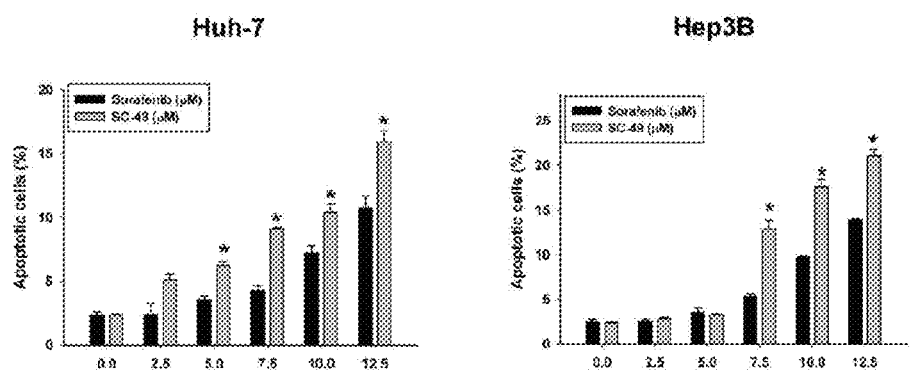
Figure 26:
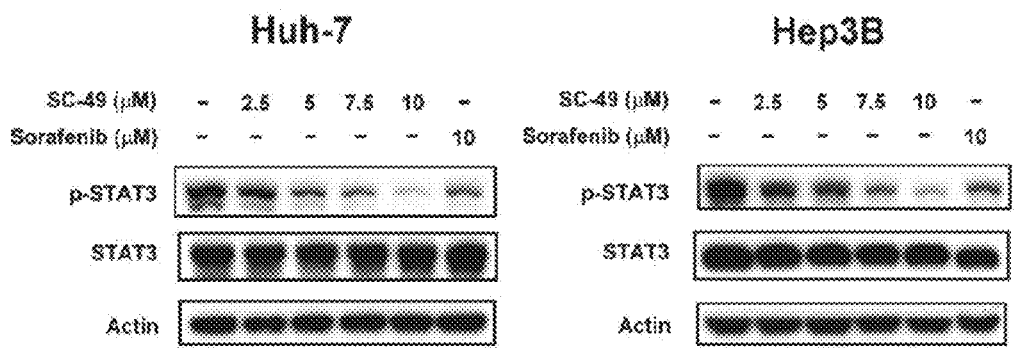

To further investigate the effect of SC-49 on angiogenesis, we tested the effect of SC-49 on the activity of VEGFR1 in HUVEC cells. As shown in FIG. 26A (left), sorafenib as a kinase inhibitor significantly inhibited the activity of VEGFR1 in HUVEC cells. However, unlike sorafenib, SC-49 did not affect the activity of VEGFR1 in HUVEC cells. We examined the effect of SC-49 on p-STAT1 and p-STAT5; SC-49 down-regulated both p-STAT1 and p-STAT5 in a dose dependent manner (FIG. 26A, right). Furthermore, in HCC cell lines, Huh-7 and Hep3B, we found that SC-49 induced more apoptotic cell death than sorafenib (FIG. 26B). In addition, SC-49 was more effective at down-regulating p-STAT3 than sorafenib in HCC cells (FIG. 26C). These data suggest that SC-49, a sorafenib derivative without kinase inhibitory activity, is a more potent anti-tumour agent than sorafenib and that its effect is induced by targeting the STAT3 signalling pathway.

2.2.24 In Vivo Effect of SC-49 in Huh-7 Xenograft Tumour

Figure 27:
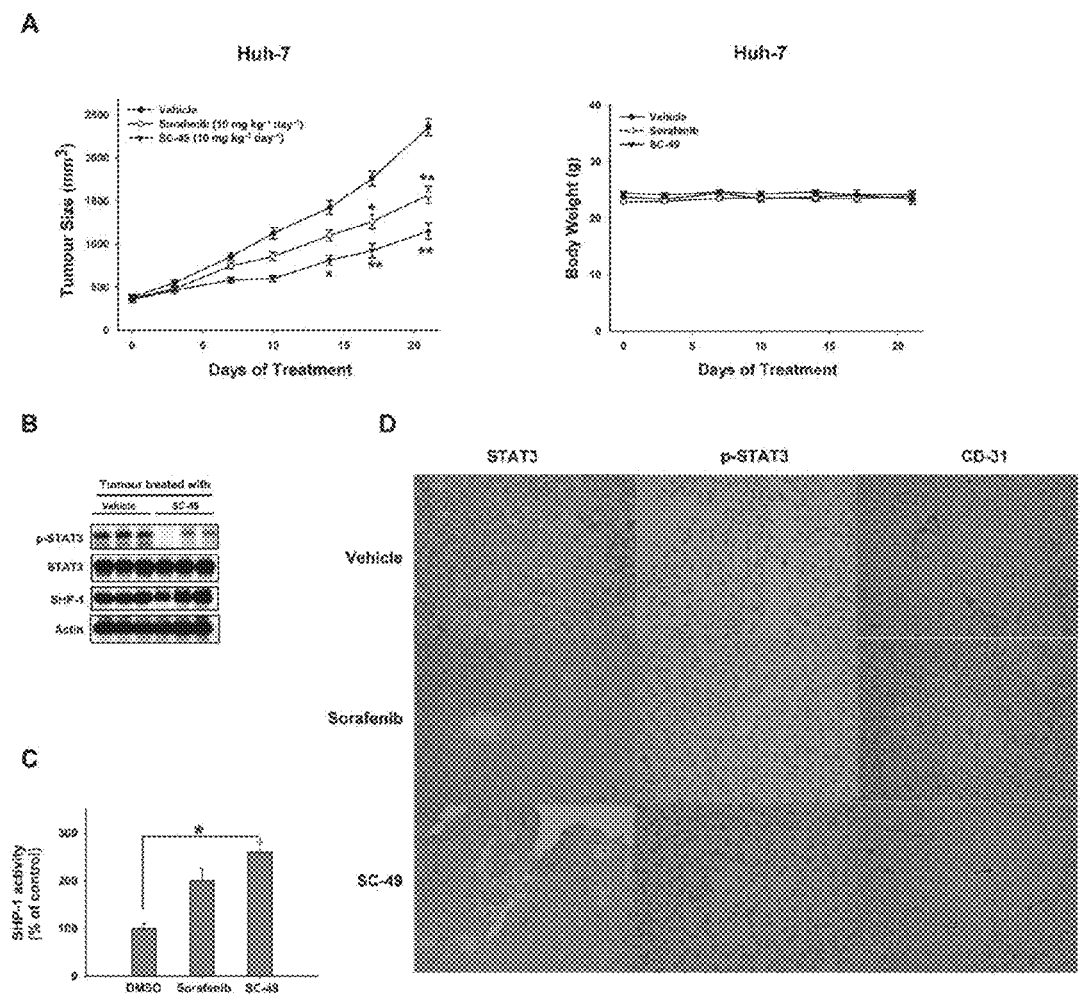
FIG. 27 shows in vivo effects of SC-49 in Huh-7 xenograft tumour. (A) Left, SC-49 showed significant anti-tumour effect on Huh-7 tumours. Right, body weight. Points show means with bars representing SEM (n=6). *, P<0.05; **, P<0.01. (B) Western blot analysis of p-STAT3, STAT3, and SHP-1 in Huh7 tumours. (C) Analysis of SHP-1 activity. Columns show means with bars representing SD (n=6). *P<0.05 versus vehicle group. (D) Immunohistochemical staining for tumours. Slides were then stained using the Leica Microsystems BONDMAX autostainer according to the manufacturer's protocol (400 folds).

To further examine the effect of SC-49, we next tested the effect of SC-49 on Huh-7 xenograft tumours in vivo. As shown in FIG. 27A (left), treatment of mice with SC-49 at a dose of 10 mg·kg-1·day-1 p.o. significantly reduced the growth of the Huh-7 tumour and this anti-tumour effect was better than that of sorafenib in vivo. As shown in FIG. 27A (right), animals had stable body weights throughout the course of study. In addition, SC-49 down-regulated p-STAT3 in Huh-7 tumours (FIG. 27B). SC-49 and sorafenib enhanced the activity of SHP-1 in Huh-7 tumours (FIG. 27C) Immunohistochemical staining for STAT3 showed no obvious significantly different cytoplasmic expression in all groups (FIG. 27D). The treatment of both sorafenib and SC-49 decreased the nuclear expression of P-STAT3 (FIG. 27D). From the immunohistochemical stain for CD-31, all the groups showed a similar vascular density in the tumour areas (FIG. 27D).

These data indicate that SC-49 exhibited better in vivo effects than sorafenib through an SHP-1-dependent inhibitory effect on STAT3.

2.2.25 Downregulation of p-STAT3-Related Molecules is Associated with the Sensitizing Effect of SC-59

Figure 28:
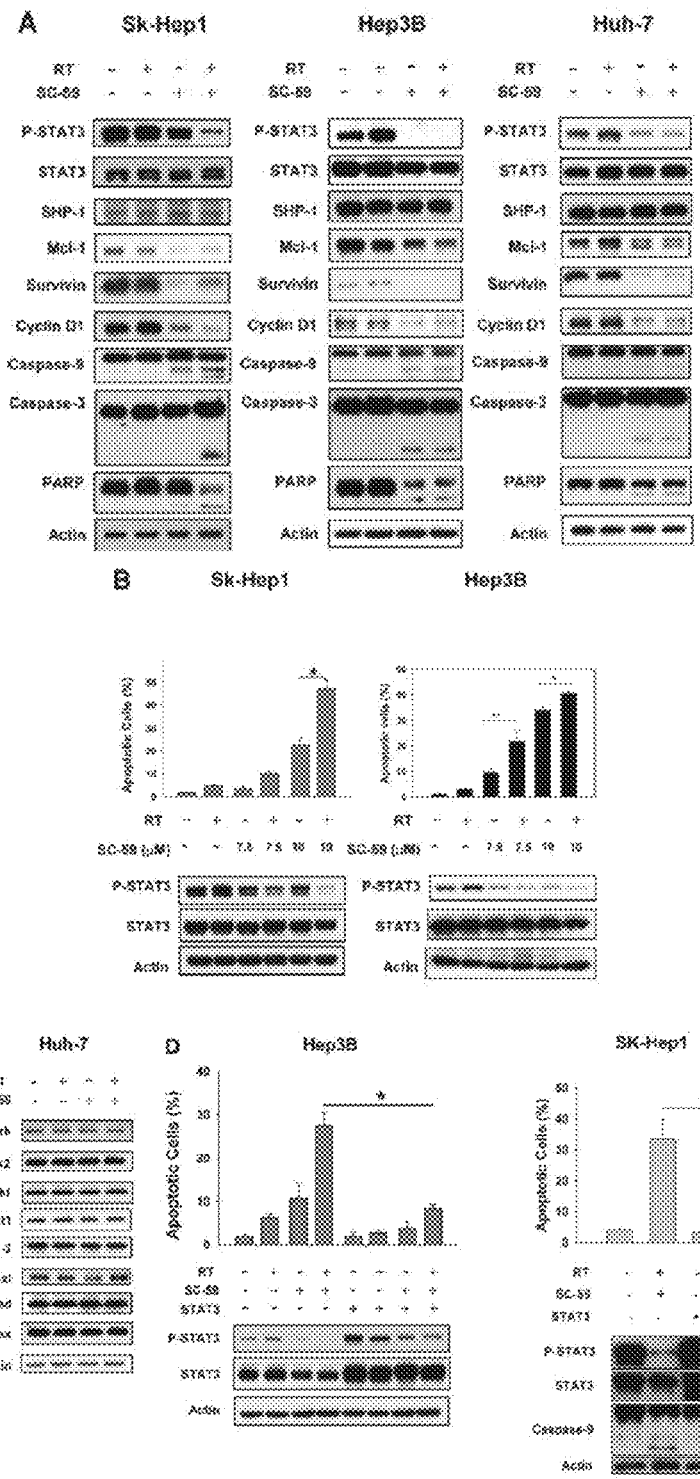
FIG. 28 shows that STAT3 downregulation is associated with the sensitizing effects of SC-59. SC-59 and radiation affected (A) the protein levels of P-STAT3/STAT3-regulated downstream molecules in SK-Hep1, Hep3B, and Huh-7 HCC cell lines and (B) the dose-escalation effects of SC-59 on phospho-STAT3 and apoptotic effect of radiosensitization. (C)SC-59 and radiation did not affect the other apoptosis-related signaling axis in Huh7 cells. (D) Ectopic expression of STAT3 protected HCC cells against apoptosis induced by radiation and SC-59 combined treatment. Hep3B and SK-Hep1 cells (wild type or ectopic expression of STAT3) were pretreated with DMSO or 4 Gy radiation (one fraction), incubated for 48 h, then treated with DMSO or 10 1M SC-59 for 16 h, and analyzed by flow cytometry and western blotting. Data are representative of three independent experiments. Columns, mean; bars, SD (n=3). *, P<0.05, **, P<0.01

To further investigate the underlying mechanism by which SC-59 overcomes radioresistance in HCC, we examined the alterations in signal transduction induced by SC-59 in HCC. As shown in FIG. 28A, SC-59 downregulated phospho-STAT3 (p-STAT3) at tyrosine 705 along with its downstream molecules, such as Mcl-1, survivin, and cyclin D1. Apoptosis induced by the combination of SC-59 and radiotherapy was further confirmed by PARP cleavage and the activation of caspase-9 and caspase-3 (FIG. 28A). Notably, SHP-1, a vital protein tyrosine phosphatase for p-STAT3 (Y705), was not affected by SC-59 or radiotherapy. Furthermore, in SK-Hep1 and Hep3B cell lines, dose-dependent apoptotic assay confirmed that downregulation of p-STAT3 was associated with the synergistic effect of SC-59 and radiotherapy (FIG. 28B). Other apoptosis-related molecules, p-Erk, Erk, p-Akt, Akt, Bcl-2, Bcl-x1, Bad, and Bax were not changed in Huh7 cells exposed to SC-59, radiotherapy, or a combination (FIG. 28C) Importantly, ectopic STAT3 in Hep3B and SK-Hep1 cells significantly abolished SC-59-induced STAT3 inhibition and radiosensitivity (FIG. 28D). These results suggest that STAT3-related signaling mediates the combined effect of SC-59 and radiotherapy.

Figure 29:
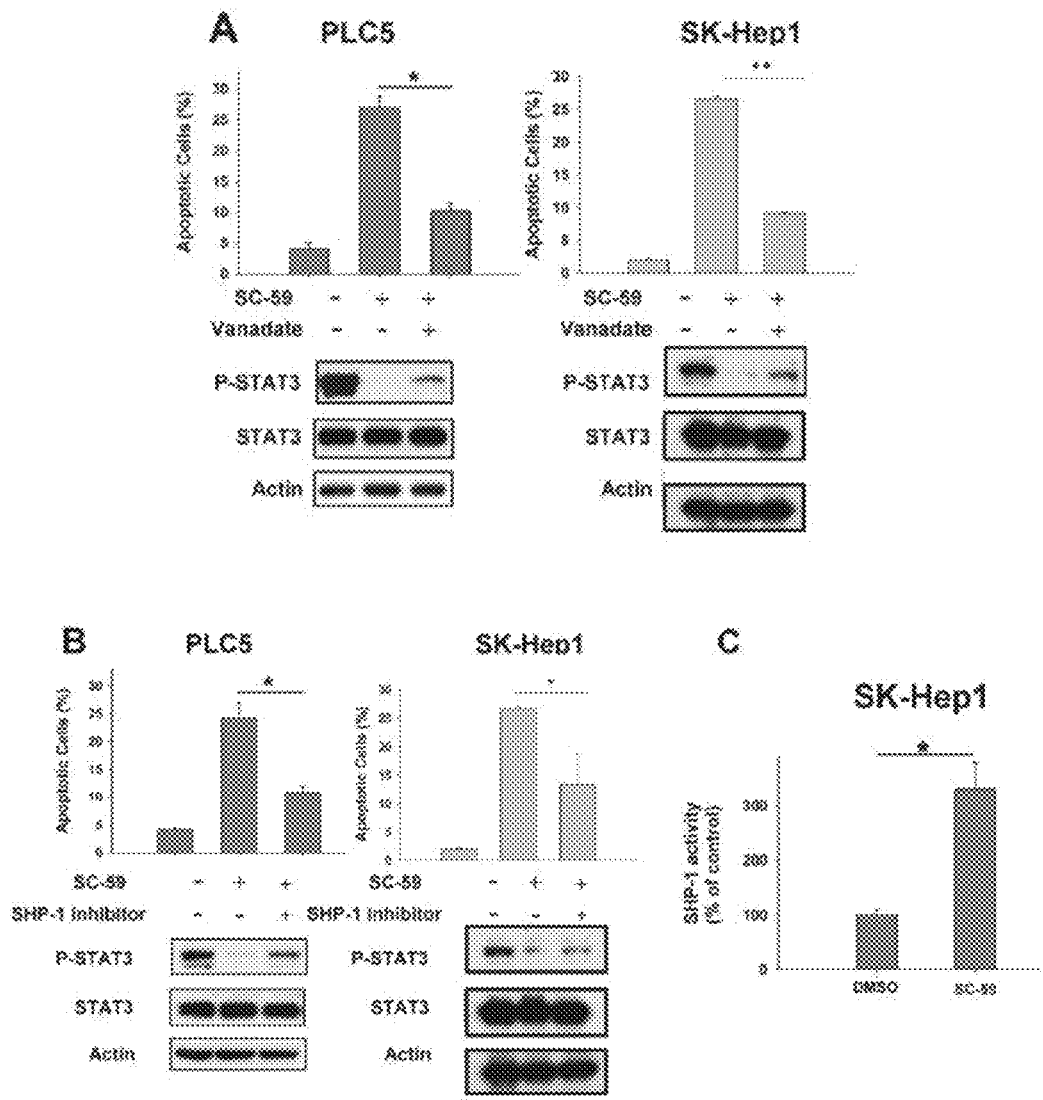
FIG. 29 shows that inhibition of SHP-1 reverses the effects of SC-59 on phospho-STAT3 and apoptosis. (A) Vanadate, a non-specific phosphatase inhibitor, (B) specific SHP-1 inhibitor and (C) activity of SHP-1. (D) Silencing SHP-1 by siRNA reduces the effects of SC-59 on p-STAT3 and radiosensitization in HCC cells. (E) Knockdown of SHP-2 or PTP-1B did not affect SC-59-induced p-STAT3 inhibition and apoptosis. Columns, mean; bars, SD (n=3). *, P<0.05, **, P<0.01.
Figure 29:
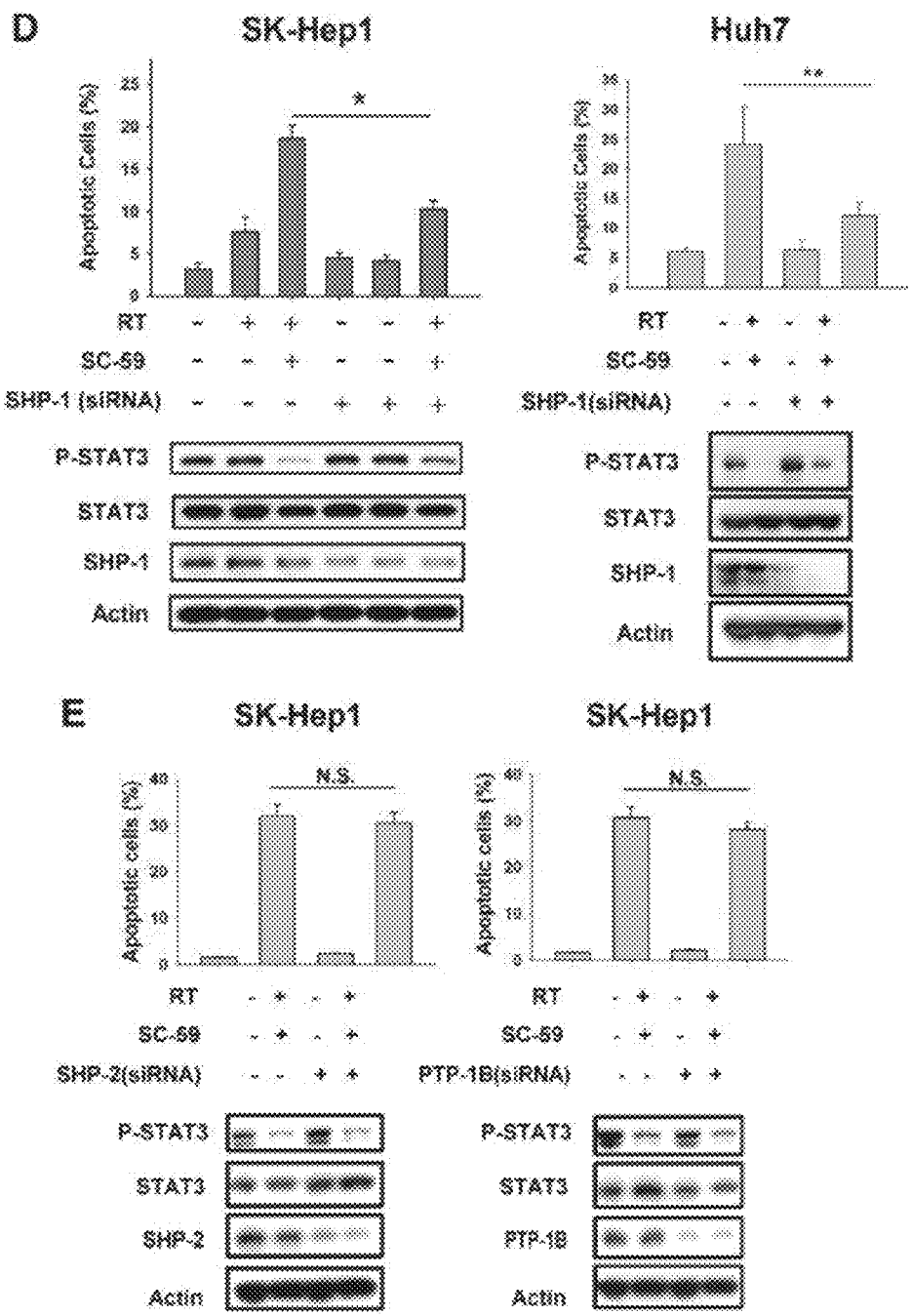

2.2.26 Inhibition of SHP-1 Reverses SC-59-Induced Apoptosis and STAT3 Inhibition To further investigate the mechanism by which SC-59 downregulates p-STAT3 in HCC cells, we examined the role of protein phosphatase on the effect of on pSTAT3. Our data showed that vanadate, a nonspecific protein tyrosine phosphatase inhibitor, reversed the downregulation of pSTAT3 and the apoptotic effect in PLC5 and SK-Hep1 cells after treatment with SC-59 (FIG. 29A). Further, a specific SHP-1 inhibitor (PTP III) significantly abolished the SC-59-induced STAT3 inhibition and apoptosis, indicating that SHP-1 plays a role in SC-59-mediated cell death and radiosensitivity (FIG. 29B). Data in FIG. 2A showed that SC-59 did not affect the expression level of SHP-1. But, SC-59 significantly increased the phosphatase activity of SHP-1 in SK-Hep1 cells (FIG. 29C). Knockdown of SHP-1 using specific siRNA reversed SC-59 and radiotherapy-induced p-STAT3 inhibition and apoptosis in Huh7 and SK-Hep1 HCC cell lines (FIG. 29D). However, silencing of other STAT3-related protein tyrosine phosphatases including SHP-2 and PTP-1B did not affect the p-STAT3 inhibition and apoptosis induced by SC-59 plus radiotherapy (FIG. 29E). These data suggest that SC-59 sensitizes HCC cells to radiotherapy and inhibits p-STAT3 signaling by targeting SHP-1.

2.2.27 SC-59 Results in Potent Radiosensitivity in Huh 7 Xenografts

Figure 30:
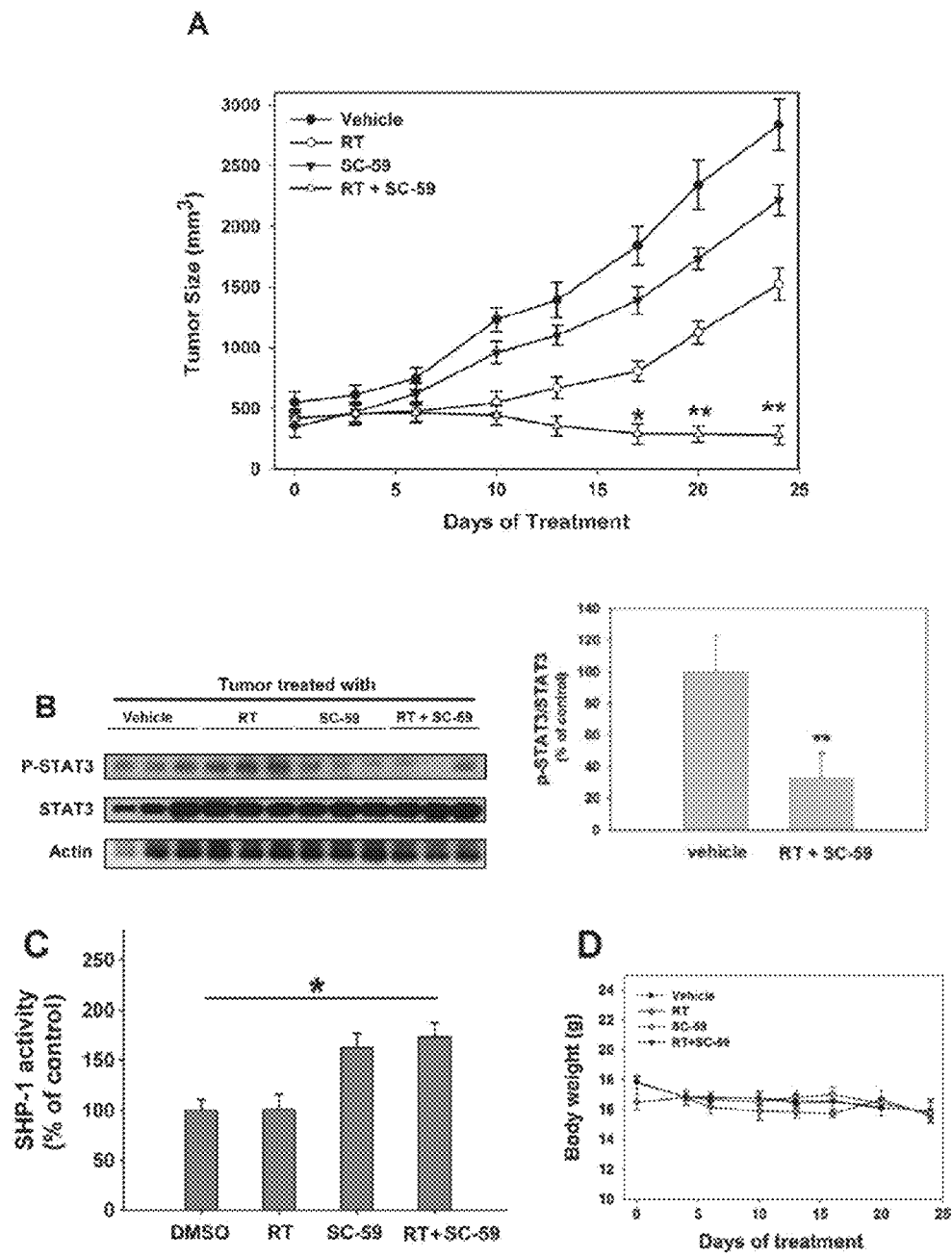
FIG. 30 shows that combined SC-59 and radiation treatment inhibits Huh-7 xenograft tumor growth in nude mice. (A) The effects of SC-59 and radiation on tumor growth. Each mouse was inoculated subcutaneously in the right leg with 106 Huh-7 cells suspended in Matrigel. When the tumor reached a volume of 400-600 mm3, mice received vehicle, 5 Gy radiation (one fraction per day) for 4 days, or 10 mg/kg SC-59 p.o. once daily, or a combination for the duration of the study. The data points indicate the mean values (n=6) and the bars indicate the standard error. There were significant differences between the combined treatment group and the vehicle control group (*, P<0.05, **, P<0.01). (B) Left, the expression of P-STAT3 in the Huh-7 tumors was analyzed by western blot. Right, quantified data for p-STAT3 to STAT3. (C) The activity of SHP-1 in Huh-7 tumors. Values are means±SD, *, P<0.05. (D) Body weight of mice after SC-59 and RT treatment. (E) The tumor inhibition effect of sorafenib and RT. Mice received vehicle, 5 Gy radiations (one fraction per day) for 4 days, or 10 mg/kg sorafenib p.o. once daily, or a combination for the duration of the study. The data points indicate the mean values (n=6) and the bars indicate the standard error. (F) The effect of sorafenib and radiation on p-STAT3 inhibition. (G) The quantification of p-STAT3 to STAT3 in tumor sample with sorafenib and RT treatment. (H) Body weight of mice treated with vehicle, RT, sorafenib, and combination.

To evaluate the sensitization of HCC cells to radiotherapy by SC-59 in vivo, we established a preclinical HCC model by subcutaneously inoculating nude mice with Huh7 cells Importantly, mice treated with SC-59 plus radiotherapy displayed significant tumor growth inhibition compared to radiotherapy or SC-59 alone (FIG. 30A). To further elucidate the molecular events responsible for this synergistic effect, we examined the expression level of p-STAT3 in the tumor extract. SC-59 resulted in clear inhibition of p-STAT3 in the treated tumor samples. Notably, more significant p-STAT3 inhibition was also found in tumor samples that underwent SC-59 plus radiotherapy treatment supporting the synergistic anti-HCC effect of this combination (FIG. 30B). Moreover, induction of SHP-1 phosphatase activity was observed in both SC-59-treated and in SC-59 plus radiotherapy-treated tumor samples (FIG. 30C). Notably, there is no significant difference in body weight after SC-59 treatment (FIG. 30D). Furthermore, to compare the sensitizing effect of SC-59 to sorafenib, we also established a HCC subcutaneous model to evaluate the therapeutic efficiency of sorafenib plus RT. As shown in FIG. 30E, compared to SC-59, sorafenib did not display a better synergistic effect when used in combination with radiotherapy. Moreover, tumor sample treated with sorafenib and RT did not exhibit a better p-STAT3 inhibition compared to SC-59 and RT (FIGS. 30F and G). Also, there is no significant change in tumor weight after sorafenib treatment (FIG. 30H). Collectively, these in vivo findings suggest that SC-59 acts as a potent STAT3 inhibitor, and has a synergistic effect when used in combination with radiotherapy for HCC by targeting SHP-1.

Figure 31:
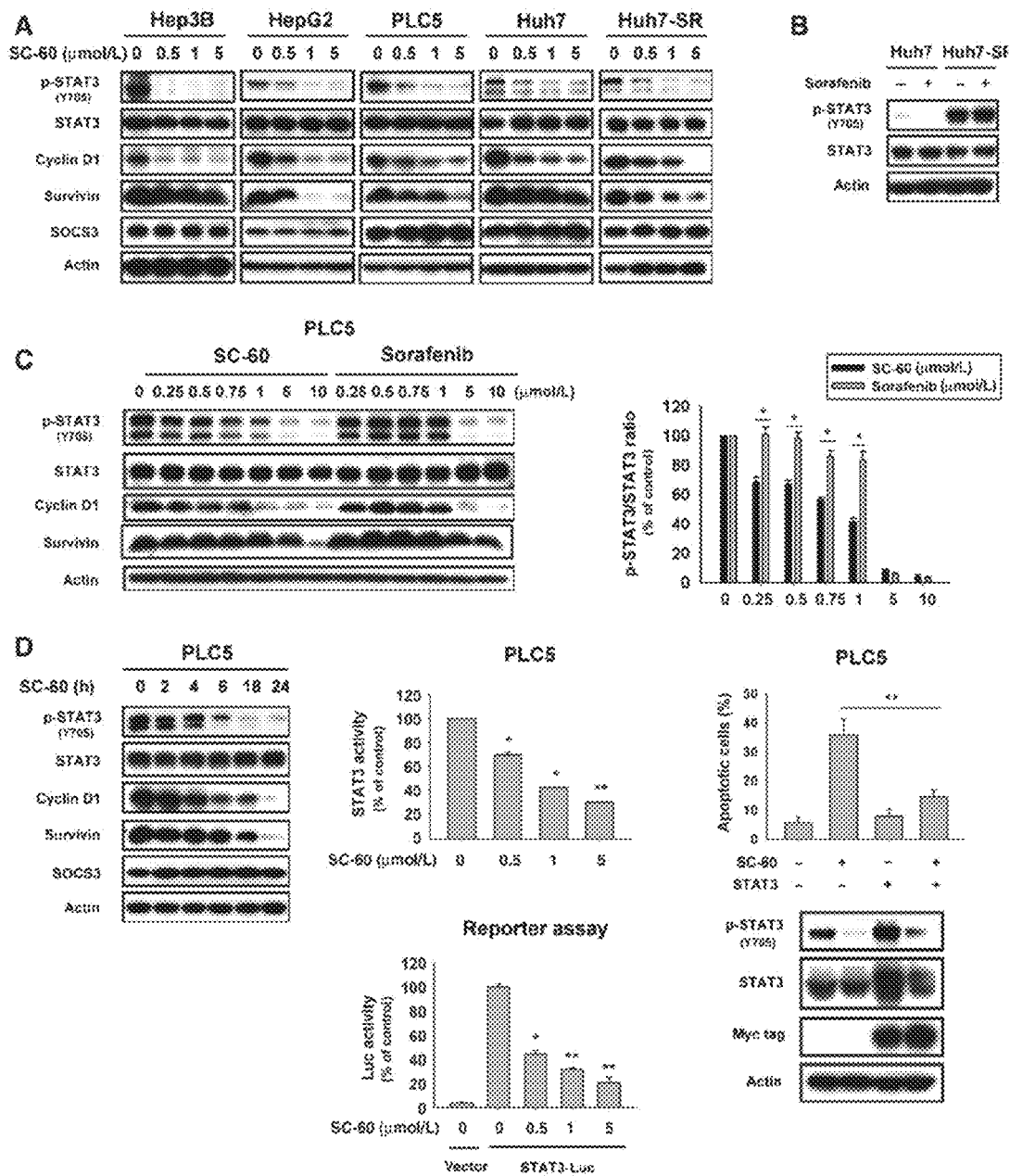
FIG. 31 shows that downregulation of p-STAT3 (Y705) is associated with sensitizing effects of SC-60 in hepatocellular carcinoma cells. (A) dose-dependent effects of SC-60 on STAT3-related proteins. (B) activated-STAT3 was found in sorafenib-resistant Huh7 cells. (C) dose-dependent effects of SC-60 and sorafenib on STAT3-related proteins. PLC5 cells were exposed to the indicated doses for 24 hours. (D) left, time-dependent assay of STAT3-related signaling pathway in SC-60-treated PLC5 cells. Middle, SC-60 decreases STAT3 activity in the submicro molar range. Top, dose-escalation effects of SC-60 on pSTAT3 in PLC5 cells; bottom, STAT3 reporter analysis of SC-60 in PLC5 cells. PLC5 cells were exposed to the indicated drugs for 24 hours (top) or 12 hours (bottom) for reporter assay. Right, ectopic STAT3 reverses the apoptotic effect of SC-60. PLC5 cells stably expressed STAT3 with Myc-tag, were treated with SC-60 5 mmol/L for 24 hours, and the percentage of apoptosis was measured by sub-G1 analysis. *, P<0.05; **, P<0.01.

2.2.28 Downregulation of p-STAT3 Contributes to the Apoptotic Effect of SC-60 in Hepatocellular Carcinoma To elucidate the mechanism by which SC-60 induces apoptosis in hepatocellular carcinoma, we examined the alterations in signal transduction induced by SC-60 in hepatocellular carcinoma. As shown in FIG. 31A, SC-60 downregulated phospho-STAT3 (p-STAT3) at tyrosine 705 in a dose-dependent manner. Therefore, the resistance of Huh7-SR cells to sorafenib may be explained by the activation of p-STAT3 (FIG. 31B). Compared with sorafenib, SC-60 showed significant inhibition of STAT3-related signaling in the submolar range (FIG. 31C). Moreover, SC-60 downregulated p-STAT3 and its related proteins such as cyclin D1 and surviving in a time-dependent manner (FIG. 31D, left). Also, as shown in FIG. 31D (middle), SC-60 showed significant inhibition of STAT3 activity, demonstrated by STAT3 ELISA and Luc reporter assay. Importantly, PLC5 cells expressing ectopic STAT3 were insensitive to SC-60-induced STAT3 inhibition and apoptosis (FIG. 31D, right). These results suggest that STAT3 mediates SC-60-induced apoptosis in hepatocellular carcinoma cells.

2.2.29 SC-60 Shows More Significant Survival Benefit and Tumor Inhibition Compared with Sorafenib in a Preclinical Hepatocellular Carcinoma Model To evaluate the antitumor effect of SC-60 on hepatocellular carcinoma, we established a preclinical hepatocellular carcinoma orthotopic model using luc2-expressed PLC5 cells inoculated into the liver of nude mice. Importantly, SC-60-treated mice displayed significant survival benefits compared with mice treated with vehicle or sorafenib (FIG. 32A). Also, SC-60 had an evident anti-hepatocellular carcinoma effect in PLC bearing subcutaneous mice with 10 mg/kg/d treatment (FIG. 32B). Compared with sorafenib, SC-60 $_{treatment}$ had an inhibitory effect on tumor growth and the average tumor sizes of animals were less than half of those of control mice at the end of treatment. SC-60-induced molecular events of SHP-1/STAT-related signaling were also found in tumor samples (FIG. 32B, middle and left). Notably, mice inoculated with PLC5 cells expressing STAT3 were insensitive to SC-60 (FIG. 32C). These findings suggest that SC-60 acts as a potent STAT3 inhibitor and SHP-1 enhancer, and thus induces its anti-hepatocellular carcinoma effect via a STAT3-related signaling pathway. To further validate the possibility that SHP-1/STAT3-related signaling is a biomarker in patients with hepatocellular carcinoma, we examined the expression status of SHP-1 and p-STAT3 in clinical patients with hepatocellular carcinoma. STAT3 showed strong cytoplasmic expression in liver cancer cells but mild cytoplasmic expression and negative nuclear expression in adjacent noncancer liver cells. On the contrary, SHP-1 showed moderate cytoplasmic expression with negative nuclear expression in liver cancer cells but mild cytoplasmic expression with negative nuclear expression in adjacent noncancer liver cells (FIG. 32D). Collectively, these results confirm that SC-60, a dimer-based sorafenib derivative, had increased SHP-1 activity that repressed the p-STAT3-related signaling and is involved in tumor inhibition in PLC5 xenograft.

2.3 Compound SC-111

The present invention provides a compound 1-(4-chloro-3-(trifluoromethyl)phenyl)-3-(3-(4-cyanophenoxy)-4-fluorophenyl)urea (SC-111), SC-111 is the structure relative to SC-43.

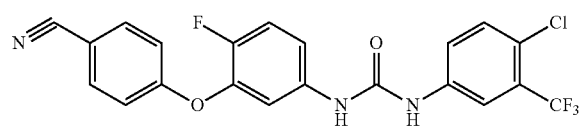 [SMILES: N#Cc1ccc(Oc2cc(NC(=O)Nc3ccc(Cl)c(C(F)(F)F)c3)ccc2F)cc1]

$^1$H NMR (400 MHz, MeOD-d$_4$): δ7.95 (d, J=2.4 Hz, 1H), 7.72 (d, J=8.8 Hz, 2H), 7.63 (dd, J=8.8, 2.4 Hz, 1H), 7.51-7.48 (m, 2H), 7.28-7.21 (m, 2H), 7.09 (d, J=8.8 Hz, 2H); $^{13}$C NMR (100 MHz, MeOD-d$_4$): δ162.6, 154.5, 152.6, 150.2, 142.5, 140.0, 137.6, 135.4, 132.9, 129.1 (m), 125.5, 124.2, 119.5, 118.7 (m), 118.4 (m), 118.1, 117.9, 115.3, 107.1; HRMS calculated for C21H12ClF4N3O2: 449.0554. Found: 449.0558.

2.3.1 SC-111 is Specific SHP-1 Inhibitor

To further investigate the mechanism by which SC-111 downregulates p-STAT3 in HCC cells, we examined the role of protein phosphatase on the effect of on pSTAT3. Our data showed that vanadate, a nonspecific protein tyrosine phosphatase inhibitor, reversed the downregulation of pSTAT3 after treatment with SC-111. Further, a specific SHP-1 inhibitor (PTP III) significantly abolished the SC-111-induced STAT3 inhibition and apoptosis, indicating that SHP-1 plays a role in SC-111-mediated cell death (FIG. 33).

2.3.2 SC-111 Exhibits Antitumor Effect in HCC Cells

SC-111 exhibits antitumor effect in vitro. SC-43 shows a significant cytotoxicity in HCC cells (IC50~0.5 μM). SHP-1/STAT3-related signaling pathway acts as a vital target for the anti-tumor effect of SC-111. See FIG. 34 the cytotoxicity of SC-111 in HCC cells

2.4 Comparable Example

The present invention also provides a compound N,N'-bis(3-(4-cyanophenoxyl)phenyl)cyclopropane-1,1-dicarboxamide (SC-67) as a comparable example, SC-67 is derived from SC-1 and the structure relative to SC-43.

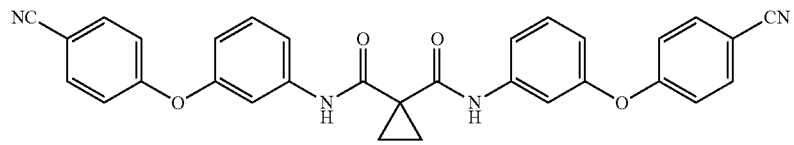 [SMILES: N#Cc1ccc(Oc2cccc(NC(=O)C3(C(=O)Nc4cccc(Oc5ccc(C#N)cc5)c4)CC3)c2)cc1]

$^1$H NMR (400 MHz, CDCl$_3$): δ 7.57 (d, J=9.2 Hz, 4H), 7.47 (s, 1H), 7.32 (t, J=8.0 Hz, 1H), 7.28 (d, J=8.0 Hz, 1H), 6.99 (d, J=9.2 Hz, 4H), 6.78 (dd, J=7.6 Hz, 2.2 Hz, 2H), 1.76-1.75 (m, 4H); HRMS calculated for C$_{31}$H$_{22}$N$_4$O$_4$ (M+Na)$^+$: 537.1539. Found: 537.1562.

As shown in FIG. 35, although compound SC-67 is derived from SC-1 and the structure relative to SC-43. However, SC-67 has no activity in inducing cancer cells (PLC5) apoptosis The compounds of the present invention act as SHP-1 agonists and have the ability to reduce P-STAT3, and are useful for treating certain diseases, such as hepatocellular carcinoma, leukemia, lung cancer, breast cancer, renal cancer, thyroid cancer colon, head or neck cancer and osteoporosis.

We claim:

1. A compound which is represented by Formula I

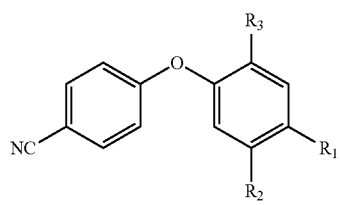

wherein R$_1$, and R$_3$ are independently hydrogen, and R$_2$ is

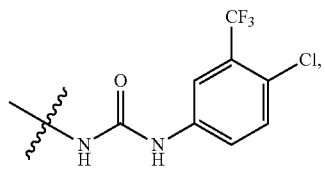 [SMILES: *NC(=O)Nc1ccc(Cl)c(C(F)(F)F)c1]

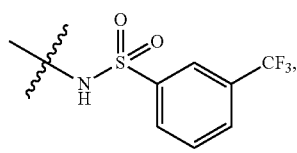 [SMILES: *NS(=O)(=O)c1cccc(C(F)(F)F)c1]

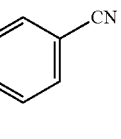

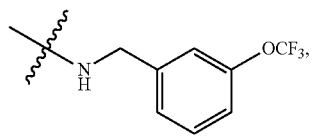 [SMILES: *NCc1cccc(OC(F)(F)F)c1]

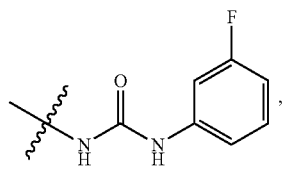 [SMILES: *NC(=O)Nc1cccc(F)c1]

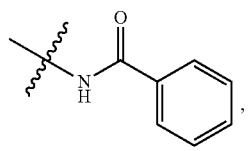 [SMILES: *NC(=O)c1ccccc1]

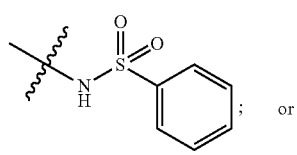 [SMILES: *NS(=O)(=O)c1ccccc1]

; or wherein R$_1$ is independently hydrogen; R$_3$ is methyl; and R$_2$ is

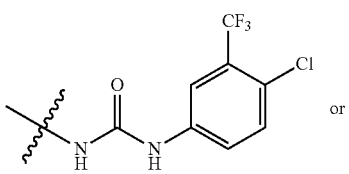 [SMILES: *NC(=O)Nc1ccc(Cl)c(C(F)(F)F)c1] or

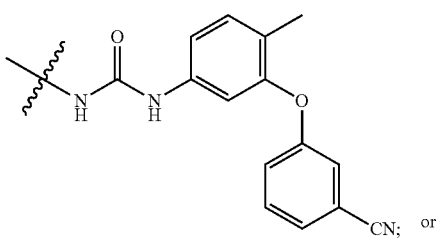

wherein R₂ and R₃ are independently hydrogen; and R₁ is

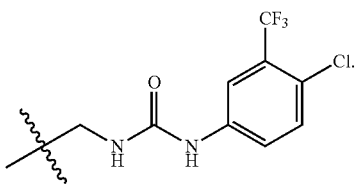 [SMILES: *CNC(=O)Nc1ccc(Cl)c(C(F)(F)F)c1]

2. A compound is

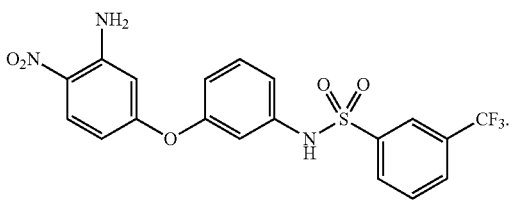 [SMILES: Nc1cc(Oc2cccc(NS(=O)(=O)c3cccc(C(F)(F)F)c3)c2)ccc1[N+](=O)[O-]]

3. A compound is

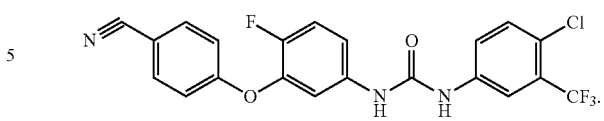

4. A pharmaceutical composition comprising a compound as defined in any of claims 1 to 3 and a pharmacological acceptable carrier.

5. A pharmaceutical composition for increasing Src homology-2 containing protein tyrosine phosphatase-1 (SHP-1) expression in a cell, comprising a compound as defined in any of claims 1 to 3 and a pharmacological acceptable carrier.

6. A pharmaceutical composition for treating a disease or condition characterized by decreased Src homology-2 containing protein tyrosine phosphatase-1 (SHP-1), comprising a compound as defined in any of claims 1 to 3 and a pharmacological acceptable carrier, wherein the disease or condition is a cancer or osteoporosis.

7. The pharmaceutical composition of claim 6, wherein the cancer is hepatocellular carcinoma, leukemia, lung cancer, breast cancer, renal cancer, thyroid cancer colon, head or neck cancer.

8. A method for increasing Src homology-2 containing protein tyrosine phosphatase-1 (SHP-1) expression in a cell, comprising contacting the cell with an effective amount of a compound as defined in any of claims 1 to 3 or a pharmaceutical composition of claim 4.

9. A method for treating a disease or condition characterized by decreased Src homology-2 containing protein tyrosine phosphatase-1 (SHP-1) expression in a subject in need thereof, comprising administering to the subject an effective amount of a compound as defined in any of claims 1 to 3 or a pharmaceutical composition of claim 4, wherein the disease or condition is a cancer or osteoporosis.

10. The method of claim 9, wherein the cancer is hepatocellular carcinoma, leukemia, lung cancer, breast cancer, renal cancer, thyroid cancer colon, head or neck cancer.

\* \* \* \* \*